(12) United States Patent
Ziv et al.

(10) Patent No.: US 10,279,161 B2
(45) Date of Patent: May 7, 2019

(54) STOPCOCK

(71) Applicant: ELCAM MEDICAL AGRICULTURAL COOPERATIVE ASSOCIATION LTD., Kibbutz Baram (IL)

(72) Inventors: David Ziv, Kibbutz Baram (IL); Gil Tomer, Kibbutz Yiron (IL)

(73) Assignee: Elcam Medical Agricultural Cooperative Association Ltd., Kibbutz Baram (IL)

( * ) Notice: Subject to any disclaimer, the term of this patent is extended or adjusted under 35 U.S.C. 154(b) by 0 days.

(21) Appl. No.: 14/665,850

(22) Filed: Mar. 23, 2015

(65) Prior Publication Data
US 2015/0196749 A1     Jul. 16, 2015

Related U.S. Application Data

(60) Continuation of application No. 13/937,053, filed on Jul. 8, 2013, now Pat. No. 9,016,316, which is a
(Continued)

(51) Int. Cl.
*F16K 5/04*        (2006.01)
*A61M 39/22*     (2006.01)
(Continued)

(52) U.S. Cl.
CPC ......... *A61M 39/223* (2013.01); *F16K 5/0407* (2013.01); *F16K 11/0833* (2013.01);
(Continued)

(58) Field of Classification Search
None
See application file for complete search history.

(56) References Cited

U.S. PATENT DOCUMENTS 2,868,176 A    1/1959   Bennett
3,721,265 A    3/1973   Hoffland
(Continued)

FOREIGN PATENT DOCUMENTS

EP     1234596 A4    9/2004
EP     1234596 B1    1/2007
(Continued)

OTHER PUBLICATIONS

European Search Report dated Nov. 4, 2014, which issued during the prosecution of Applicant's European Application No. 14177670. 8. 6 pages.
(Continued)

*Primary Examiner* — John Fox
(74) *Attorney, Agent, or Firm* — Fish & Richardson P.C.

(57) ABSTRACT

According to a preferred embodiment of the present invention there is provided a stopcock including a housing element defining at least first, second and third ports, a handle element which is selectably positionable relative to the housing element, at least one fluid passageway communicating between at least two of the at least first, second and third ports, the at least one fluid passageway being selectably defined by at least one of the housing element and the handle element, the at least one fluid passageway being configured for enabling flushing an internal volume of at least one of the first, second and third ports by a fluid flow which does not flow entirely through the port whose internal volume is being flushed.

22 Claims, 65 Drawing Sheets

Related U.S. Application Data division of application No. 13/167,871, filed on Jun. 24, 2011, now Pat. No. 8,534,321, which is a continuation of application No. 11/574,618, filed as application No. PCT/IL2005/000925 on Aug. 29, 2005, now Pat. No. 7,984,730.

(60) Provisional application No. 60/641,909, filed on Jan. 5, 2005, provisional application No. 60/607,113, filed on Sep. 3, 2004.

(51) Int. Cl.
| | | |
|---|---|---|
| *F16K 11/083* | (2006.01) | |
| *F16K 11/085* | (2006.01) | |
| *F16K 27/06* | (2006.01) | |
| *F16K 31/60* | (2006.01) | |
| *A61M 39/04* | (2006.01) | |

(52) U.S. Cl.
CPC ........ *F16K 11/0853* (2013.01); *F16K 27/062* (2013.01); *F16K 27/065* (2013.01); *F16K 31/602* (2013.01); *A61M 39/045* (2013.01); *A61M 2039/229* (2013.01); *Y10T 137/4252* (2015.04); *Y10T 137/86863* (2015.04); *Y10T 137/86871* (2015.04); *Y10T 137/87676* (2015.04)

(56) References Cited

U.S. PATENT DOCUMENTS

| | | |
|---|---|---|
| 3,780,736 A | 12/1973 | Chen |
| 3,834,372 A | 9/1974 | Turney |
| 4,146,055 A | 3/1979 | Ryder |
| 4,397,335 A | 8/1983 | Doblar |
| 4,608,996 A | 9/1986 | Brown |
| 4,654,027 A | 3/1987 | Dragan |
| 4,967,797 A | 11/1990 | Manska |
| 5,002,066 A | 3/1991 | Simpson |
| 5,105,853 A | 4/1992 | Lie |
| 5,135,026 A | 8/1992 | Manska |
| 5,340,364 A | 8/1994 | Ghelli |
| 5,340,634 A | 8/1994 | Adams |
| 5,466,228 A | 11/1995 | Evans |
| 5,549,651 A | 8/1996 | Lynn |
| 5,578,016 A | 11/1996 | Zinger |
| 6,036,171 A | 3/2000 | Weinheimer |
| 6,089,541 A | 7/2000 | Weinheimer |
| 6,238,372 B1 | 5/2001 | Zinger |
| RE37,357 E | 9/2001 | Lynn |
| 6,651,956 B2 | 11/2003 | Miller |
| 6,780,736 B1 | 8/2004 | Holmes |
| 7,232,428 B1 | 6/2007 | Inukai |
| 7,695,445 B2 | 4/2010 | Yuki |
| 7,806,874 B2 | 10/2010 | Funamura |
| 7,963,951 B2 | 6/2011 | Kitani |
| 7,984,730 B2 | 7/2011 | Ziv |
| 8,534,321 B2 | 9/2013 | Ziv |
| 2004/0210162 A1 | 10/2004 | Wyatt |
| 2011/0308651 A1 | 12/2011 | Ziv |

FOREIGN PATENT DOCUMENTS

| | | | | |
|---|---|---|---|---|
| EP | 1426604 B1 | | 5/2010 | |
| JP | 11-342209 A | | 12/1999 | |
| JP | H11342209 A | * | 12/1999 | ............ A61M 39/00 |
| JP | 2002-153562 A | | 5/2002 | |
| JP | 2003-159336 A | | 6/2003 | |
| JP | 5092147 B2 | | 12/2012 | |
| JP | 5415073 B2 | | 11/2013 | |
| JP | 5415073 B2 | | 2/2014 | |
| WO | WO 01/39826 | * | 6/2001 | ............ A61M 39/00 |
| WO | WO2006025054 A3 | | 9/2006 | |
| WO | 2007033319 | | 3/2007 | |

OTHER PUBLICATIONS

An English translation of Office Action for Japanese Application No. 2011-202066 dated Nov. 12, 2013.

An English Translation of an Office Action dated Feb. 5, 2013 which issued during the prosecution of Japanese Patent Application No. 2011-202066.

An Office Action together with its English Translation dated May 17, 2011 which issued during the prosecution of Japanese Patent Application No. 2007-529136.

An Office Action dated May 8, 2012, which issued during the prosecution of European Patent Application No. 05775471.5.

An Office Action dated Sep. 13, 2012, which issued during the prosecution of Canadian Patent Application No. 2,578,989.

U.S. Appl. No. 60/607,113, filed Sep. 3, 2004.

U.S. Appl. No. 60/641,909, filed Jan. 5, 2005.

A Restriction Requirement dated Feb. 5, 2013, which issued during the prosecution of U.S. Appl. No. 13/167,871.

A Notice of Allowance dated Apr. 16, 2013, which issued during the prosecution of U.S. Appl. No. 13/167,871.

* cited by examiner

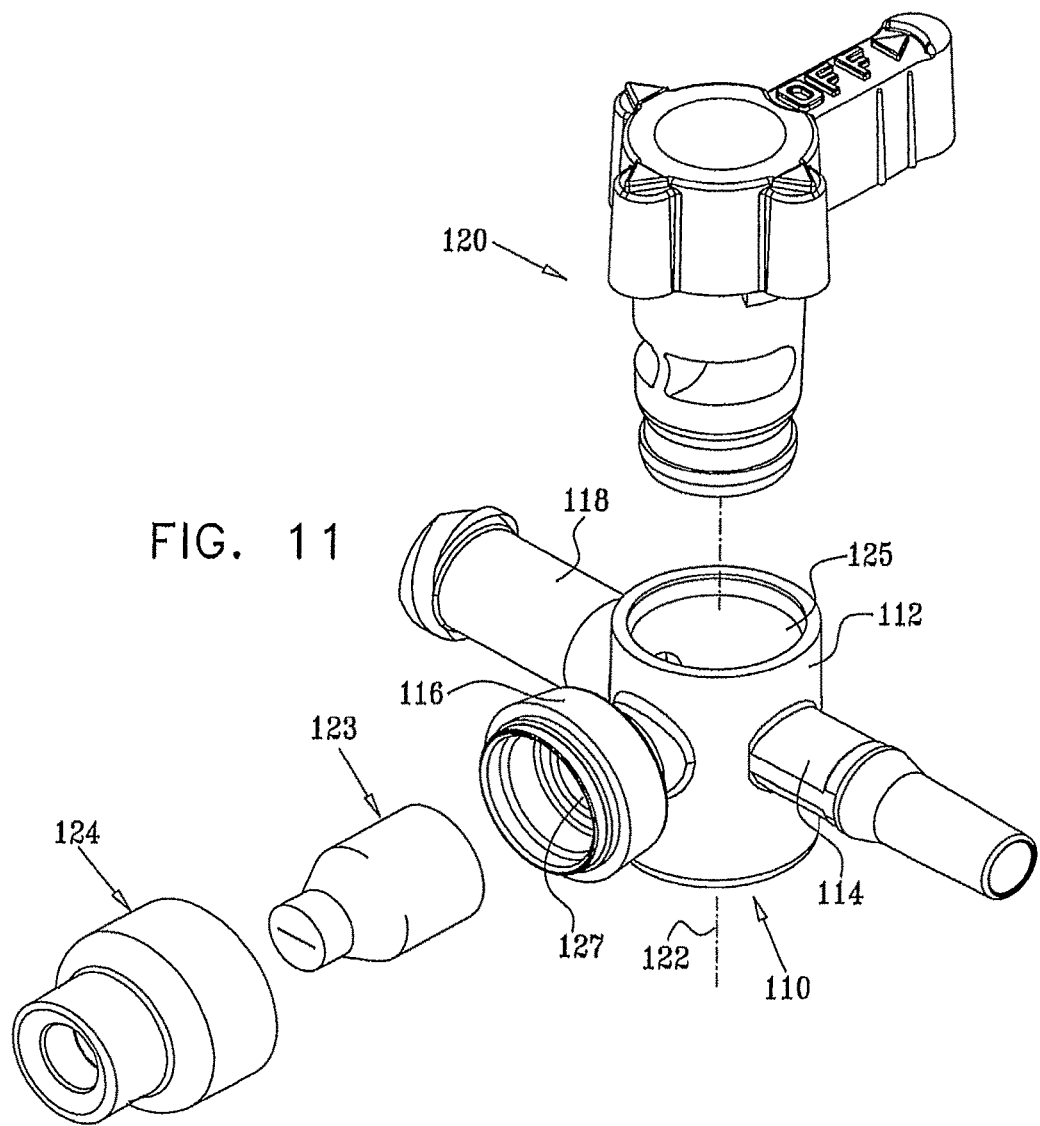

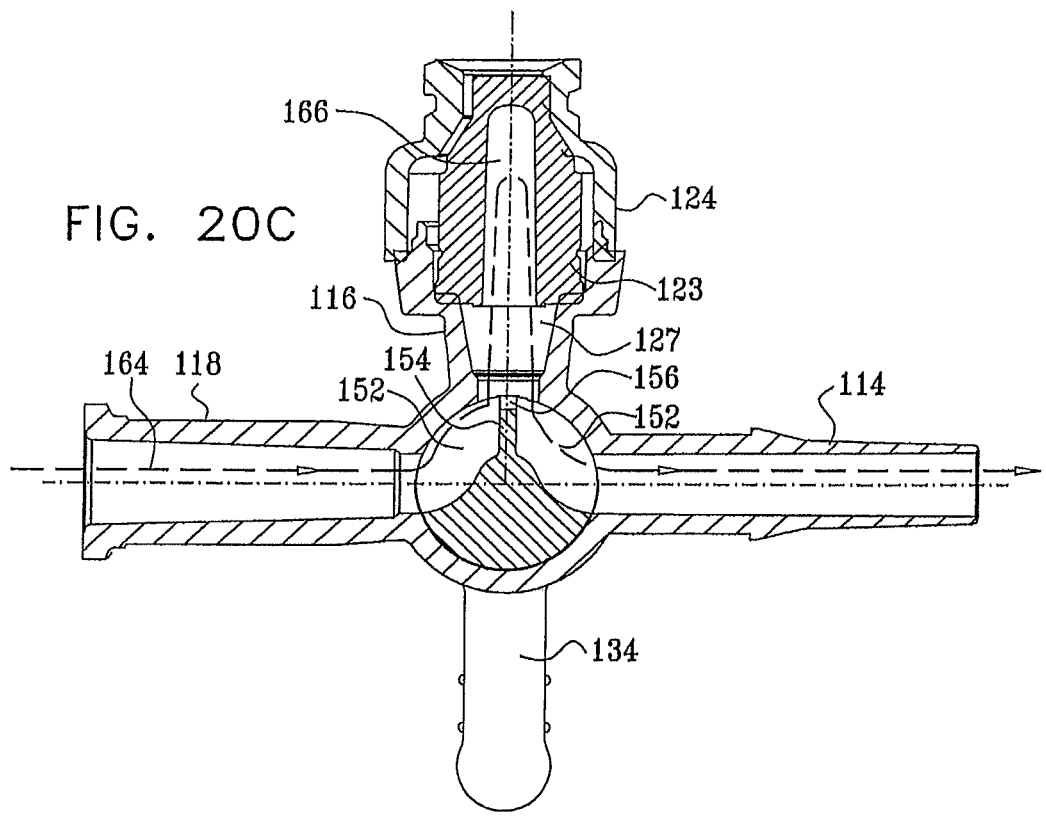
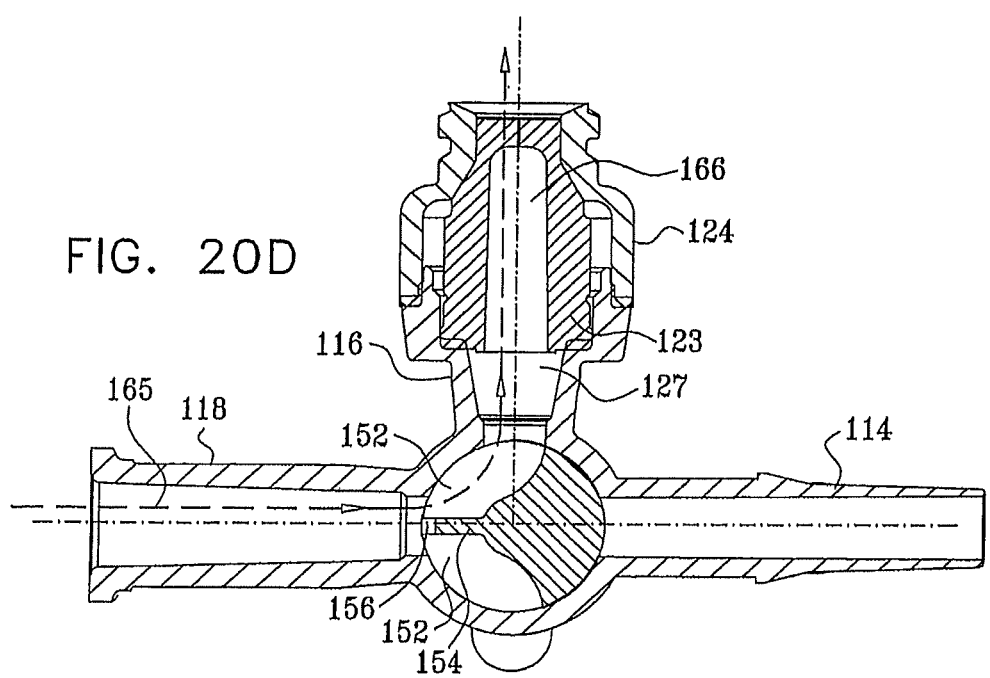

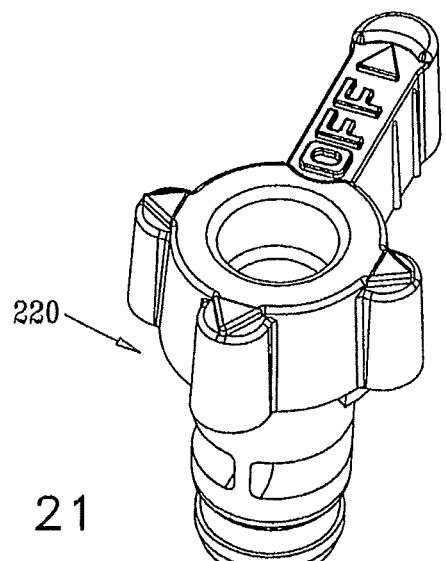
FIG. 21
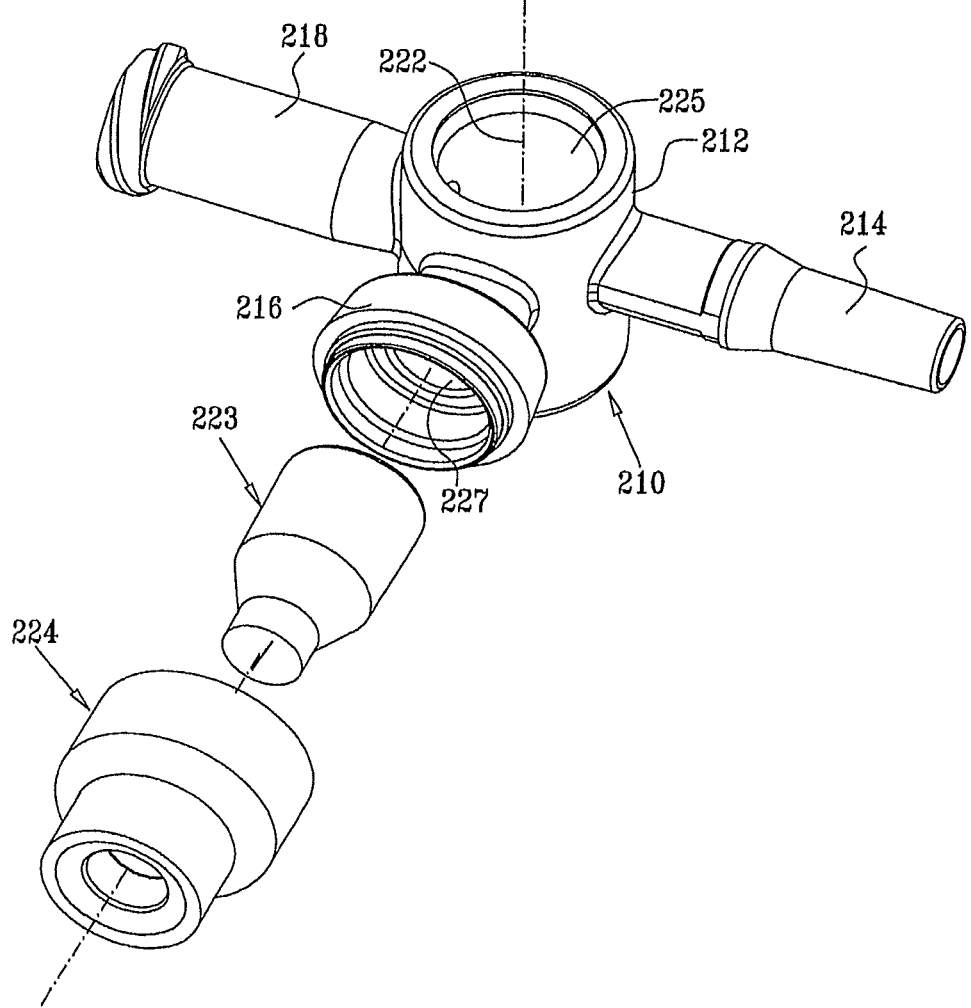

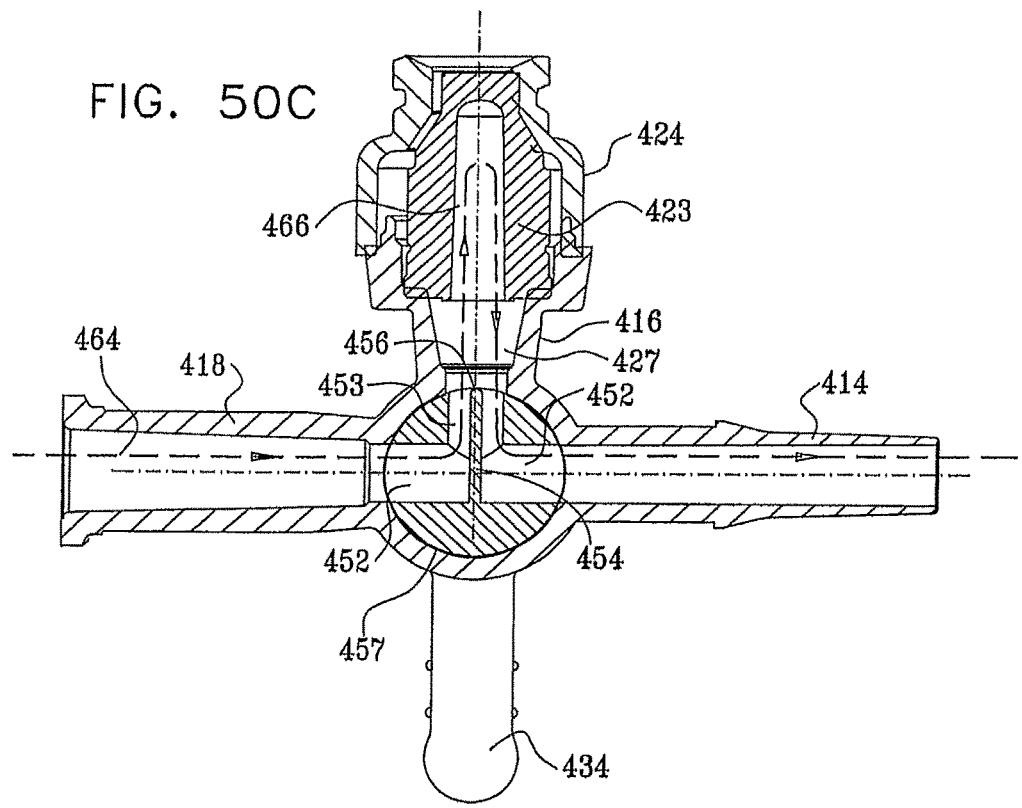
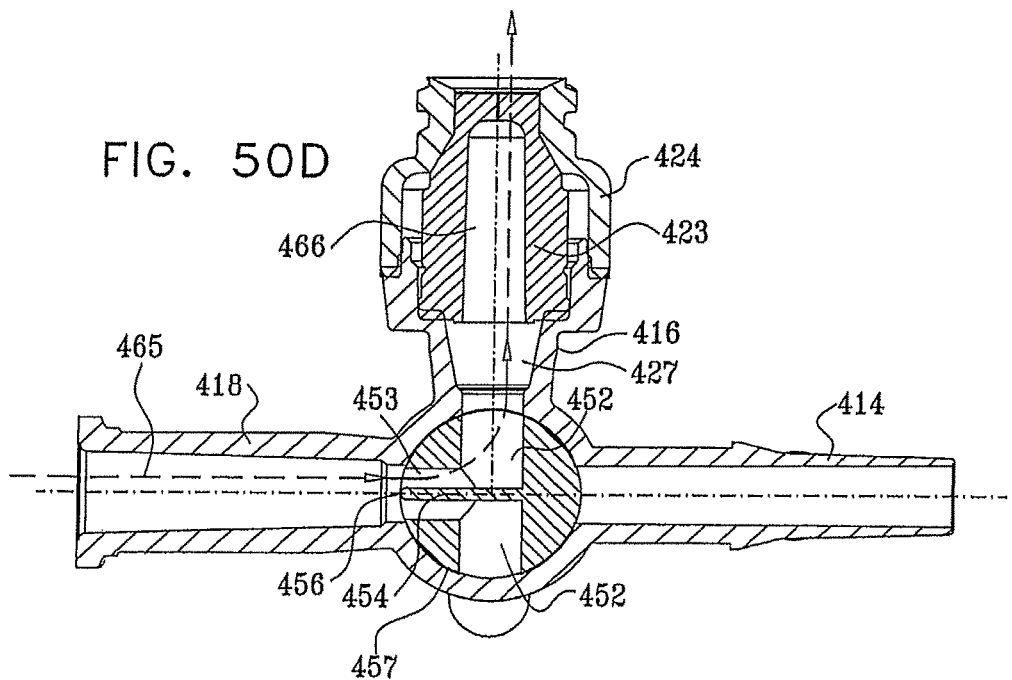

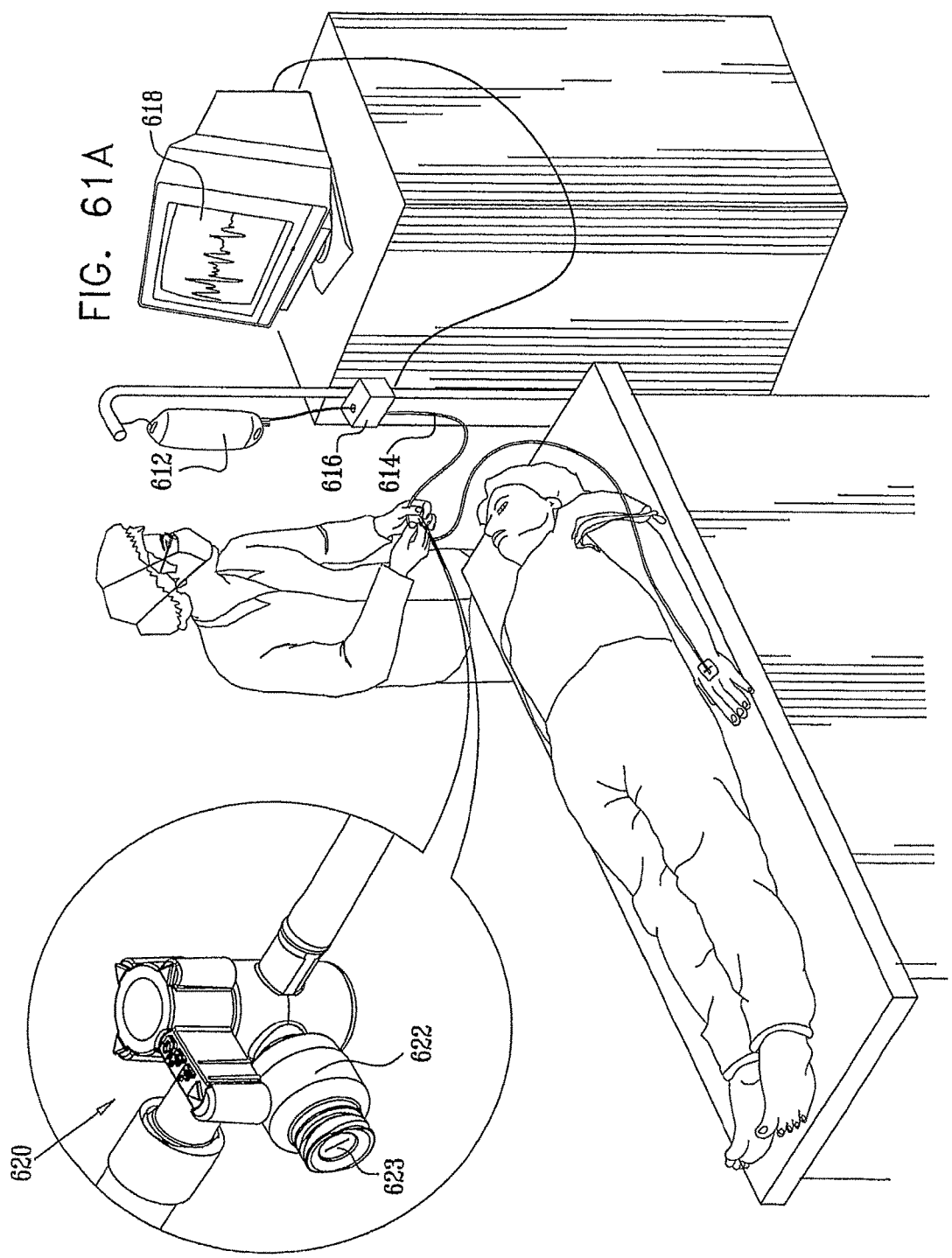

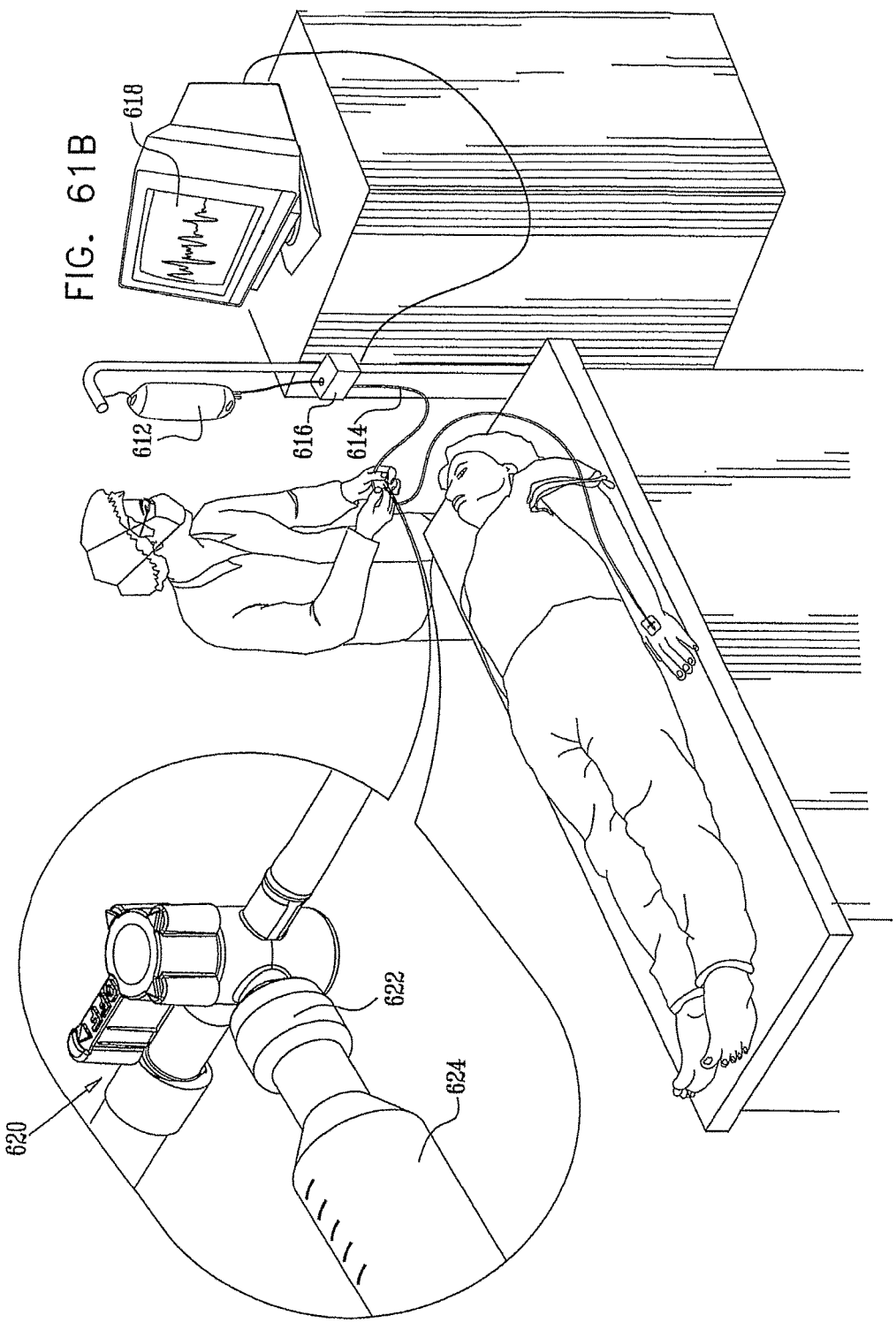

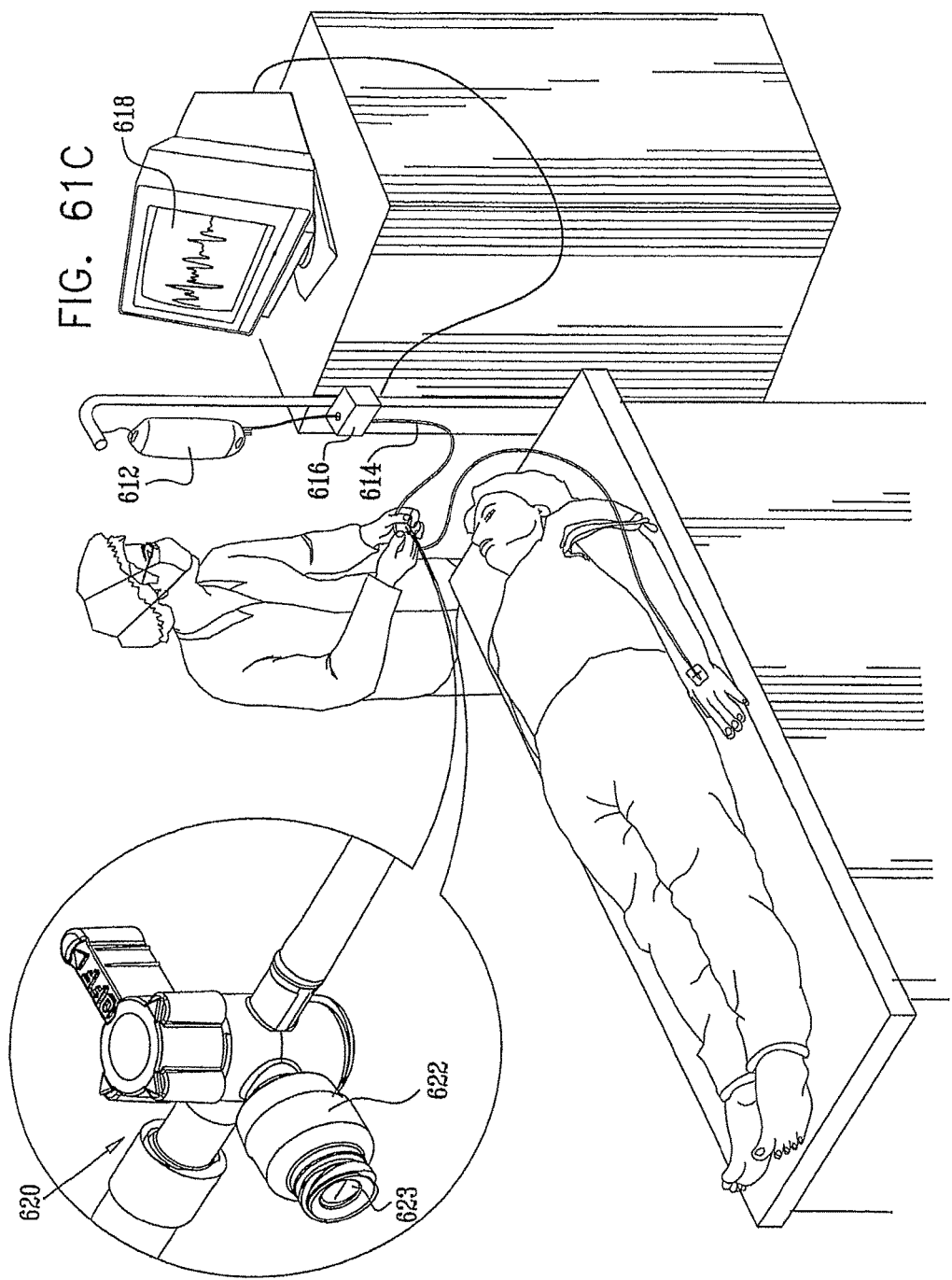

STOPCOCK

REFERENCE TO RELATED APPLICATIONS

This application is a continuation of U.S. patent application Ser. No. 13/937,053, filed Jul. 8, 2013, entitled "STOPCOCK", which is a divisional application of U.S. patent application Ser. No. 13/167,871, now U.S. Pat. No. 8,534,321, filed Jun. 24, 2011, entitled "STOPCOCK", which is a continuation of U.S. patent application Ser. No. 11/574,618, now U.S. Pat. No. 7,984,730, filed Apr. 20, 2007, entitled "STOPCOCK", which is a National Phase Application of PCT/IL2005/000925, filed Aug. 29, 2005, entitled "STOPCOCK", which claims priority of U.S. Provisional Patent Application No. 60/607,113, filed Sep. 2, 2004, entitled "CLOSED STOPCOCK" and to U.S. Provisional Patent Application No. 60/641,909, filed Jan. 5, 2005, entitled "CLOSED STOPCOCK FOR ARTERIAL MONITORING", the disclosures of all of which are hereby incorporated by reference.

FIELD OF THE INVENTION

The present invention relates to stopcocks generally, and more specifically to swabbable stopcocks.

BACKGROUND OF THE INVENTION

The following publications are believed to represent the current state of the art: U.S. Pat. No. 5,549,651, RE 37,357 and U.S. Pat. No. 6,238,372 and U.S. Patent application 2004/0210162.

SUMMARY OF THE INVENTION

The present invention seeks to provide an improved swabbable stopcock device.

There is thus provided in accordance with a preferred embodiment of the present invention a stopcock including a housing element defining at least first, second and third ports, a handle element which is selectably positionable relative to the housing element, at least one fluid passageway communicating between at least two of the at least first, second and third ports, the at least one fluid passageway being selectably defined by at least one of the housing element and the handle element, the at least one fluid passageway being configured for enabling flushing an internal volume of at least one of the first, second and third ports by a fluid flow which does not flow entirely through the port whose internal volume is being flushed.

Preferably, the handle element and the housing element are arrangeable in multiple mutual positions wherein the at least one fluid passageway is configured for enabling flushing the internal volume of at least one of the first, second and third ports when the housing element and the handle element are in at least one of the multiple mutual positions.

Preferably, the stopcock also includes at least one valve, which is associated with at least one of the first, second and third ports. Additionally, the valve includes an elastomeric element and the at least one fluid passageway is configured for providing a fluid flow which is sealed from the elastomeric element when the housing element and the handle are in another one of the mutual positions.

Additionally, the at least one fluid passageway is defined by a shaft portion of the handle element.

Preferably, the stopcock also includes a fluid flow guide associated with the at least one fluid passageway for enabling flushing of the internal volume of the at least one of the first, second and third ports when the housing element and the handle element are in the at least one of the mutual positions by the fluid flow which does not flow entirely through the port whose internal volume is being flushed.

Preferably, the at least one fluid passageway is defined by at least one recess formed on a peripheral surface of the handle element. Alternatively, the at least one fluid passageway is defined by at least one bore formed within the shaft portion of the handle element. Additionally or alternatively, the fluid flow guide extends radially and partially bifurcates the at least one fluid passageway.

Preferably, the fluid flow guide includes a concave outward facing edge. Alternatively, the fluid flow guide includes an outward facing edge adapted to prevent flow of liquid when the fluid flow guide is not located opposite at least one of the ports. Additionally, at least one of the at least one port is bifurcated by the fluid flow guide.

Preferably, the housing element includes a side recess located within a central bore of the housing element.

There is also provided in accordance with another preferred embodiment of the present invention an arterial monitoring set including an arterial line adapted to be connected at a first end thereof to a source of liquid under pressure and at a second end thereof to an artery of a patient, a pressure transducer disposed along the arterial line for sensing liquid pressure therein, a stopcock disposed along the arterial line, the stopcock including a housing element defining at least first, second and third ports, a handle element which is selectably positionable relative to the housing element, at least one fluid passageway communicating between at least two of the at least first, second and third ports, the at least one fluid passageway being selectably defined by at least one of the housing element and the handle element, the at least one fluid passageway being configured for enabling flushing an internal volume of at least one of the first, second and third ports by a fluid flow which flows through the arterial line to the patient.

Preferably, the handle element and the housing element are arrangeable in multiple mutual positions and the at least one fluid passageway is configured for enabling flushing the internal volume of at least one of the first, second and third ports when the housing element and the handle element are in at least one of the multiple mutual positions.

Preferably, the stopcock includes at least one valve, which is associated with at least one of the first, second and third ports. Additionally, the valve includes an elastomeric element and the at least one fluid passageway is configured for providing a fluid flow which is sealed from the elastomeric element when the housing element and the handle are in another one of the mutual positions.

Preferably, the at least one fluid passageway is defined by a shaft portion of the handle element.

Additionally, the arterial monitoring set also includes a fluid flow guide associated with the at least one fluid passageway for enabling flushing of the internal volume of at least one of the first, second and third ports when the housing element and the handle element are in at least one of the mutual positions by the fluid flow which flows through the arterial line to the patient.

Preferably, the at least one fluid passageway is defined by at least one recess formed on a peripheral surface of the handle element. Alternatively, the at least one fluid passageway is defined by at least one bore formed within the shaft portion of the handle element. Additionally or alternatively, the fluid flow guide extends radially and partially bifurcates the at least one fluid passageway.

Preferably, the fluid flow guide includes a concave outward facing edge. Alternatively, the fluid flow guide includes an outward facing edge to prevent flow of liquid when the fluid flow guide is not located opposite at least one of the ports.

Preferably, at least one of the at least one port is bifurcated by the fluid flow guide. Alternatively or additionally, the housing element includes a side recess located within a central bore of the housing element.

There is further provided in accordance with yet another preferred embodiment of the present invention a method of providing fluid communication with the circulatory system of a patient including providing a stopcock including a housing element defining at least first, second and third ports, a handle element which is selectably positionable relative to the housing element, at least one fluid passageway communicating between at least two of the at least first, second and third ports, the at least one fluid passageway being selectably defined by at least one of the housing element and the handle element, providing a flow of a first fluid through the stopcock in communication with the circulatory system of the patient when the handle element and the housing element are in a first mutual position, and providing a flow of a second fluid through the stopcock in communication with the circulatory system of the patient when the handle element and the housing element are in a second mutual position, thereby flushing an internal volume of at least one of the first, second and third ports by the second fluid which does not flow entirely through the port whose internal volume is being flushed.

Preferably, the flow of the first fluid passes through the stopcock from the second port to the third port and the flow of the second fluid passes through the stopcock from the first port to the third port. Alternatively, the flow of the first fluid passes through the stopcock from the third port to the second port and the flow of the second fluid passes through the stopcock from the third port to the first port.

Preferably, the stopcock also includes at least one valve, which is associated with at least one of the first, second and third ports. Additionally, the valve includes an elastomeric element and the at least one fluid passageway is configured for providing a fluid flow which is sealed from the elastomeric element when the housing element and the handle are in a third mutual position.

BRIEF DESCRIPTION OF THE DRAWINGS

The present invention will be understood and appreciated more fully from the following detailed description, taken in conjunction with the drawings in which:

FIG. 11 is a simplified exploded view illustration of a stopcock constructed and operative in accordance with another preferred embodiment of the present invention;

FIGS. 20A, 20B, 20C and 20D are sectional illustrations taken along section lines XXA-XXA, XXB-XXB, XXC-XXC and XXD-XXD in FIGS. 19A, 19B, 19C and 19D respectively;

FIG. 21 is a simplified exploded view illustration of a stopcock constructed and operative in accordance with an additional preferred embodiment of the present invention;

FIGS. 50A, 50B, 50C and 50D are sectional illustrations taken along section lines LA-LA, LB-LB, LC-LC and LD-LD in FIGS. 49A, 49B, 49C and 49D respectively;

FIGS. 61A, 61B and 61C are simplified pictorial illustrations of an arterial monitoring set constructed and operative in accordance with a preferred embodiment of the present invention in various operative orientations.

DETAILED DESCRIPTION OF PREFERRED EMBODIMENTS

Figure 1:
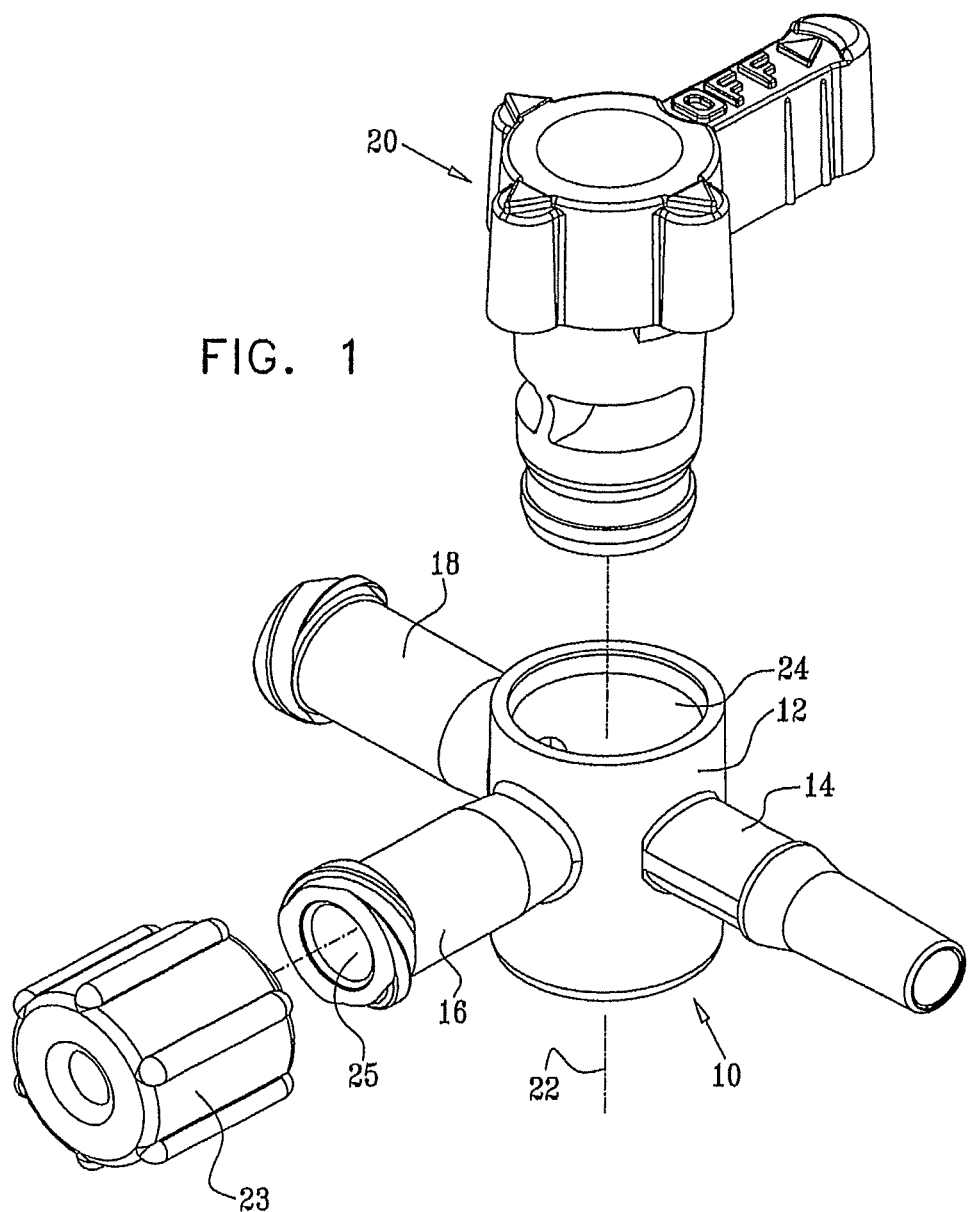
FIG. 1 is a simplified exploded view illustration of a stopcock constructed and operative in accordance with a preferred embodiment of the present invention.

Reference is now made to FIG. 1, which is an exploded view illustration of a stopcock, constructed and operative in accordance with a preferred embodiment of the present invention. As seen in FIG. 1, the stopcock comprises a housing element 10 including a main tubular portion 12 and three side ports, designated by reference numerals 14, 16 and 18 respectively. A handle element 20 is arranged to be seated within main tubular portion 12 of housing element 10. A typical threaded plug 23 is adapted to be connected to side port 16.

Figure 2:
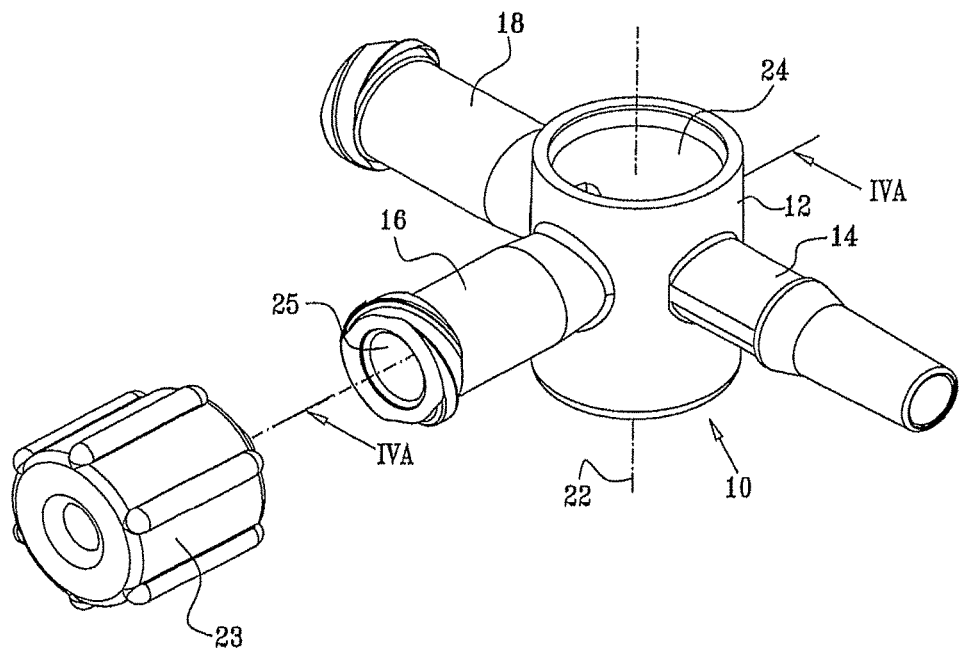
FIGS. 2 and 3 are simplified pictorial illustrations of a housing element, and a threaded plug, which form part of the stopcock of FIG. 1 taken in two different directions.
Figure 3:
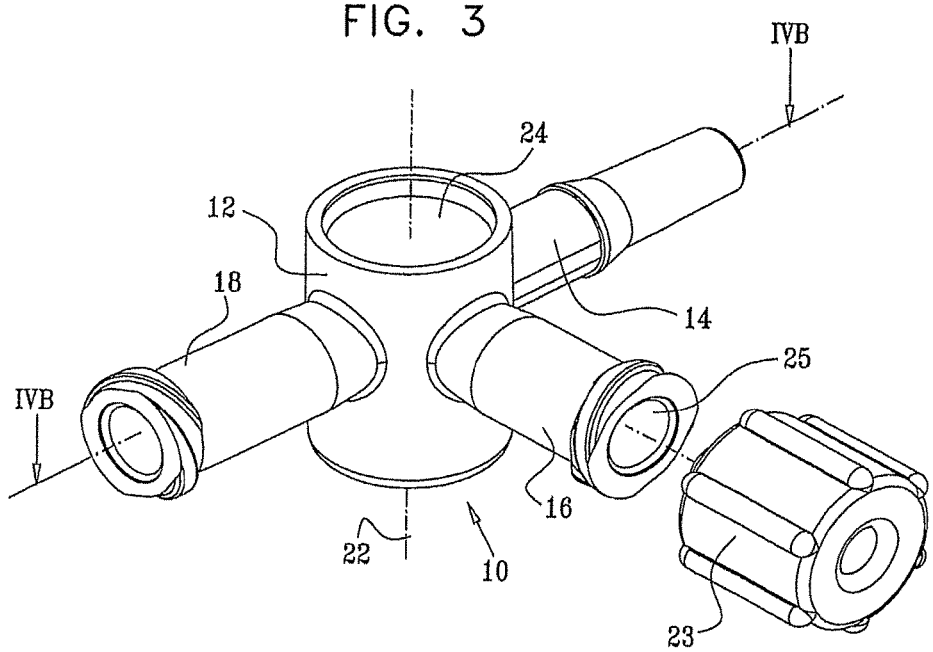
Figure 4A:
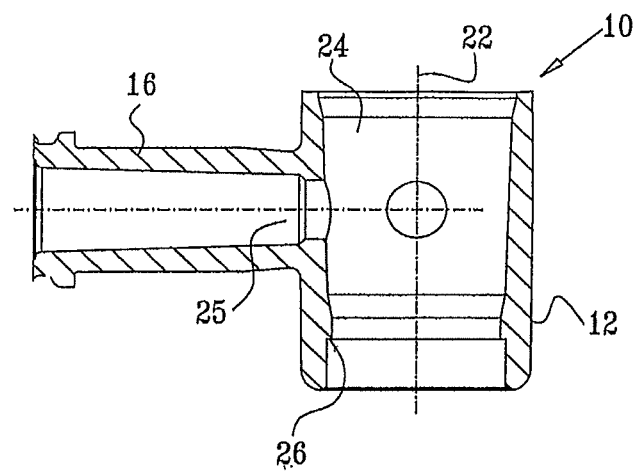
FIGS. 4A and 4B are sectional illustrations taken along section lines IVA-IVA and IVB-IVB in FIGS. 2 and 3, respectively.
Figure 4B:
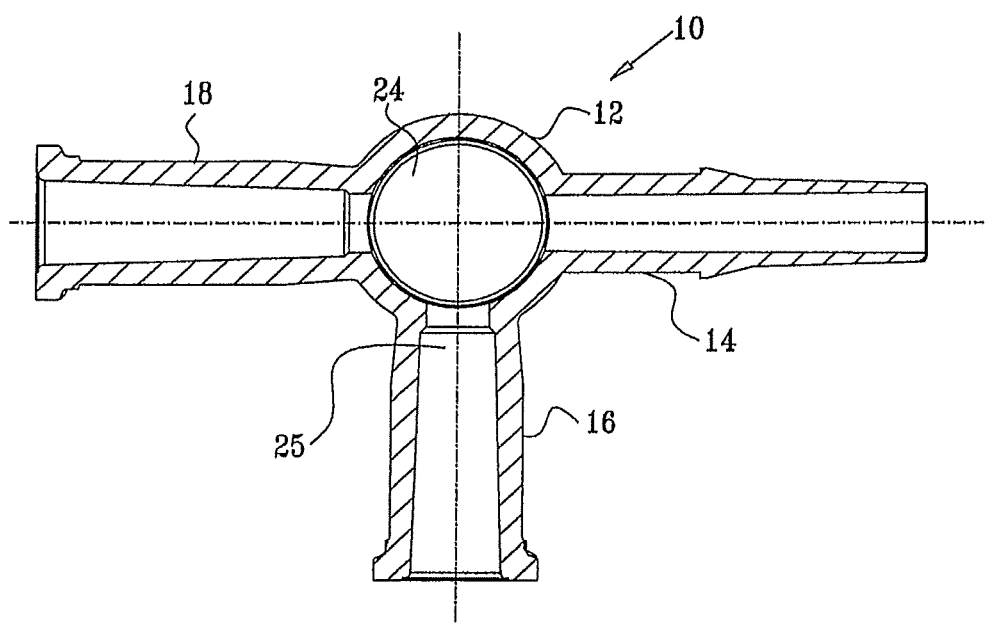
Figure 5A:
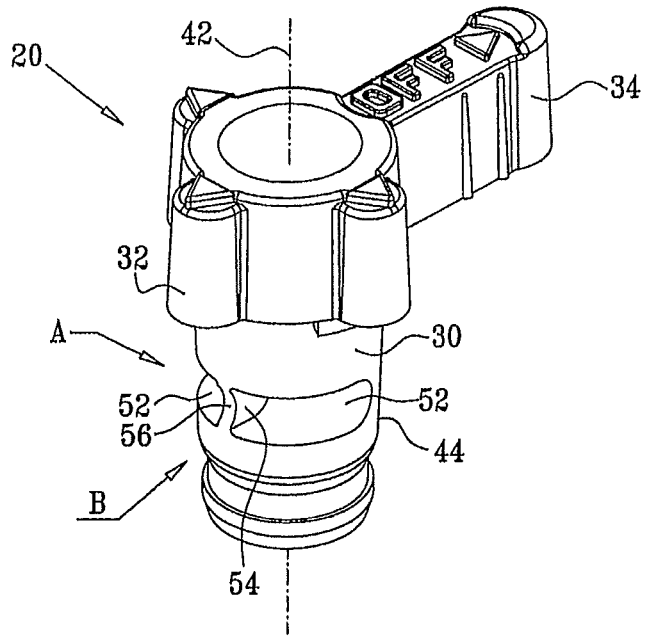
FIGS. 5A and 5B are simplified pictorial illustrations of a handle element which forms part of the stopcock of FIG. 1 in two orientations.
Figure 5B:
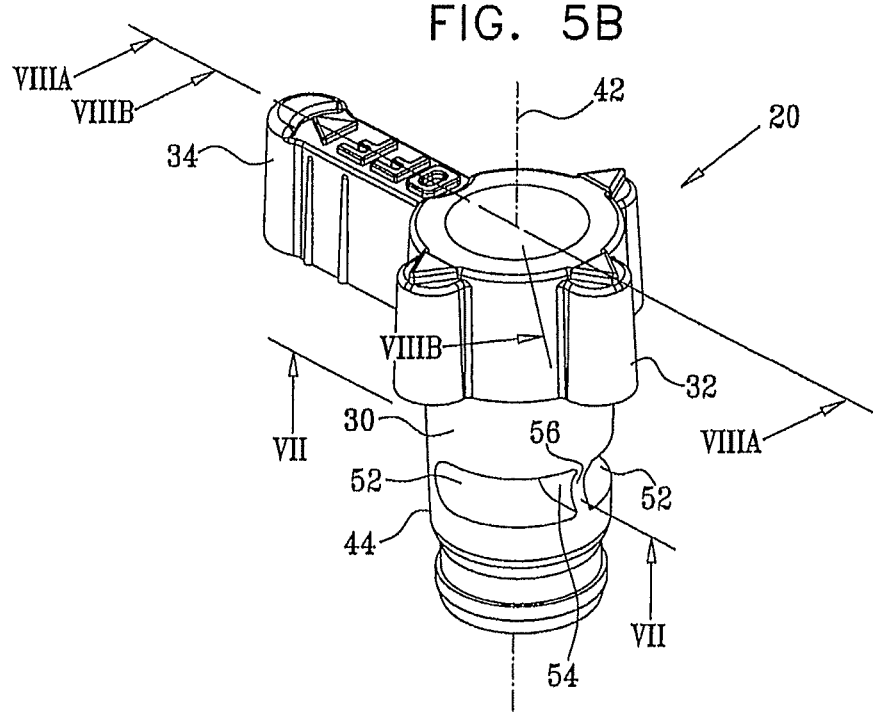
Figure 6A:
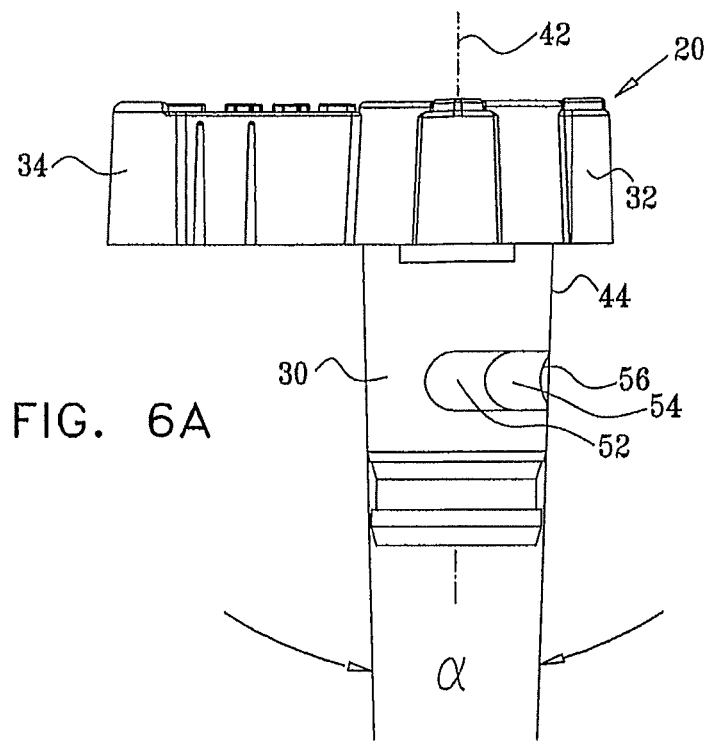
FIGS. 6A and 6B are simplified plan view illustrations of the handle element of FIGS. 5A and 5B taken along respective directions A and B in FIG. 5A.
Figure 6B:
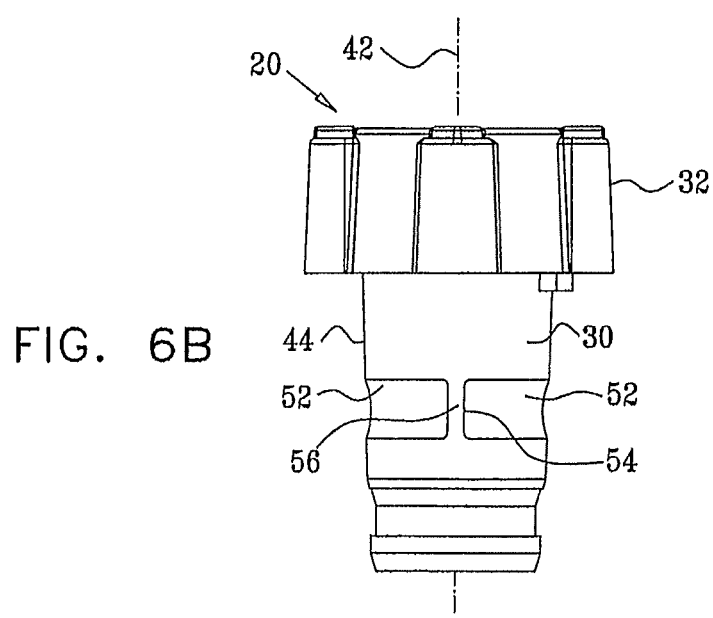
Figure 7:
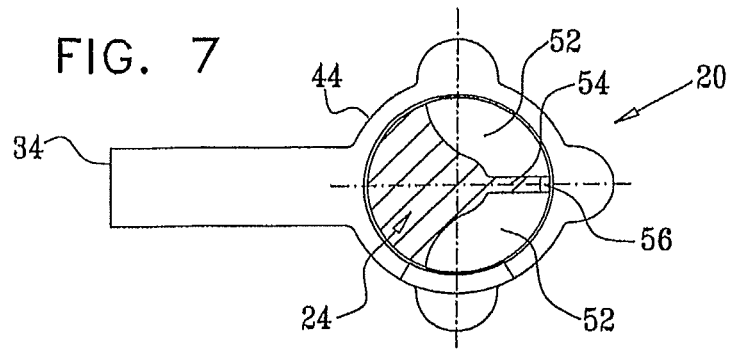
FIGS. 7, 8A and 8B are sectional illustrations taken along section lines VII-VII, VIIIA-VIIIA and VIIIB-VIIIB in FIG. 5B.
Figure 8A:
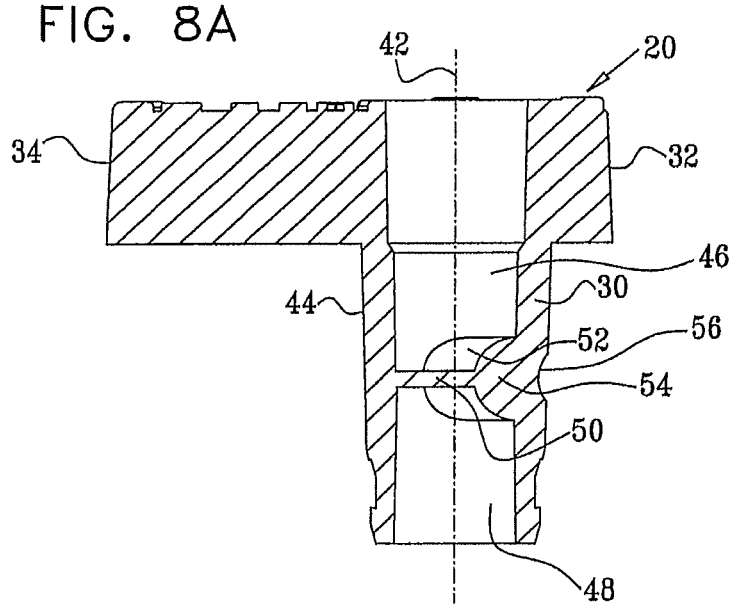
Figure 8B:
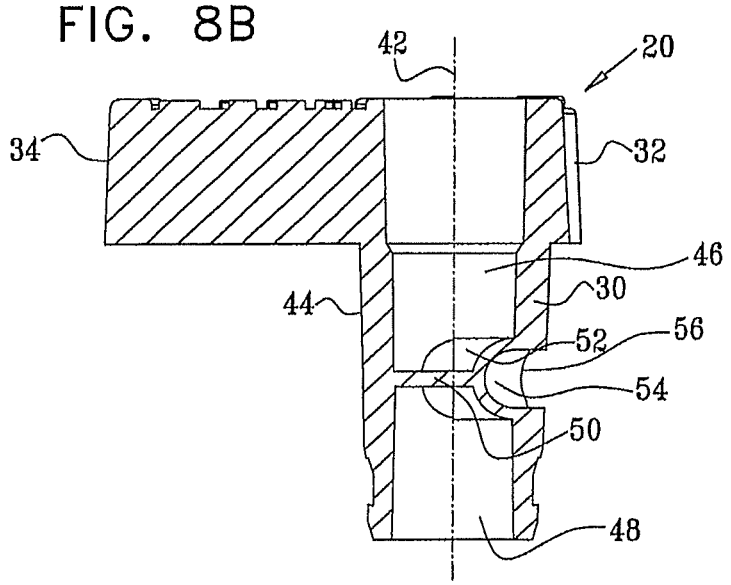

Reference is now made additionally to FIGS. 2 and 3 which are pictorial illustrations of housing element 10 and to FIGS. 4A and 4B which are sectional illustrations thereof. As seen in FIGS. 1-4B, tubular portion 12 of housing element 10 is generally cylindrical, arranged about an axis 22, and has side ports 14, 16 and 18 extending in different directions therefrom, typically separated by 90 degrees about axis 22. Port 14 is preferably a male port which preferably meets luer standard ISO 594-1, while ports 16 and 18 are preferably female ports, which preferably meet luer standard ISO 594-1. Conventional plugs, nuts and covers may be used in association with ports 14, 16 and 18. As seen particularly in FIGS. 1-3, threaded plug 23 is shown arranged for sealing engagement with port 16. Tubular portion 12 includes a central bore 24 having a slightly conical configuration, which is formed with a circumferential undercut 26. Port 16 defines an internal volume 25.

Reference is now made to FIGS. 5A-8B, which illustrate handle element 20. As seen in FIGS. 5A-8B, the handle element includes a shaft portion 30, which is integrally formed with a top portion 32 from which extends a finger-engageable protrusion 34. It is appreciated that any other suitable general configuration of the top portion of the handle element may alternatively be employed.

Shaft portion 30 is generally symmetrical about a shaft axis 42 and has a slightly conical outer surface 44, typically having an angle α (as seen particularly in FIG. 6A) of 3-4 degrees, which corresponds to the slightly conical configuration of central bore 24 for rotatable sealing engagement therewith. As seen particularly in FIGS. 8A and 8B, shaft portion 30 is typically formed with mutually sealed top and bottom cylindrical recesses 46 and 48, which are sealingly separated by a divider 50.

Disposed generally between recesses 46 and 48 and sealed therefrom is a partially peripherally-extending recess 52, selectably defining a fluid flow passageway between selectable ones of side ports 14, 16 and 18 depending on the rotational orientation of the handle element 20 relative to the housing element 10. Preferably extending radially and partially bifurcating the recess 52 is a fluid flow guide 54, which directs the flow of liquid between ports 14 and 18 through the passageway defined by recess 52 into the internal volume 25 of port 16 for flushing thereof, when the handle element 20 is suitably positioned. The radially outward facing edge 56 of fluid flow guide 54 is formed with a concave configuration.

Reference is now made to FIGS. 9A, 9B, 9C, 9D and 9E, which are simplified pictorial illustrations of the stopcock of FIG. 1 in five operative orientations and to FIGS. 10A, 10B, 10C, 10D and 10E, which are sectional illustrations of the stopcock of FIGS. 9A, 9B, 9C, 9D and 9E respectively.

Figure 9A:
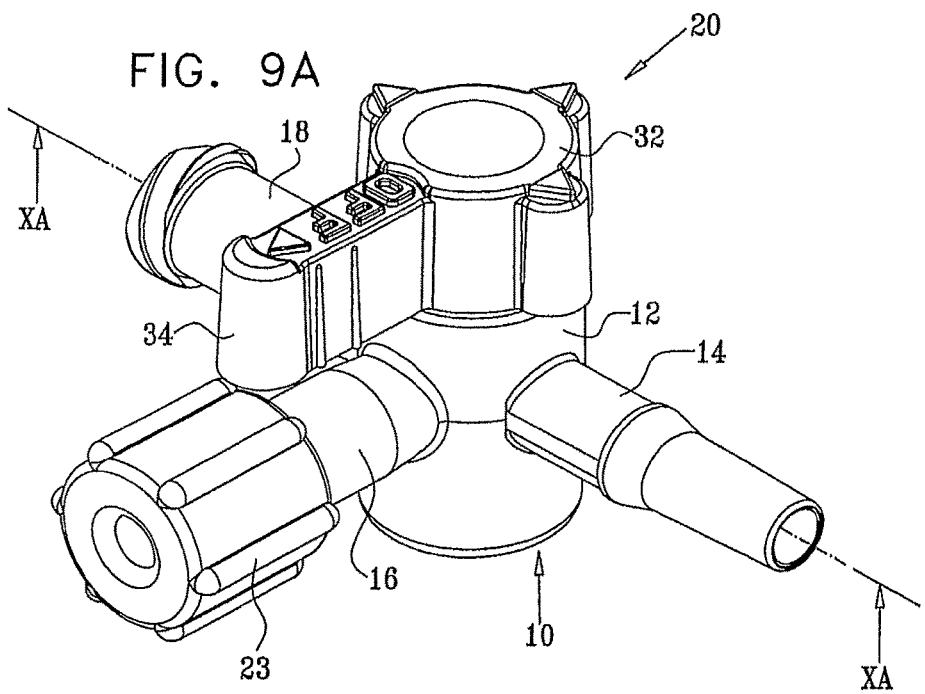
FIGS. 9A, 9B, 9C, 9D and 9E are simplified pictorial illustrations of the stopcock of FIG. 1 in five operative orientations.
Figure 10A:
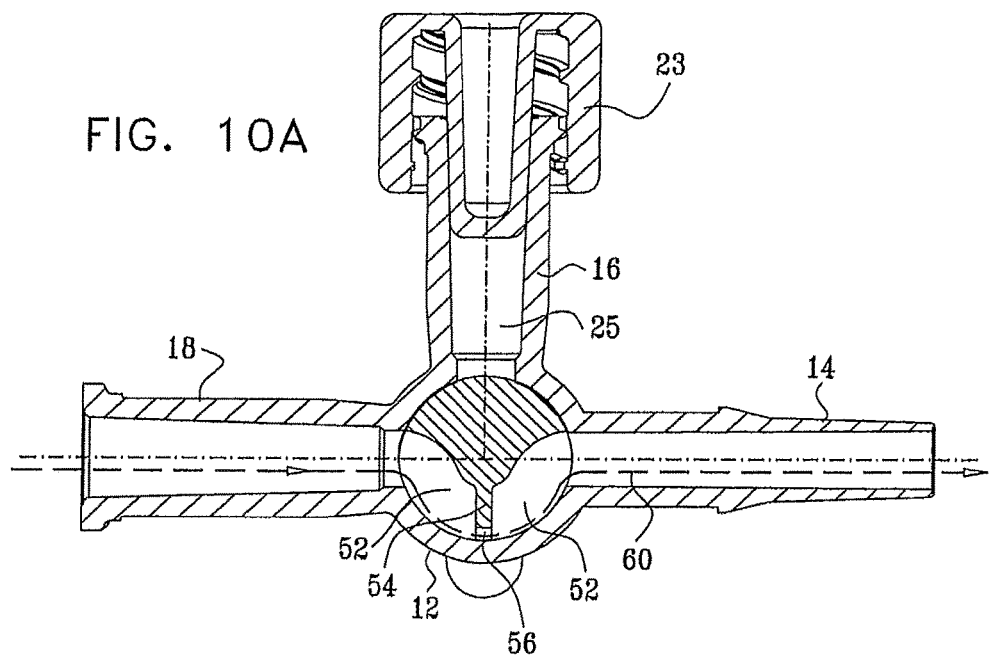
FIGS. 10A, 10B, 10C, 10D and 10E are sectional illustrations taken along section lines XA-XA, XB-XB, XC-XC, XD-XD and XE-XE in FIGS. 9A, 9B, 9C, 9D and 9E respectively.

FIGS. 9A and 10A illustrate a first operating position of the stopcock of FIG. 1 when port 16 is sealed as by threaded plug 23. The user typically connects a source of pressurized fluid, such as an IV set, to port 18 and the liquid flows through port 18 and partially peripherally-extending recess 52 and past the concave edge 56 of fluid flow guide 54 via port 14 to the patient, as indicated by an arrow 60.

Figure 9B:
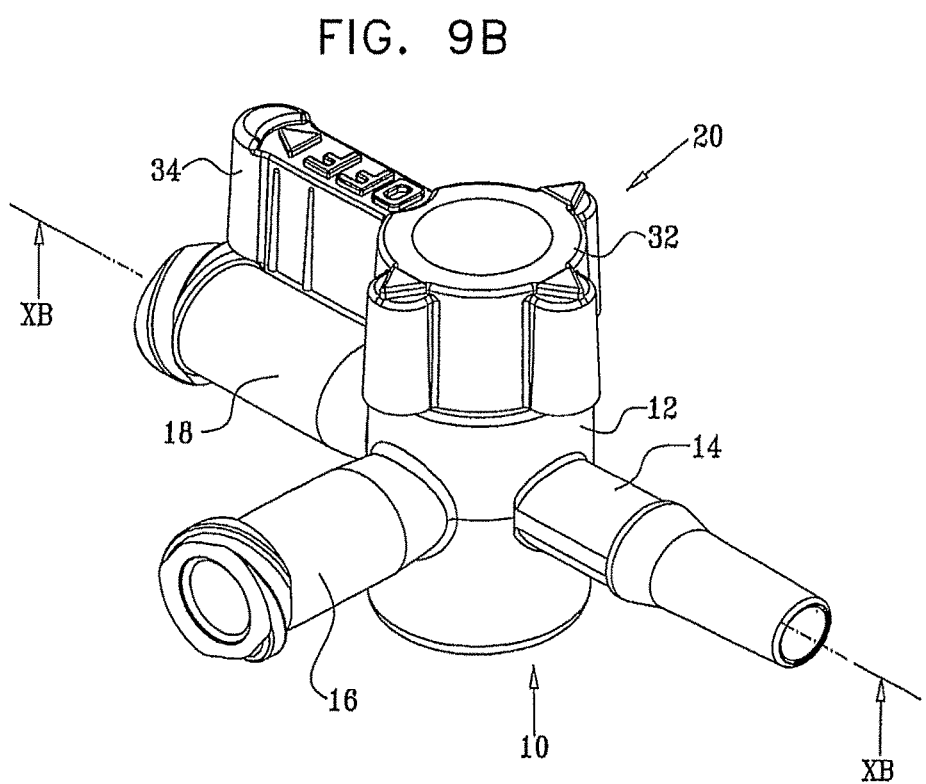
Figure 10B:
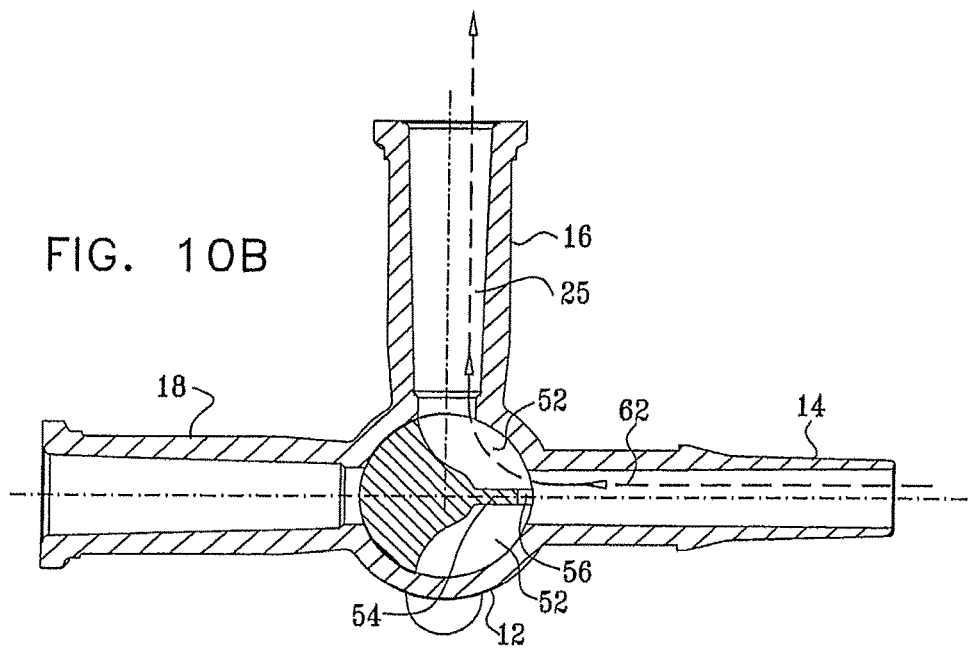

FIGS. 9B and 10B illustrate a second operating position of the stopcock of FIG. 1, which is typically employed for drawing blood or other fluids from the patient. The user typically connects a syringe (not shown) to port 16 and draws blood from the patient through port 14 and partially peripherally-extending recess 52 through port 16 to the syringe, as indicated by an arrow 62. It is appreciated that this operating position may also be used for supplying a medicament to the patient when port 18 is closed, in a flow direction opposite to that indicated by arrow 62.

Figure 9C:
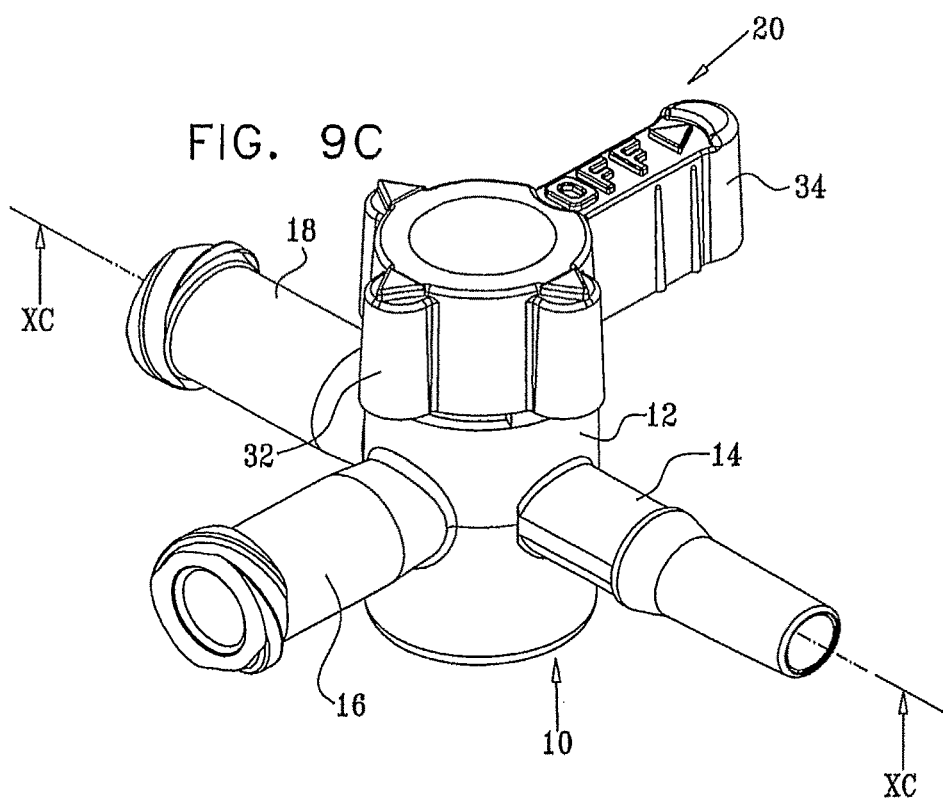
Figure 10C:
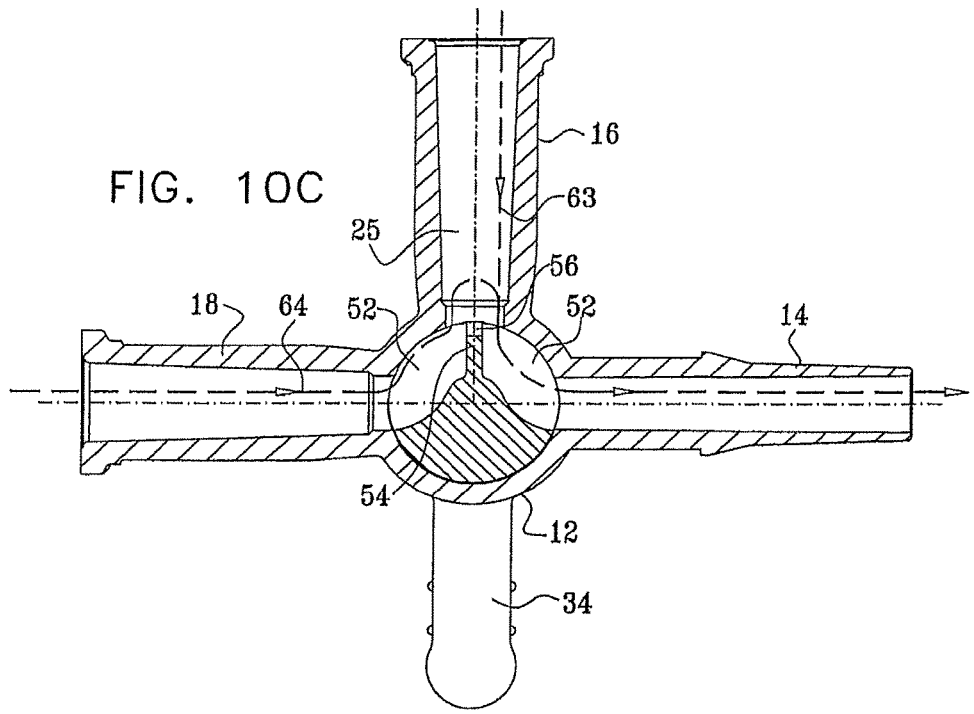

FIGS. 9C and 10C illustrate a third operating position of the stopcock of FIG. 1, which is typically employed for supplying a medicament to the patient when port 16 is open or connected to a secondary line (not shown). A secondary line may be a source of medicament. The medicament flows through port 16 and partially peripherally-extending recess 52 through port 14 to the patient, as indicated by an arrow 63. At the same time, liquid flows via port 18 and partially peripherally-extending recess 52, around fluid flow guide 54, and slightly into the internal volume 25 of port 16, via port 14 to the patient, as indicated by an arrow 64.

Figure 9D:
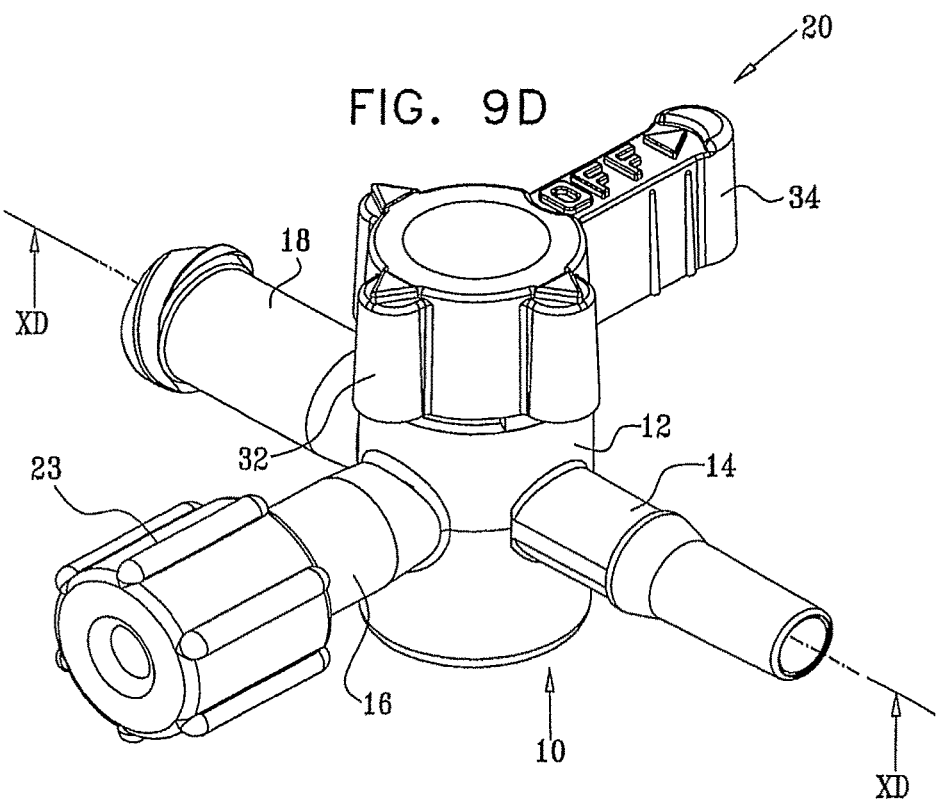
Figure 10D:
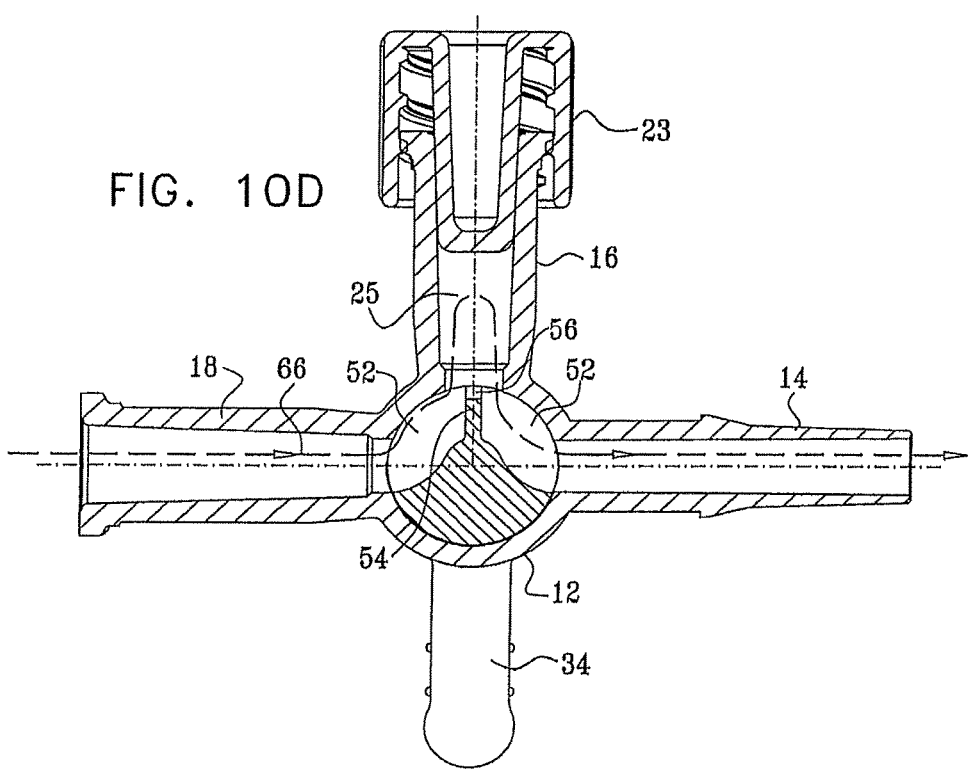

FIGS. 9D and 10D illustrate a fourth operating position of the stopcock of FIG. 1, which is typically employed for supplying a liquid to the patient from port 18 to port 14, when port 16 is sealed as by threaded plug 23. Liquid flows via port 18 and partially peripherally-extending recess 52, around fluid flow guide 54, and into the internal volume 25 of port 16, flushing residual liquid therefrom, via port 14 to the patient, as indicated by an arrow 66.

It is a particular feature of the present invention that the provision of fluid flow guide 54 generally overcomes problems of the presence of residual liquids remaining in the internal volume 25 of port 16. This is important in various therapeutic situations. For example when blood is drawn from the patient through port 16, there remains residual blood in the internal volume 25 of port 16. This blood, if left in internal volume 25 for a period of time, can clot and thus become dangerous if delivered to the patient. In addition, the coagulated blood could occlude the liquid passageway extending through port 16. Various infections could possibly arise as a result of the retained blood.

This feature is also useful when a medicament is supplied to a patient through port 16. If a portion of the medicament remains in the internal volume 25 of port 16, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament, from the internal volume 25 and typically returning it to the patient without requiring the use of extra syringes, the manipulation of the threaded plug 23 and opening the medical set to the atmosphere, which could increase the chance of contamination.

Figure 9E:
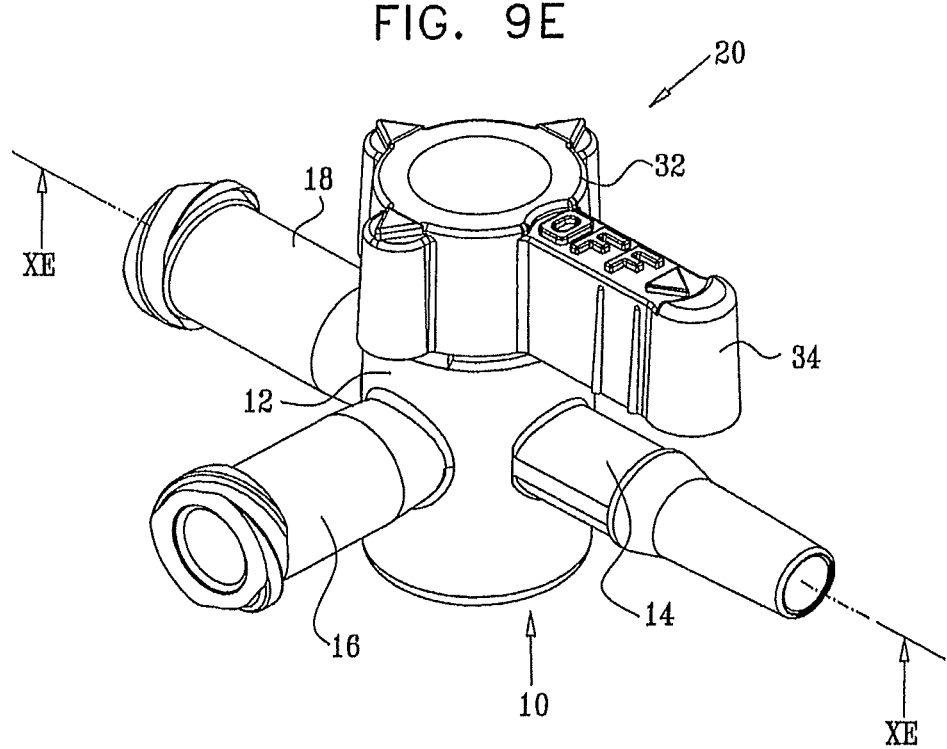
Figure 10E:
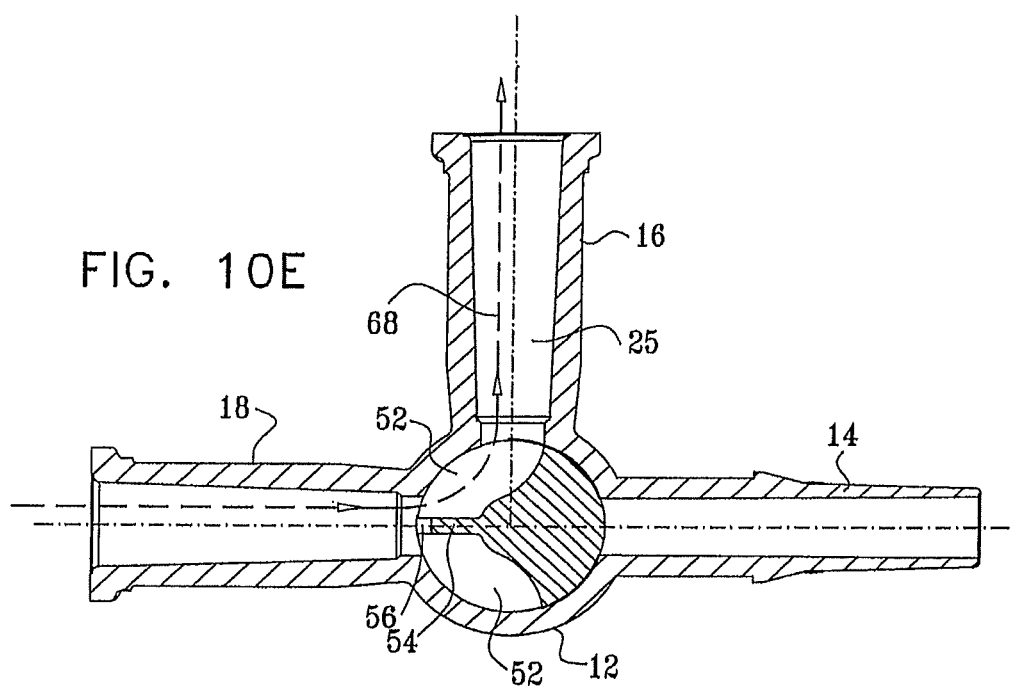

FIGS. 9E and 10E illustrate a fifth operating position of the stopcock of FIG. 1, which may be used for flushing the IV set upstream of the stopcock, when port 16 is open to the atmosphere. Liquid flows via port 18, around fluid flow guide 54 and through partially peripherally-extending recess 52, to the atmosphere via port 16, as indicated by an arrow 68. Alternatively, this operating position may be employed for pushing liquid via the side port 16 and through port 18 in a direction opposite arrow 68, for example when it is desired to mix liquid in the pressure bag.

Reference is now made to FIG. 11, which is an exploded view illustration of a stopcock constructed and operative in accordance with a preferred embodiment of the present invention. As seen in FIG. 11, the stopcock comprises a housing element 110 including a main tubular portion 112 and three side ports, designated by reference numerals 114, 116 and 118 respectively. A handle element 120 is arranged to be seated within main tubular portion 112 of housing element 110.

Figure 12:
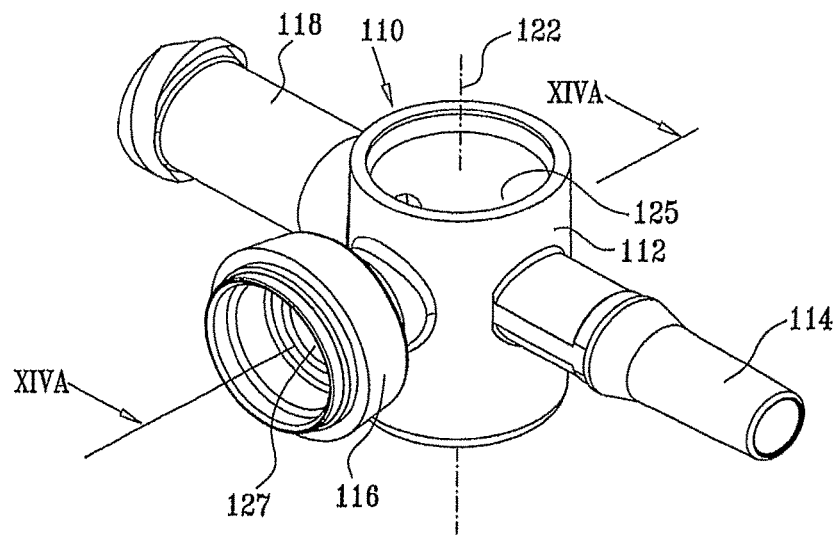
FIGS. 12 and 13 are simplified pictorial illustrations of a housing element, which forms part of the stopcock of FIG. 11 taken in two different directions.
Figure 13:
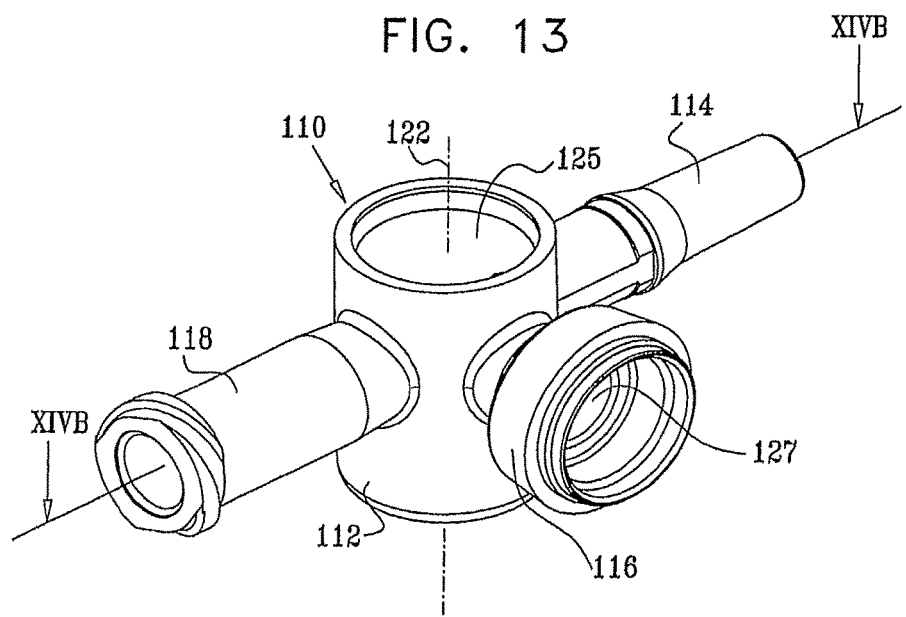
Figure 14A:
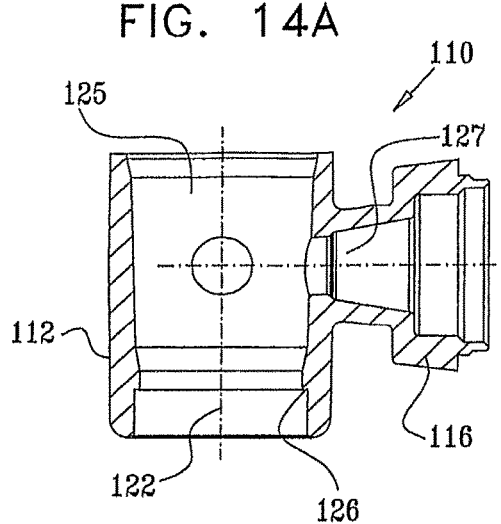
FIGS. 14A and 14B are sectional illustrations taken along section lines XIVA-XIVA and XIVB-XIVB in FIGS. 12 and 13, respectively.
Figure 14B:
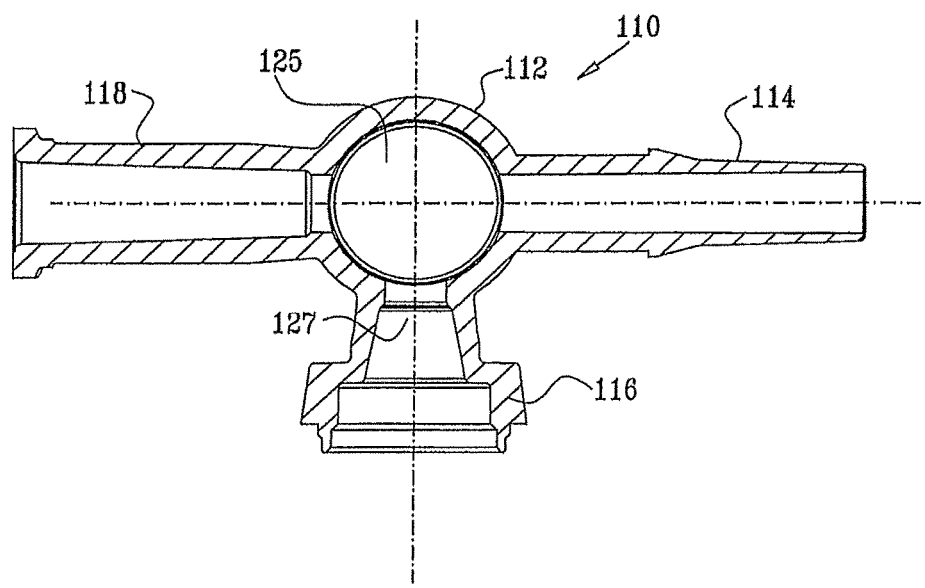
Figure 15A:
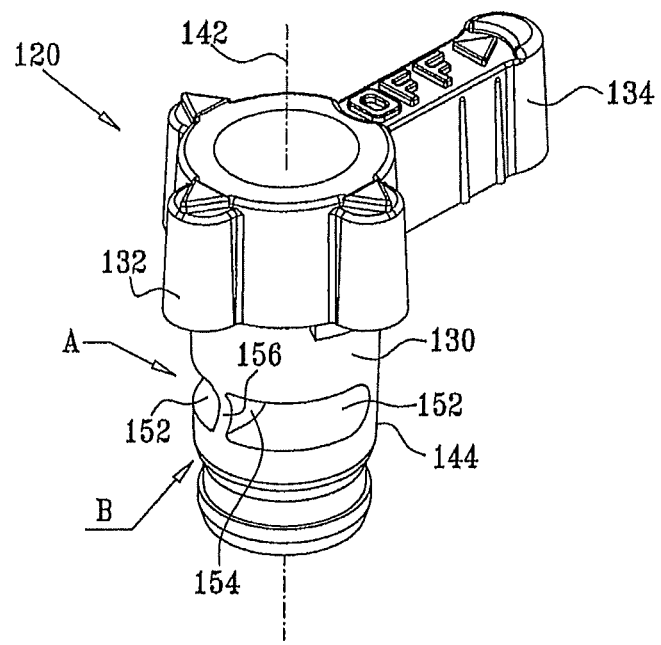
FIGS. 15A and 15B are simplified pictorial illustrations of a handle element which forms part of the stopcock of FIG. 11 in two orientations.
Figure 15B:
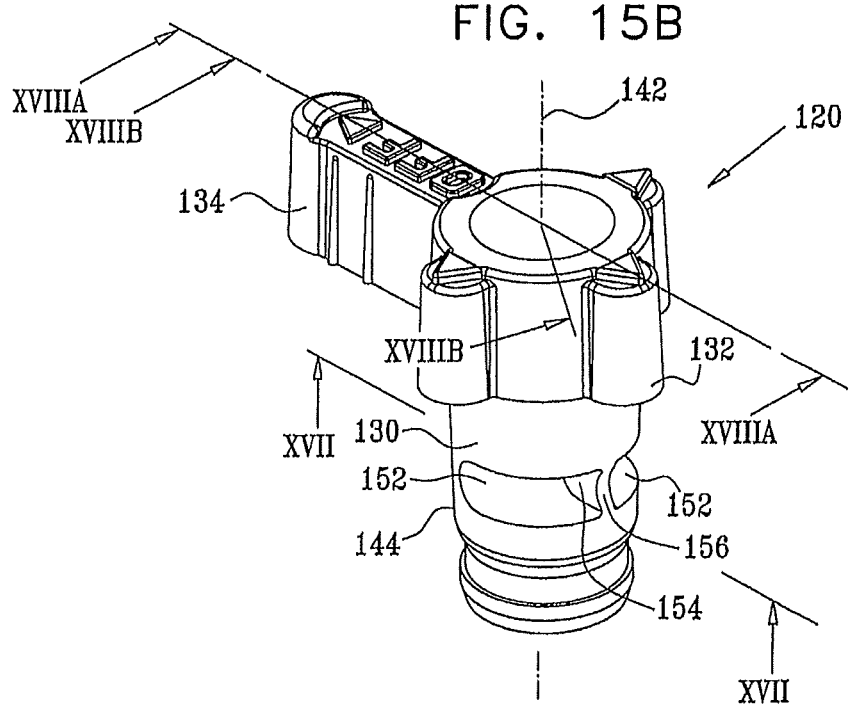
Figure 16A:
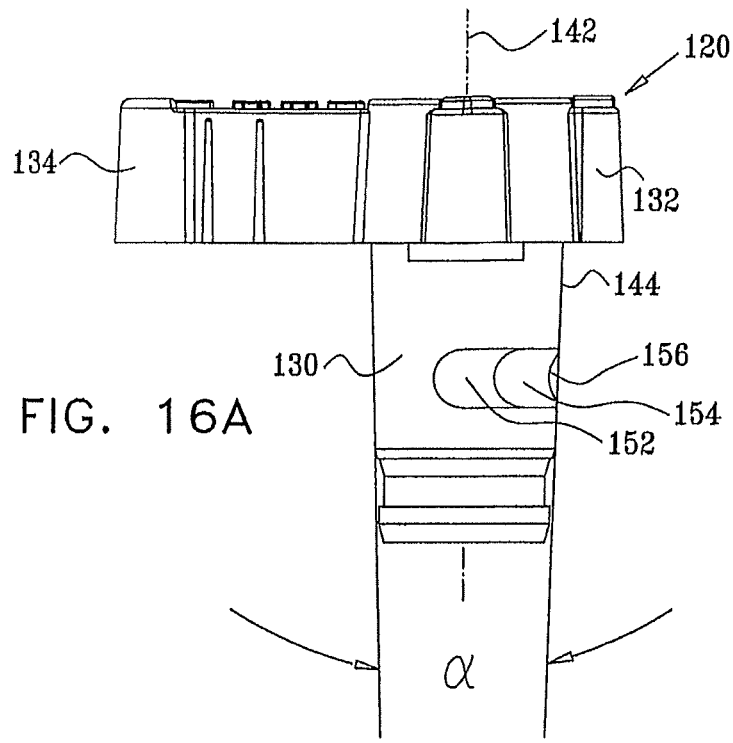
FIGS. 16A and 16B are simplified plan view illustrations of the handle element of FIGS. 15A and 15B taken along respective directions A and B in FIG. 15A.
Figure 16B:
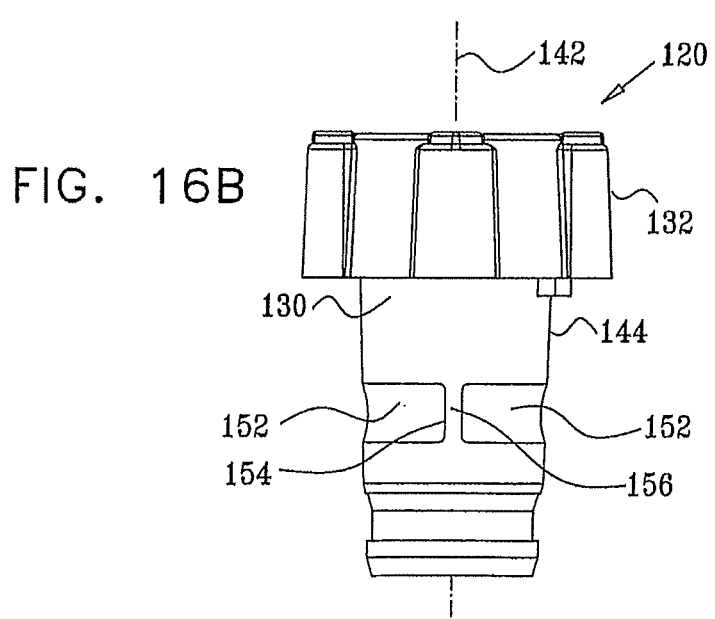
Figure 17:
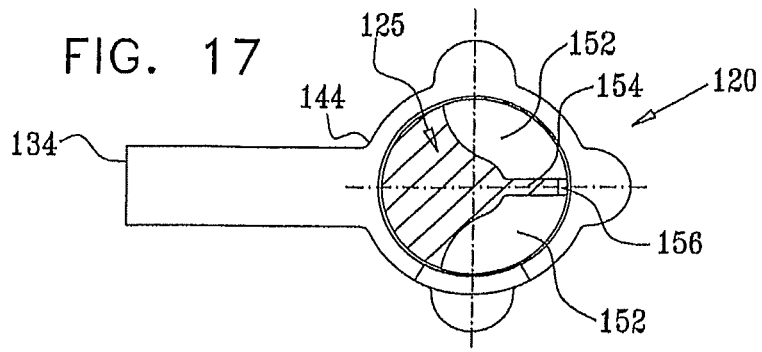
FIGS. 17, 18A and 18B are sectional illustrations taken along section lines XVII-XVII, XVIIIA-XVIIIA and XVIIIB-XVIIIB in FIG. 15B.
Figure 18A:
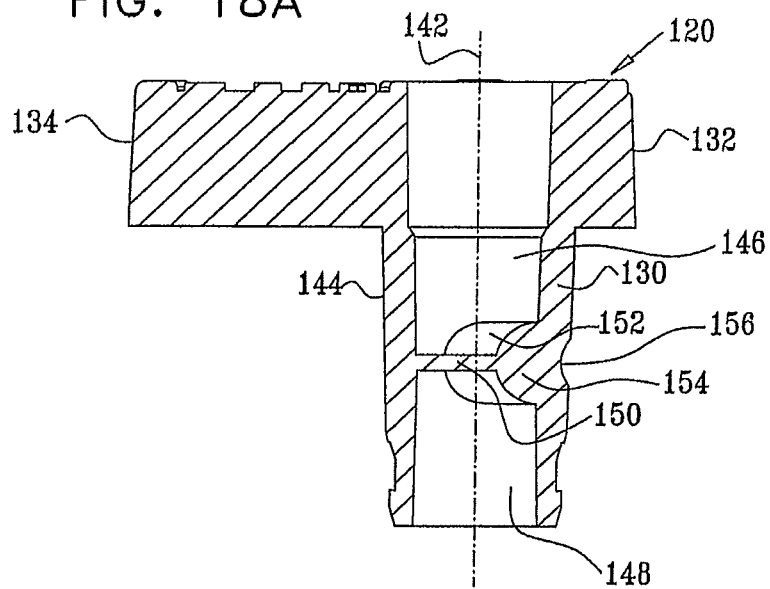
Figure 18B:
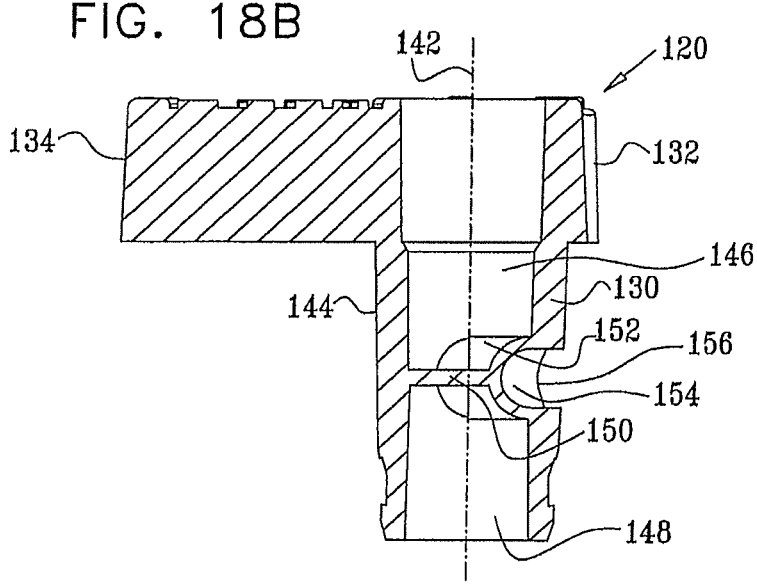

Reference is now made additionally to FIGS. 12 and 13 which are pictorial illustrations of housing element 110 and to FIGS. 14A and 14B which are sectional illustrations thereof. As seen in FIGS. 11-14B, tubular portion 112 of housing element 110 is generally cylindrical, arranged about an axis 122, and has side ports 114, 116 and 118 extending in different directions therefrom, typically separated by 90 degrees about axis 122. Port 114 is preferably a male port which preferably meets luer standard ISO 594-1, while port 116 incorporates a normally closed swabbable valve which is configured to receive a male luer and port 118 is preferably a female port, which preferably meets luer standard ISO 594-1. Conventional plugs, nuts and covers may be used in association with ports 114 and 118.

Port 116 of housing element 110 includes a valve employing an elastomeric element 123, held in place by a cap 124, which is welded or otherwise fixed to housing element 110. Elastomeric element 123 and cap 124 are commercially available from Halkey-Roberts Corporation of St. Petersburg, Fla., USA and described in one or more of U.S. Pat. Nos. 6,651,956; 6,089,541 and 6,036,171, the disclosures of which are hereby incorporated by reference. Alternatively, valves and valve elements commercially available from other sources such as Becton-Dickinson, Cardinal, Medegen and Filtertek may be employed.

Tubular portion 112 includes a central bore 125 having a slightly conical configuration, which is formed with a circumferential undercut 126. Port 116 defines an internal volume 127.

Reference is now made to FIGS. 15A-18B, which illustrate handle element 120. As seen in FIGS. 15A-18B, the handle element includes a shaft portion 130, which is integrally formed with a top portion 132 from which extends a finger-engageable protrusion 134. It is appreciated that any other suitable general configuration of the top portion of the handle element may alternatively be employed.

Shaft portion 130 is generally symmetrical about a shaft axis 142 and has a slightly conical outer surface 144, typically having an angle α (as seen particularly in FIG. 16A) of 3-4 degrees, which corresponds to the slightly conical configuration of central bore 125 for rotatable sealing engagement therewith. As seen particularly in FIGS. 18A and 18B, shaft portion 130 is typically formed with mutually sealed top and bottom cylindrical recesses 146 and 148, which are sealingly separated by a divider 150.

Disposed generally between recesses 146 and 148 and sealed therefrom is a partially peripherally-extending recess 152, selectably defining a fluid flow passageway between selectable ones of side ports 114, 116 and 118 depending on the rotational orientation of the handle element 120 relative to the housing element 110. Preferably extending radially and partially bifurcating the recess 152 is a fluid flow guide 154, which directs the flow of liquid between ports 114 and 118 through the passageway defined by recess 152 into the internal volume 127 of port 116 for flushing thereof, when the handle element 120 is suitably positioned. The radially outward facing edge 156 of fluid flow guide 154 is formed with a concave configuration.

Reference is now made to FIGS. 19A, 19B, 19C and 19D, which are simplified pictorial illustrations of the stopcock of FIG. 11 in four operative orientations and to FIGS. 20A, 20B, 20C and 20D, which are sectional illustrations of the stopcock of FIGS. 19A, 19B, 19C and 19D, respectively.

Figure 19A:
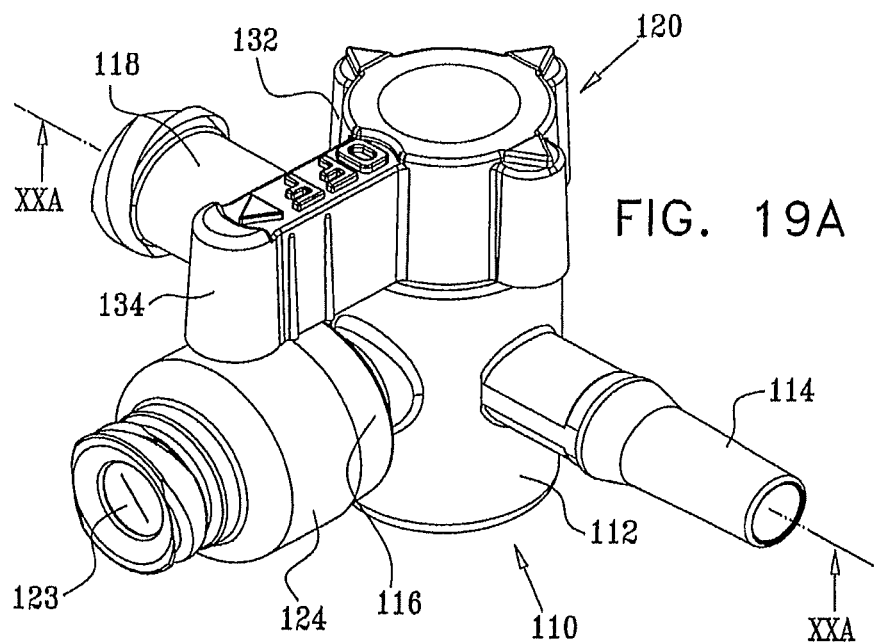
FIGS. 19A, 19B, 19C and 19D are simplified pictorial illustrations of the stopcock of FIG. 11 in four operative orientations.
Figure 20A:
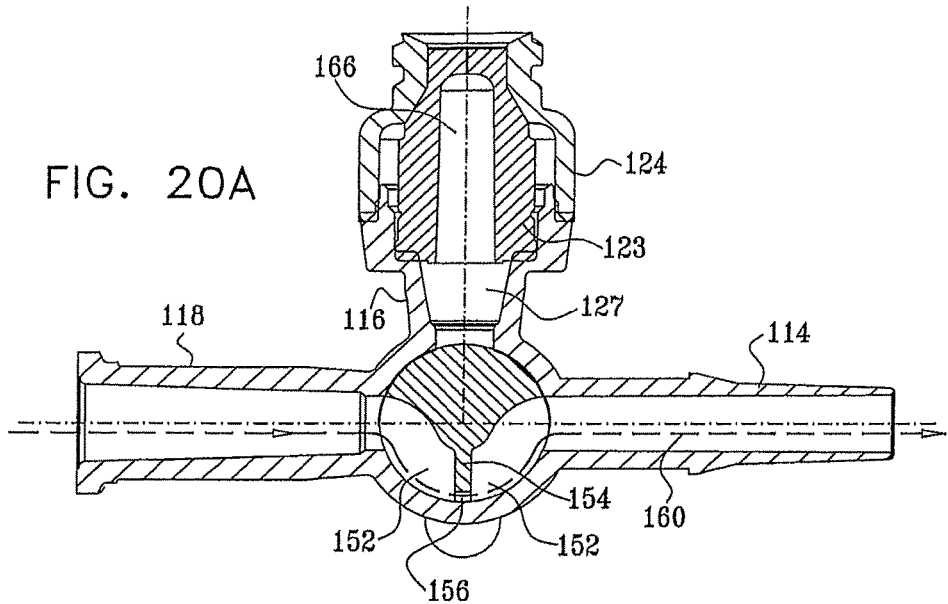

FIGS. 19A and 20A illustrate a first operating position of the stopcock of FIG. 11. The user typically connects a source of pressurized fluid, such as an IV set, to port 118 and the liquid flows through port 118 and partially peripherally-extending recess 152 and past the concave edge 156 of fluid flow guide 154 via port 114 to the patient, as indicated by an arrow 160.

Figure 19B:
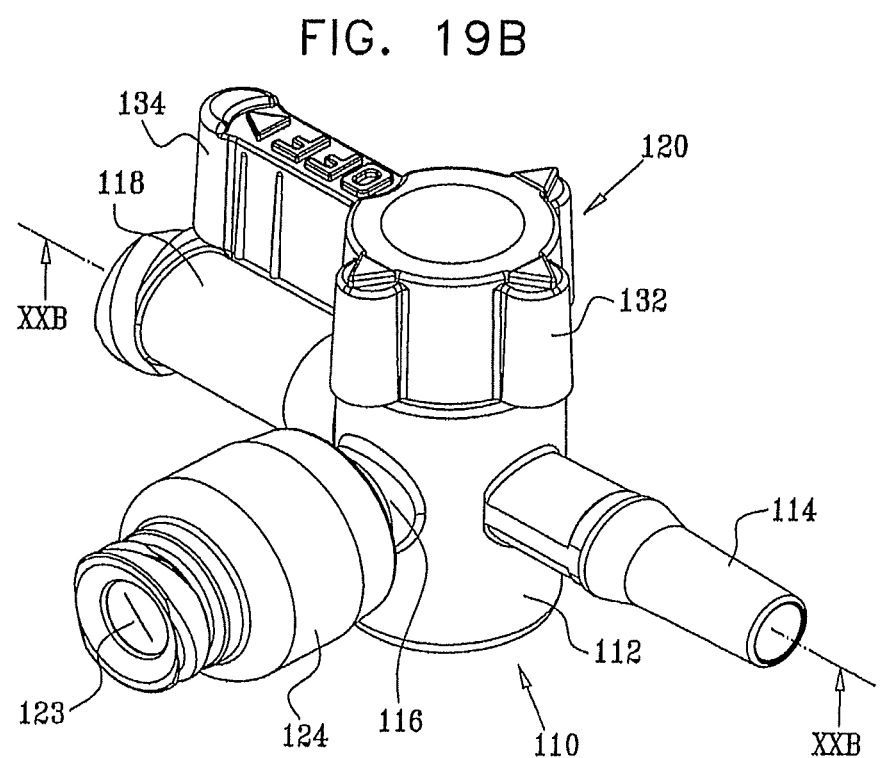
Figure 20B:
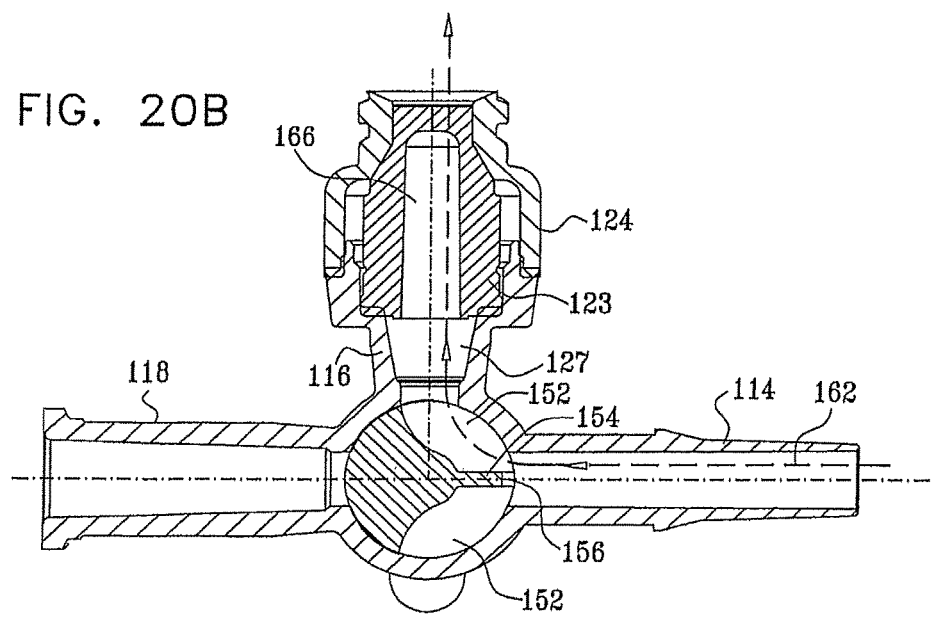

FIGS. 19B and 20B illustrate a second operating position of the stopcock of FIG. 11, which is typically employed for drawing blood or other fluids from the patient. The user typically connects a syringe to port 116 and draws blood from the patient through port 114 and partially peripherally-extending recess 152 through port 116 to the syringe, as indicated by an arrow 162. It is appreciated that this operating position may also be used for supplying a medicament to the patient when port 118 is closed, in a flow direction opposite to that indicated by arrow 162.

Figure 19C:
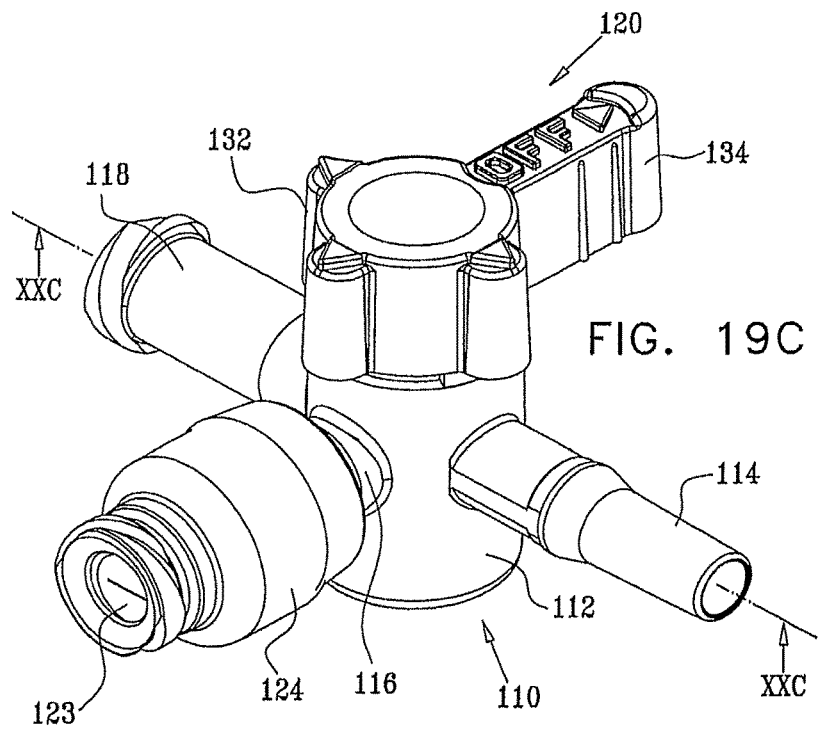

FIGS. 19C and 20C illustrate a third operating position of the stopcock of FIG. 11, which is typically employed for supplying a liquid to the patient from port 118 to port 114. Liquid flows via port 118 and partially peripherally-extending recess 152, around fluid flow guide 154, and into the internal volume 127 of port 116 as well as an internal volume 166 of the elastomeric element 123, flushing residual liquid therefrom, via port 114 to the patient, as indicated by an arrow 164.

It is a particular feature of the present invention that the provision of fluid flow guide 154 generally overcomes problems of the presence of residual liquids remaining in the internal volume 127 of port 116 as well as in internal volume 166 of the elastomeric element 123. This is important in various therapeutic situations. For example when blood is drawn from the patient through port 116, there remains residual blood in the internal volumes 127 of port 116 and 166 of elastomeric element 123. This blood, if left in internal volumes 127 and 166 for a period of time, can clot and thus become dangerous if delivered to the patient. In addition, the coagulated blood could occlude the liquid passageway extending through port 116. Various infections could possibly arise as a result of the retained blood.

This feature is also useful when a medicament is supplied to a patient through port 116. If a portion of the medicament remains in the internal volumes 127 of port 116 and 166 of the elastomeric element 123, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament, from the internal volumes 127 and 166 and typically returning it to the patient without requiring the use of extra syringes and the opening of the medical set to the atmosphere, thereby increasing the chance of contamination.

Figure 19D:
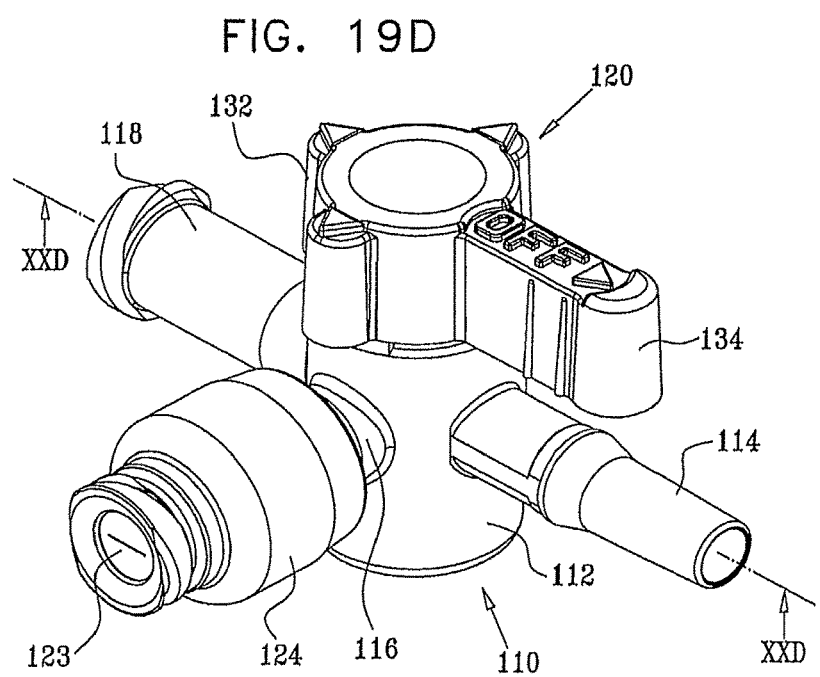

FIGS. 19D and 20D illustrate a fourth operating position of the stopcock of FIG. 11, which may be used for flushing the IV set upstream of the stopcock, when port 116 is open to the atmosphere as by insertion of a male luer connector, such as a syringe tip (not shown), into the elastomeric element 123 of the valve thereof. The insertion of the male luer connector activates the flow of liquid from port 118, around fluid flow guide 154 and through partially peripherally-extending recess 152, to the male luer connector via the elastomeric element 123 of port 116, as indicated by an arrow 165. Alternatively, this operating position may be employed for pushing liquid via the side port 116 and through port 118 in a direction opposite arrow 165, for example when it is desired to mix liquid in the pressure bag.

Reference is now made to FIG. 21, which is an exploded view illustration of a stopcock constructed and operative in accordance with a preferred embodiment of the present invention. As seen in FIG. 21, the stopcock comprises a housing element 210 including a main tubular portion 212 and three side ports, designated by reference numerals 214, 216 and 218 respectively. A handle element 220 is arranged to be seated within main tubular portion 212 of housing element 210.

Figure 22:
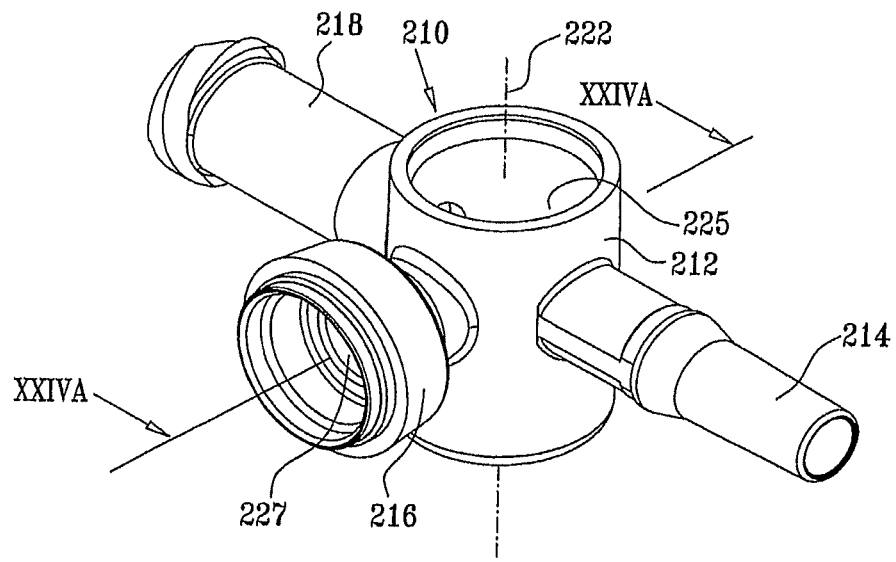
FIGS. 22 and 23 are simplified pictorial illustrations of a housing element, which forms part of the stopcock of FIG. 21 taken in two different directions.
Figure 23:
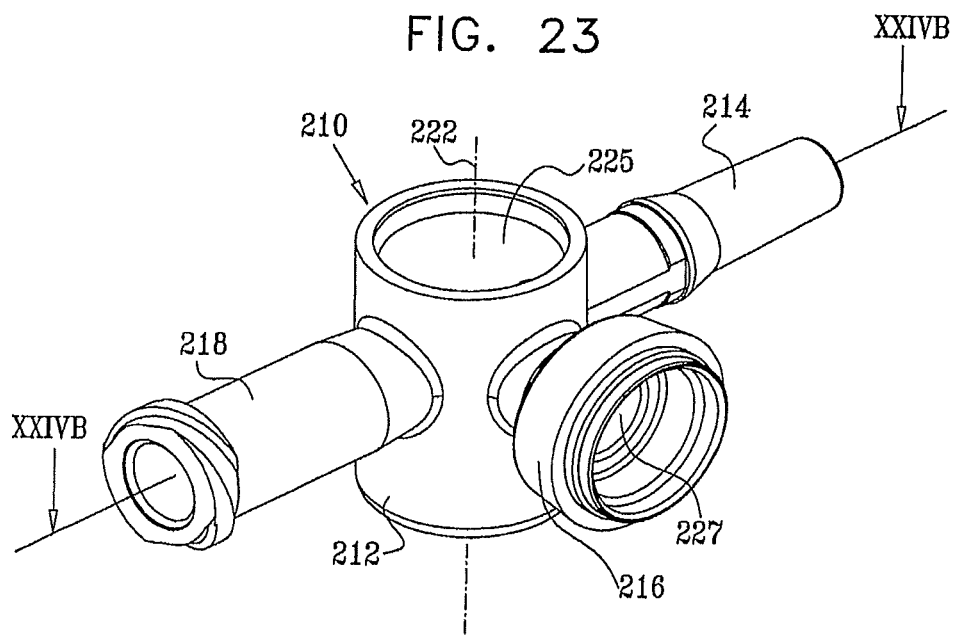
Figure 24A:
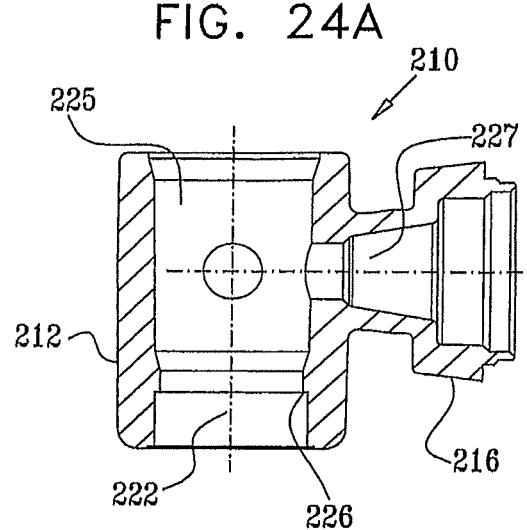
FIGS. 24A and 24B are sectional illustrations taken along section lines XXIVA-XXIVA and XXIVB-XXIVB in FIGS. 22 and 23, respectively.
Figure 24B:
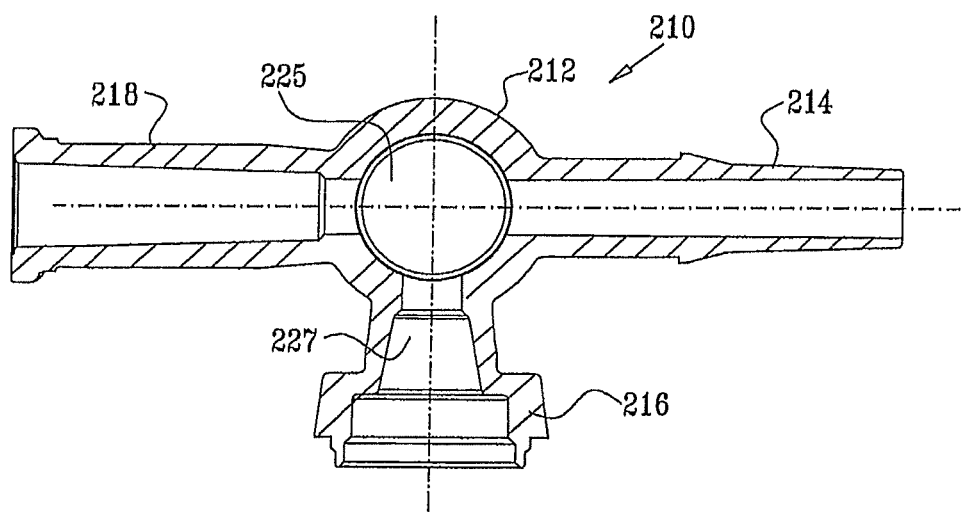
Figure 25A:
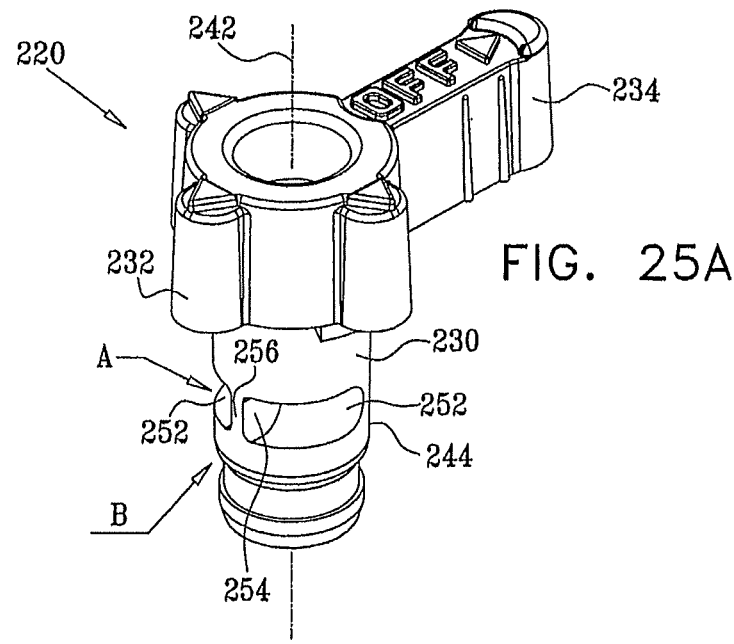
FIGS. 25A and 25B are simplified pictorial illustrations of a handle element which forms part of the stopcock of FIG. 21 in two orientations.
Figure 25B:
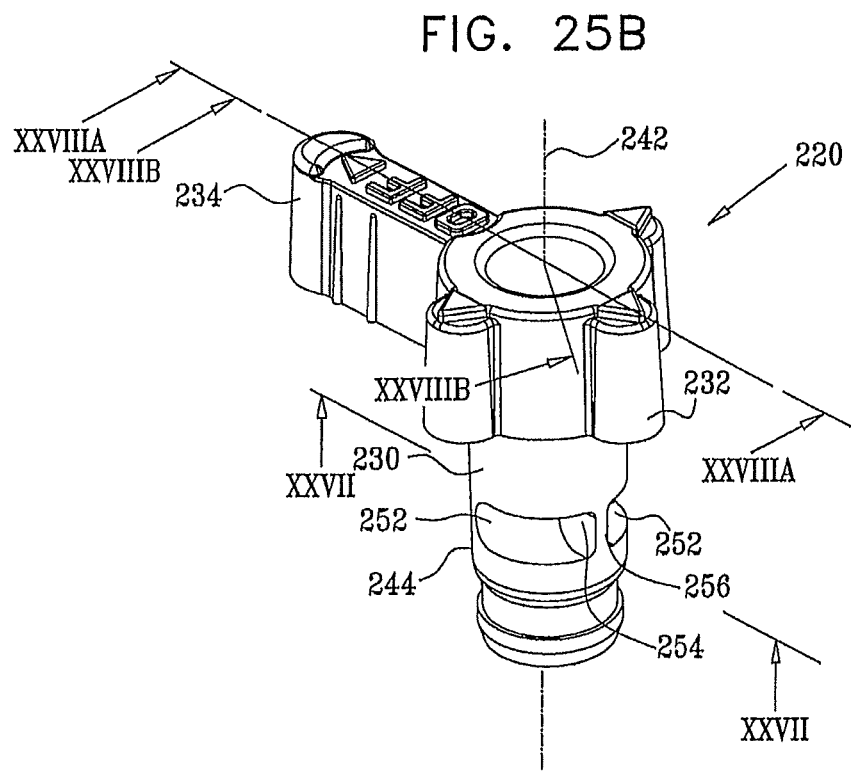
Figure 26A:
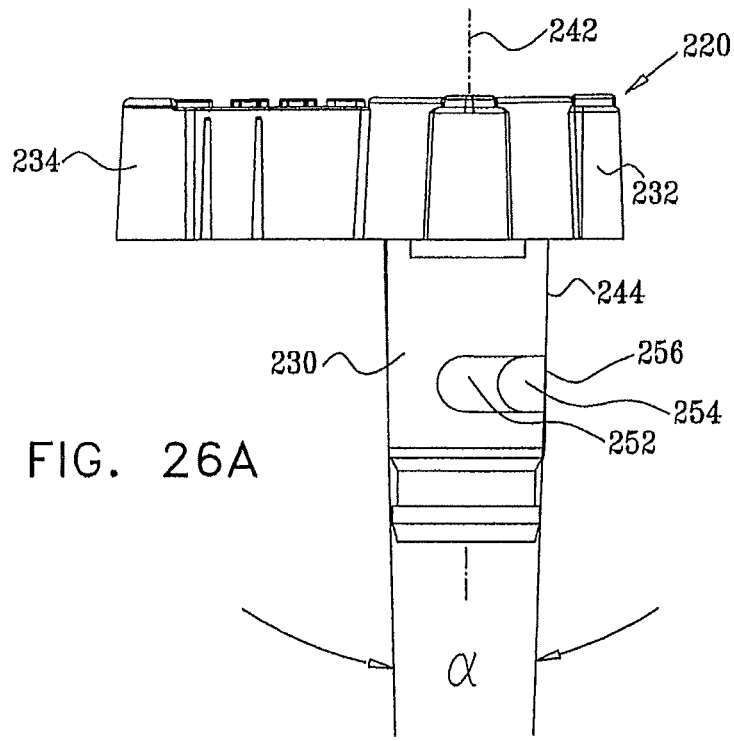
FIGS. 26A and 26B are simplified plan view illustrations of the handle element of FIGS. 25A and 25B taken along respective directions A and B in FIG. 25A.
Figure 26B:
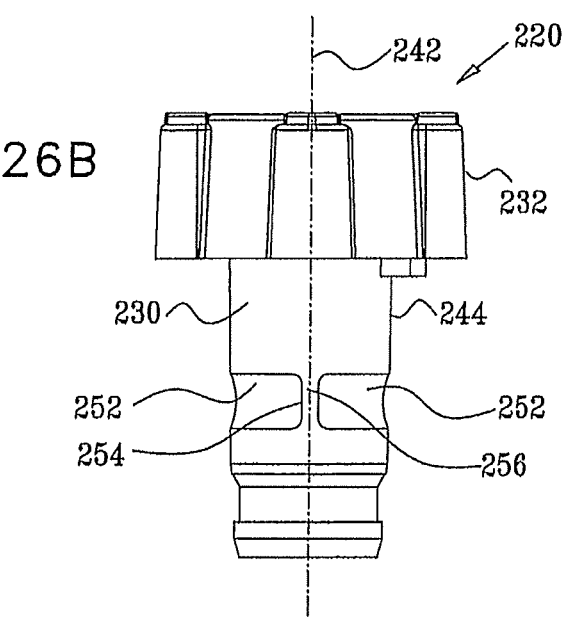
Figure 27:
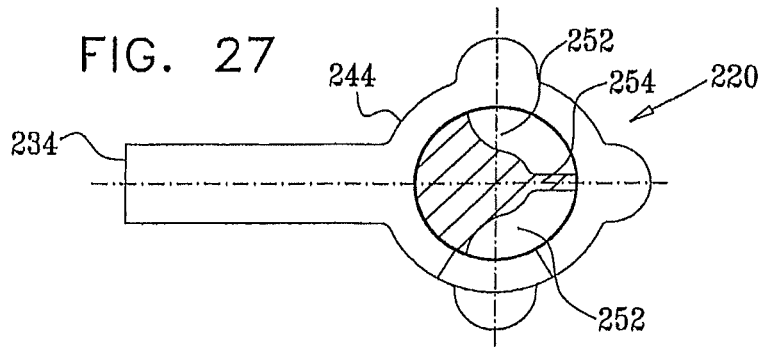
FIGS. 27, 28A and 28B are sectional illustrations taken along section lines XXVII-XXVII, XXVIIIA-XXVIIIA and XXVIIIB-XXVIIIB in FIG. 25B.
Figure 28A:
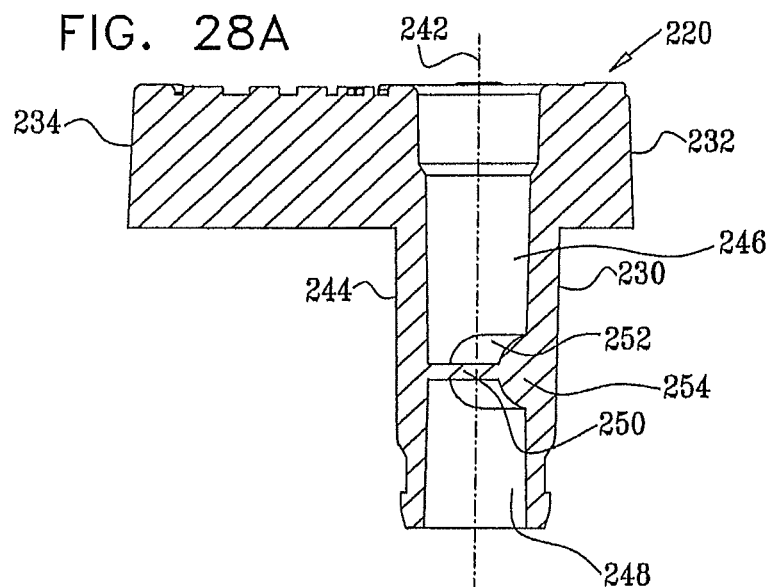
Figure 28B:
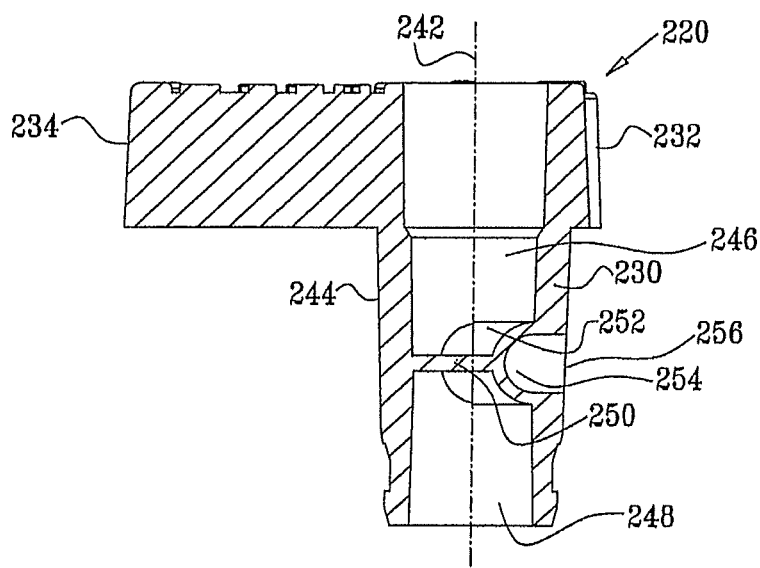

Reference is now made additionally to FIGS. 22 and 23 which are pictorial illustrations of housing element 210 and to FIGS. 24A and 24B which are sectional illustrations thereof. As seen in FIGS. 21-24B, tubular portion 212 of housing element 210 is generally cylindrical, arranged about an axis 222, and has side ports 214, 216 and 218 extending in different directions therefrom, typically separated by 90 degrees about axis 222. Port 214 is preferably a male port which preferably meets luer standard ISO 594-1, while port 216 incorporates a normally closed swabbable valve which is configured to receive a male luer and port 218 is preferably a female port, which preferably meets luer standard ISO 594-1. Conventional plugs, nuts and covers may be used in association with ports 214 and 218.

Port 216 of housing element 210 includes a valve employing an elastomeric element 223, held in place by a cap 224, which is welded or otherwise fixed to housing element 110. Elastomeric element 123 and cap 124 are commercially available from Halkey-Roberts Corporation of St. Petersburg, Fla., USA and described in one or more of U.S. Pat. Nos. 6,651,956; 6,089,541 and 6,036,171, the disclosures of which are hereby incorporated by reference. Alternatively, valves and valve elements commercially available from other sources such as Becton-Dickinson, Cardinal, Medegen and Filtertek may be employed.

Tubular portion 212 includes a central bore 225 having a slightly conical configuration, which is formed with a circumferential undercut 226. Port 216 defines an internal volume 227.

Reference is now made to FIGS. 25A-28B, which illustrate handle element 220. As seen in FIGS. 25A-28B, the handle element includes a shaft portion 230, which is integrally formed with a top portion 232 from which extends a finger-engageable protrusion 234. It is appreciated that any other suitable general configuration of the top portion of the handle element may alternatively be employed.

Shaft portion 230 is generally symmetrical about a shaft axis 242 and has a slightly conical outer surface 244, typically having an angle α (as seen particularly in FIG. 26A) of 3-4 degrees, which corresponds to the slightly conical configuration of central bore 225 for rotatable sealing engagement therewith. As seen particularly in FIGS. 28A and 28B, shaft portion 230 is typically formed with mutually sealed top and bottom cylindrical recesses 246 and 248, which are sealingly separated by a divider 250.

Disposed generally between recesses 246 and 248 and sealed therefrom is a partially peripherally-extending recess 252, selectably defining a fluid flow passageway between selectable ones of side ports 214, 216 and 218 depending on the rotational orientation of the handle element 220 relative to the housing element 210. Preferably extending radially and partially bifurcating the recess 252 is a fluid flow guide 254, which directs the flow of liquid between ports 214 and 218 through the passageway defined by recess 252 into the internal volume 227 of port 216 for flushing thereof, when the handle element 220 is suitably positioned. The radially outward facing edge 256 of fluid flow guide 254 is formed with a suitably tapered configuration in order to prevent liquid flow therepast when fluid flow guide 254 is not located opposite a port.

Reference is now made to FIGS. 29A, 29B, 29C and 29D, which are simplified pictorial illustrations of the stopcock of FIG. 21 in four operative orientations and to FIGS. 30A, 30B, 30C and 30D, which are sectional illustrations of the stopcock of FIGS. 29A, 29B, 29C and 29D, respectively.

Figure 29A:
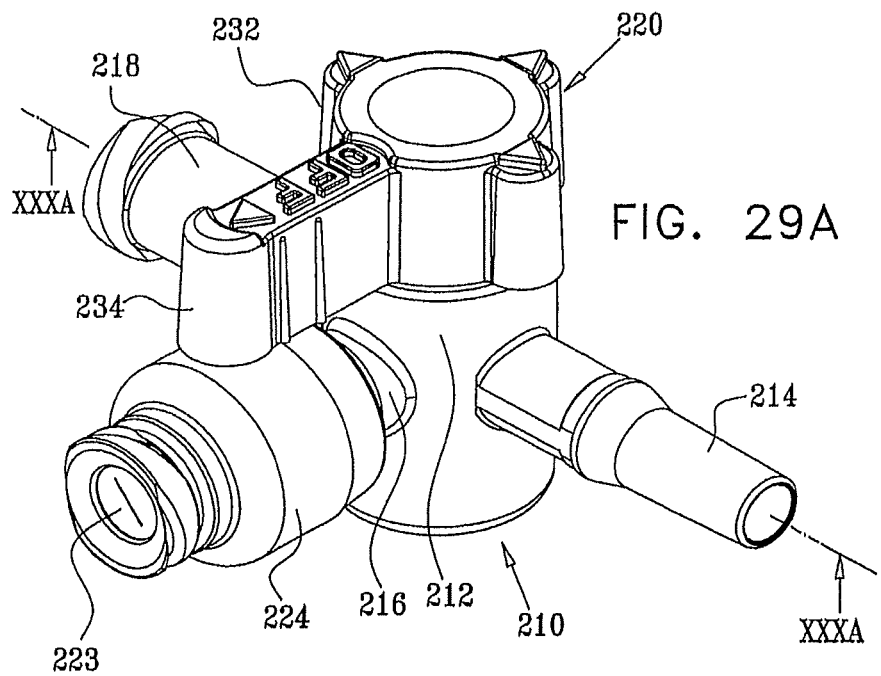
FIGS. 29A, 29B, 29C and 29D are simplified pictorial illustrations of the stopcock of FIG. 21 in four operative orientations.
Figure 30A:
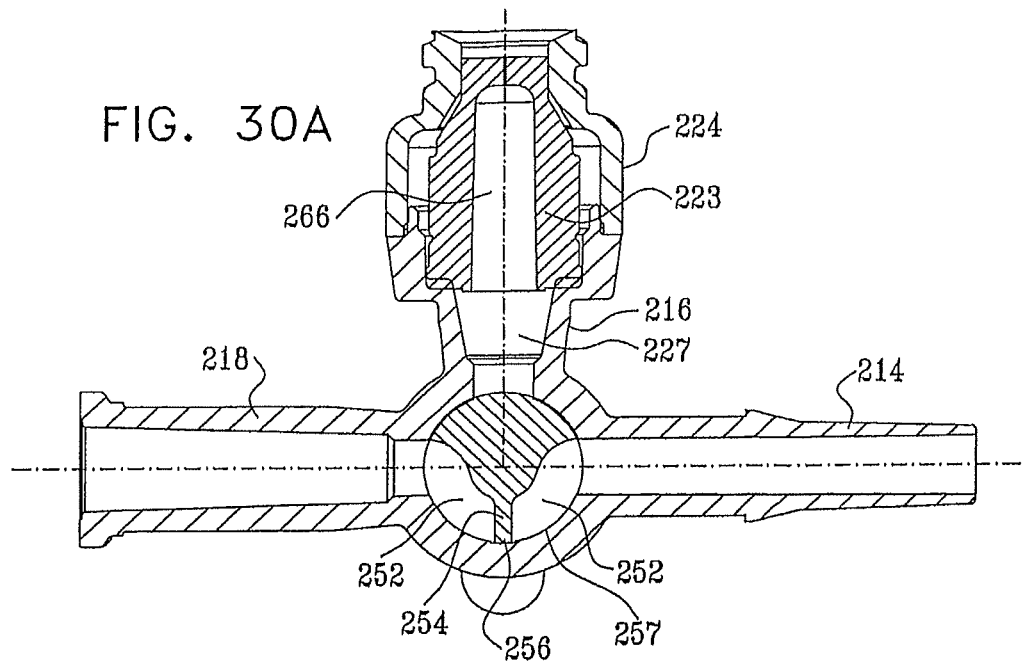
FIGS. 30A, 30B, 30C and 30D are sectional illustrations taken along section lines XXXA-XXXA, XXXB-XXXB, XXXC-XXXC and XXXD-XXXD in FIGS. 29A, 29B, 29C and 29D respectively.

FIGS. 29A and 30A illustrate a first operating position of the stopcock of FIG. 21. As seen, there is no fluid communication between any of the ports. Liquid does not flow from port 218 to port 214, because it is blocked by fluid flow guide 254, whose edge 256 sealingly engages an inner facing wall 257 of bore 225 of housing element 210. This orientation may be utilized to close all three ports.

The operative orientation shown in FIGS. 29A and 30A may be advantageously employed when it is desired to prevent all flow of liquid through the stopcock. The procedure currently used requires careful placement of the handle to an angle 45 degrees from one of the ports. Such a procedure is unreliable and requires careful attention of the operator, which may be a doctor or a nurse in the middle of a surgery.

Figure 29B:
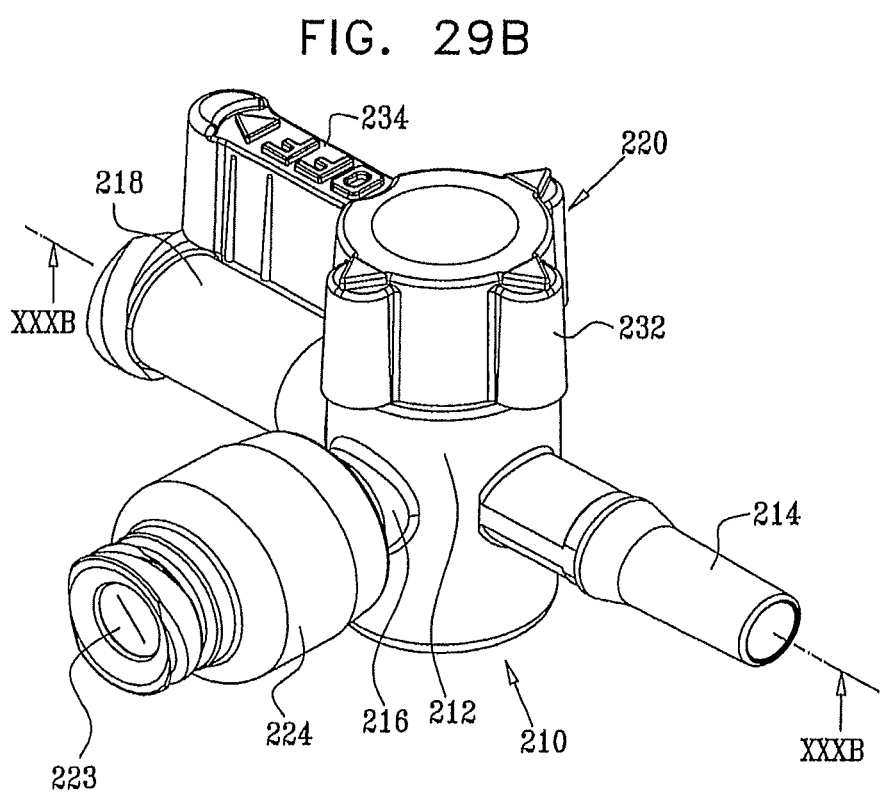
Figure 30B:
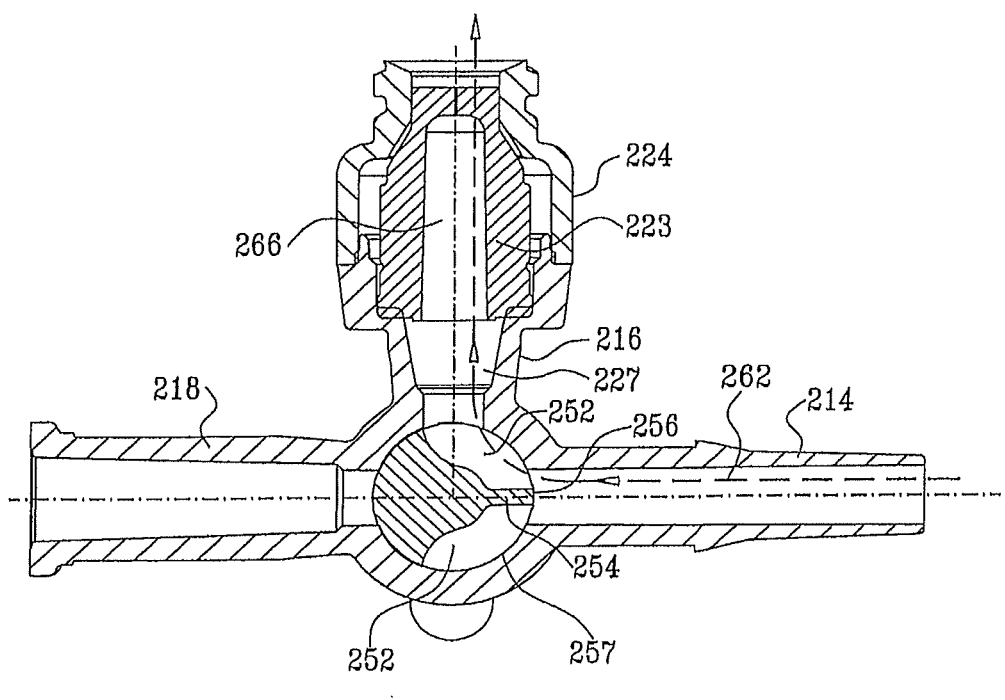

FIGS. 29B and 30B illustrate a second operating position of the stopcock of FIG. 21, which is typically employed for drawing blood or other fluids from the patient. The user typically connects a syringe to port 216 and draws blood from the patient through port 214 and partially peripherally-extending recess 252 through port 216 to the syringe, as indicated by an arrow 262. It is appreciated that this operating position may also be used for supplying a medicament to the patient when port 218 is closed, in a flow direction opposite to that indicated by arrow 262.

Figure 29C:
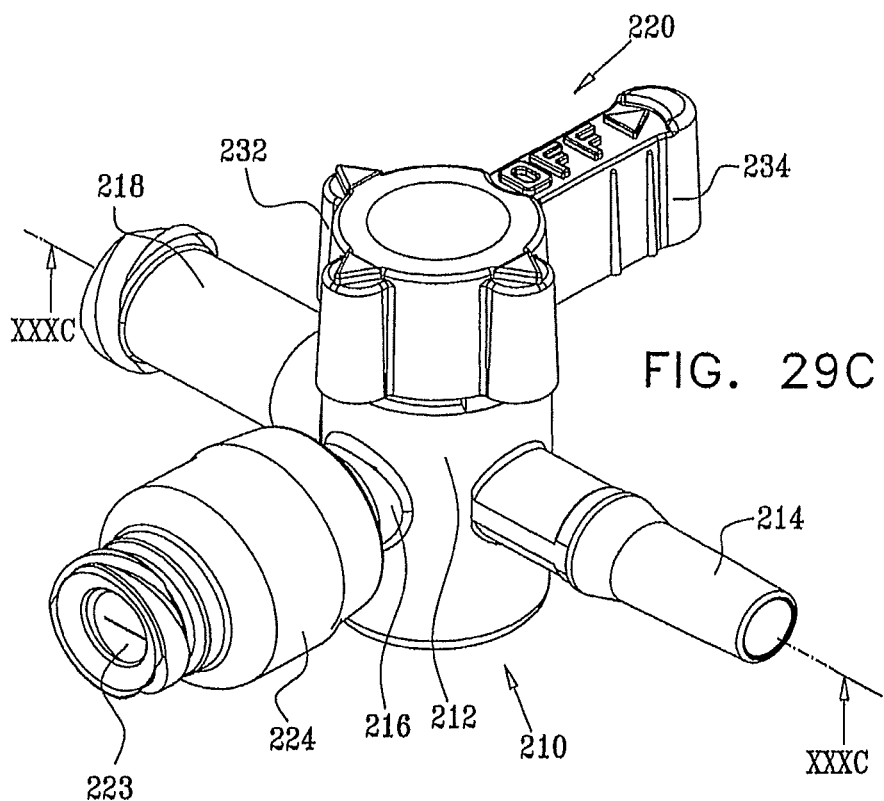
Figure 30C:
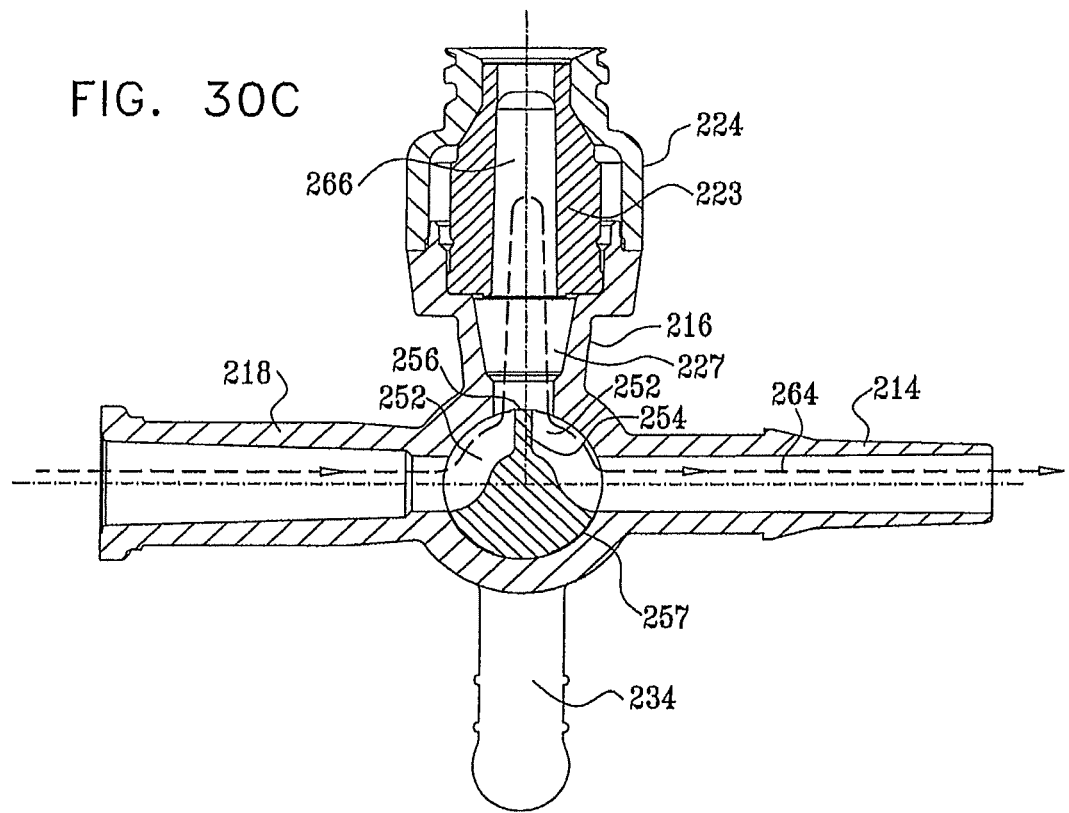

FIGS. 29C and 30C illustrate a third operating position of the stopcock of FIG. 21, which is typically employed for supplying a liquid to the patient from port 218 to port 214. Liquid flows via port 218 and partially peripherally-extending recess 252, around fluid flow guide 254, and into the internal volume 227 of port 216 as well as an internal volume 266 of the elastomeric element 223, flushing residual liquid therefrom, via port 214 to the patient, as indicated by an arrow 264.

It is a particular feature of the present invention that the provision of fluid flow guide 254 generally overcomes problems of the presence of residual liquids remaining in the internal volume 227 of port 216 as well as in internal volume 266 of the elastomeric element 223. This is important in various therapeutic situations. For example when blood is drawn from the patient through port 216, there remains residual blood in the internal volumes 227 of port 216 and 266 of the elastomeric element 223. This blood, if left in internal volumes 227 and 266 for a period of time, can clot and thus become dangerous if delivered to the patient. In addition, the coagulated blood could occlude the liquid passageway extending through port 216. Various infections could possibly arise as a result of the retained blood.

This feature is also useful when a medicament is supplied to a patient through port 216. If a portion of the medicament remains in the internal volumes 227 of port 216 and 266 of the elastomeric element 223, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 227 and 266 and typically returning it to the patient without requiring the use of extra syringes and the opening of the medical set to the atmosphere, thereby increasing the chance of contamination.

Figure 29D:
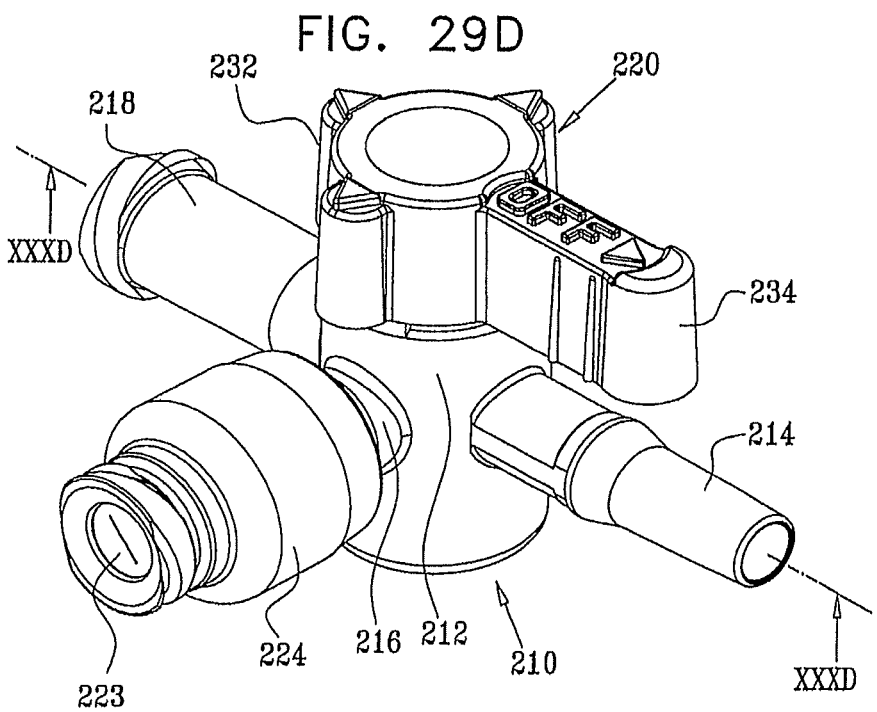
Figure 30D:
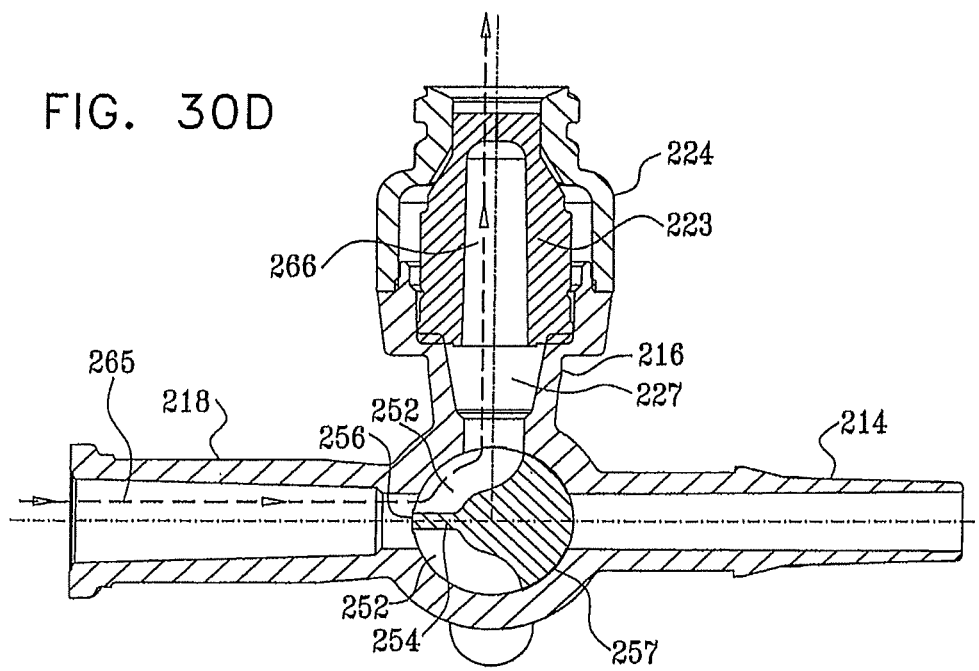

FIGS. 29D and 30D illustrate a fourth operating position of the stopcock of FIG. 21, which may be used for flushing the IV set upstream of the stopcock, when port 216 is open to the atmosphere as by insertion of a male luer connector, such as a syringe tip (not shown), into the elastomeric element 223 of the valve thereof. The insertion of the male luer connector activates the flow of liquid from port 218, around fluid flow guide 254 and through partially peripherally-extending recess 252, to the male luer connector via the elastomeric element 223 of port 216, as indicated by an arrow 265. Alternatively, this operating position may be employed for pushing liquid via the side port 216, through port 218, in a direction opposite arrow 265 for uses such as mixing liquid in the pressure bag.

Figure 31:
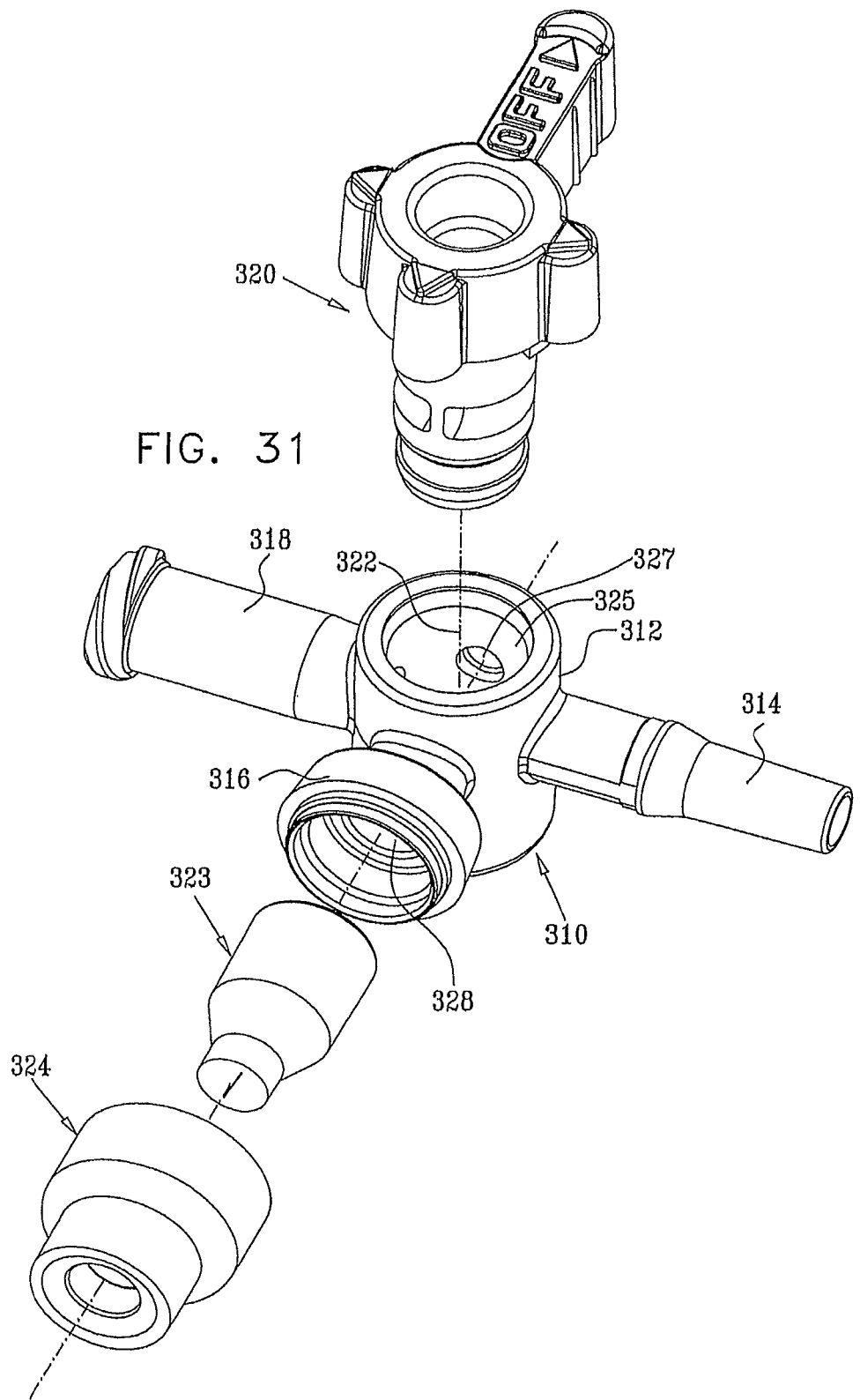
FIG. 31 is a simplified exploded view illustration of a stopcock constructed and operative in accordance with a further preferred embodiment of the present invention.

Reference is now made to FIG. 31, which is an exploded view illustration of a stopcock constructed and operative in accordance with a preferred embodiment of the present invention. As seen in FIG. 31, the stopcock comprises a housing element 310 including a main tubular portion 312 and three side ports, designated by reference numerals 314, 316 and 318 respectively. A handle element 320 is arranged to be seated within main tubular portion 312 of housing element 310.

Figure 32:
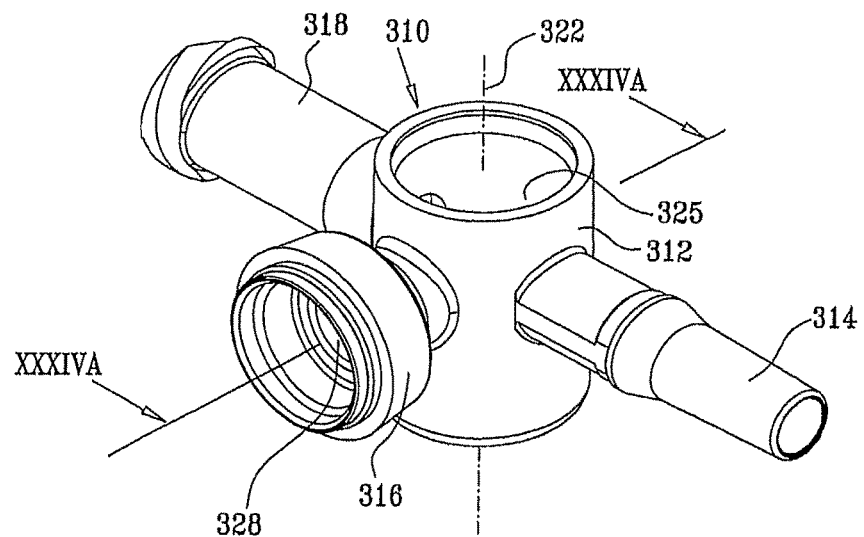
FIGS. 32 and 33 are simplified pictorial illustrations of a housing element, which forms part of the stopcock of FIG. 31 taken in two different directions.
Figure 33:
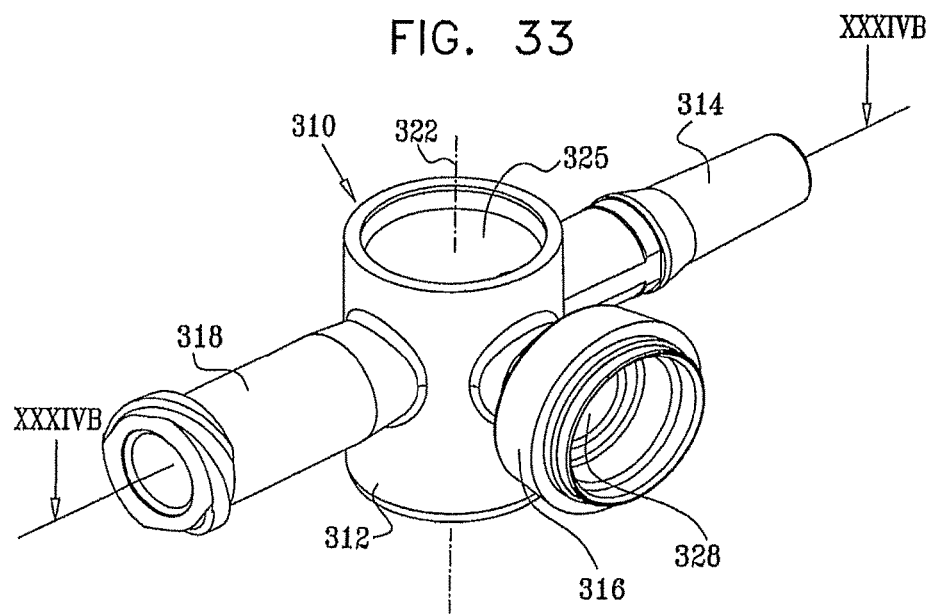
Figure 34A:
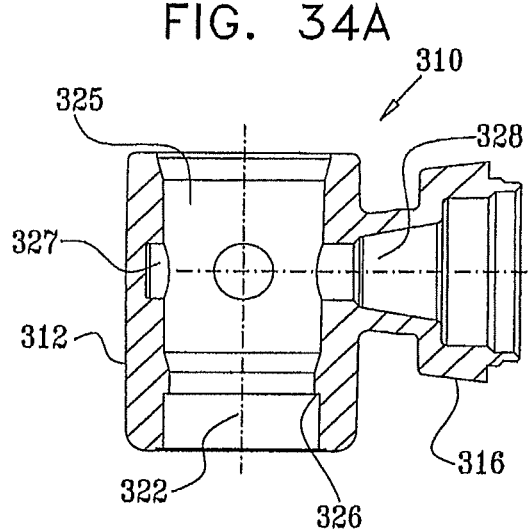
FIGS. 34A and 34B are sectional illustrations taken along section lines XXXIVA-XXXIVA and XXXIVB-XXXIVB in FIGS. 32 and 33, respectively.
Figure 34B:
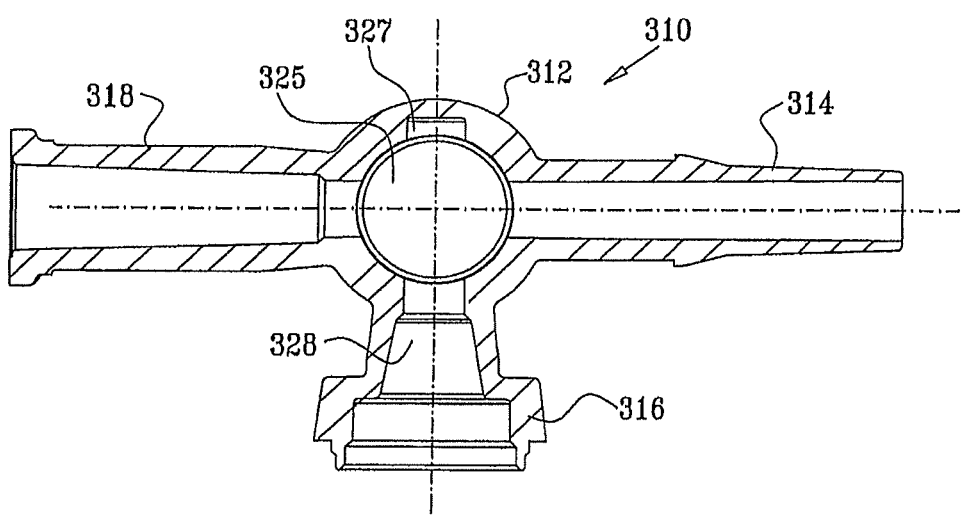
Figure 35A:
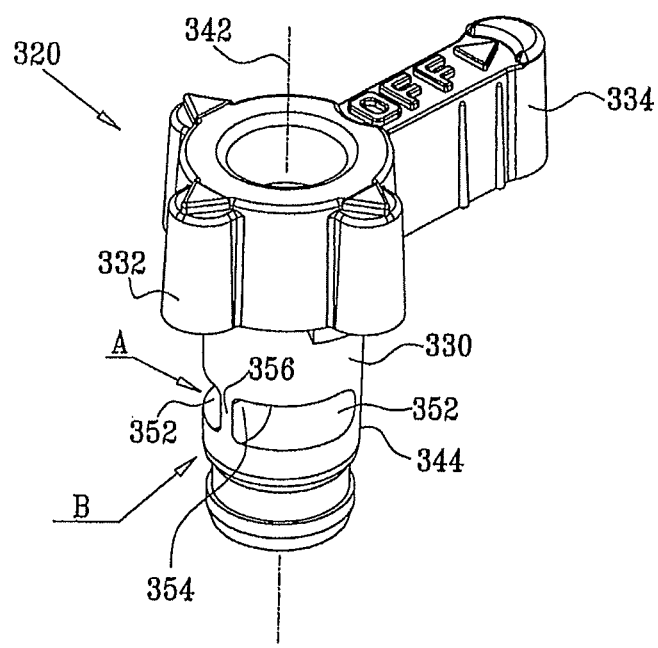
FIGS. 35A and 35B are simplified pictorial illustrations of a handle element which forms part of the stopcock of FIG. 31 in two orientations.
Figure 35B:
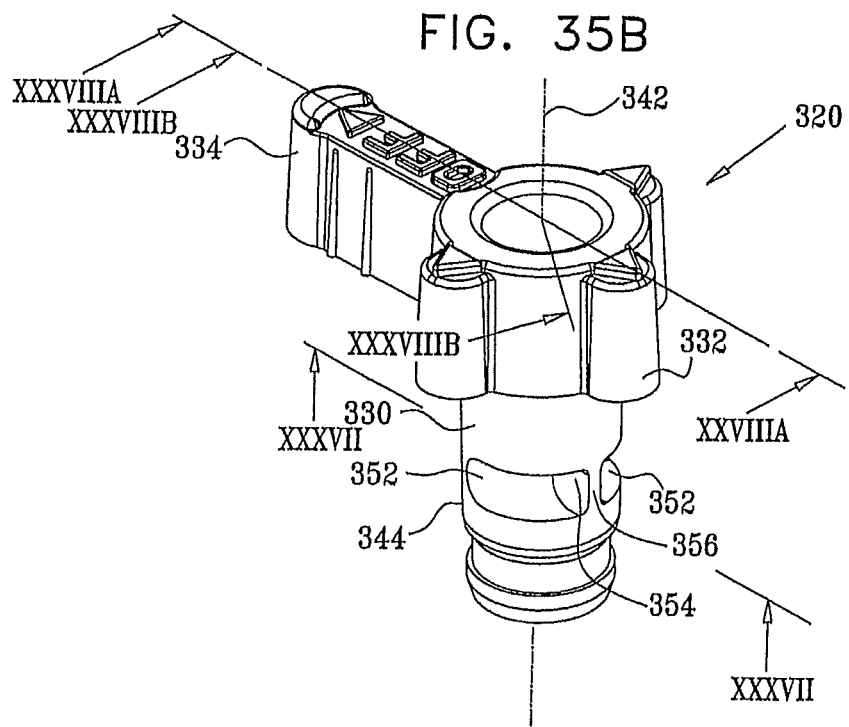
Figure 36A:
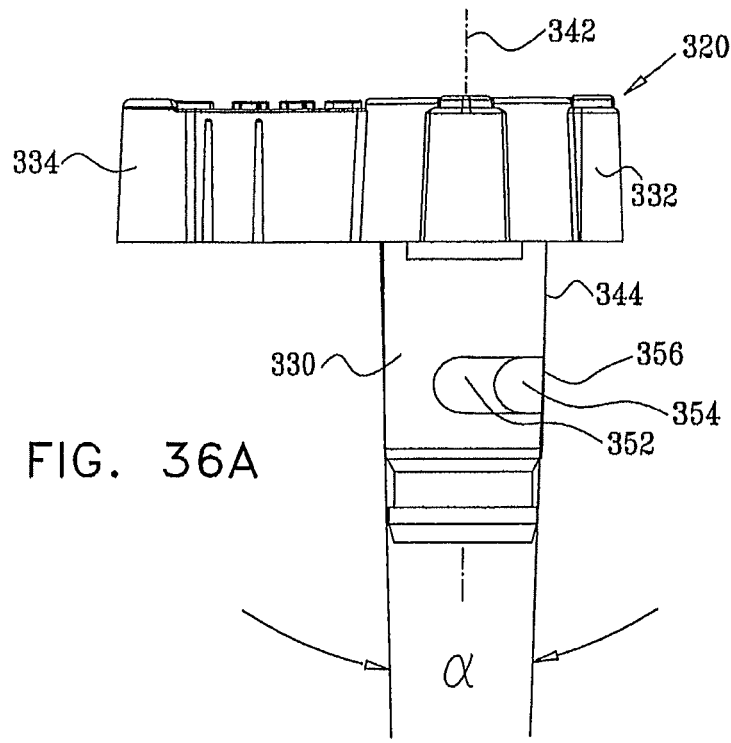
FIGS. 36A and 36B are simplified plan view illustrations of the handle element of FIGS. 35A and 35B taken along respective directions A and B in FIG. 35A.
Figure 36B:
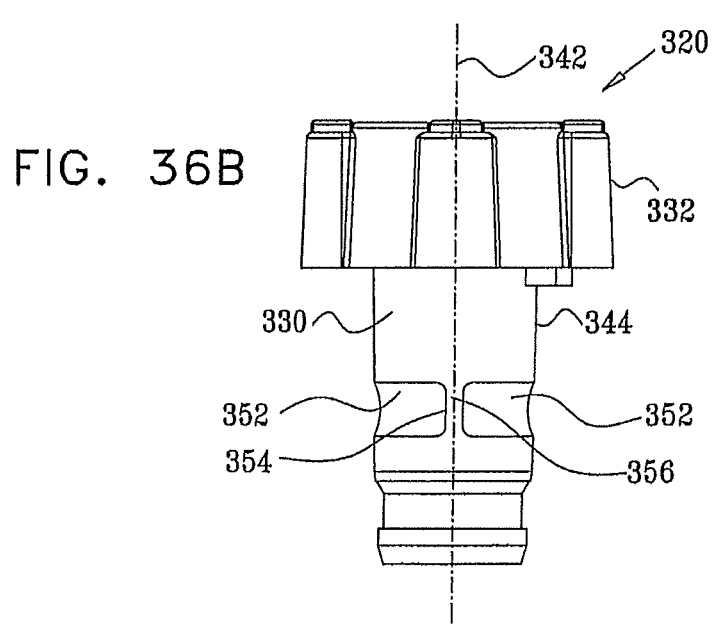
Figure 37:
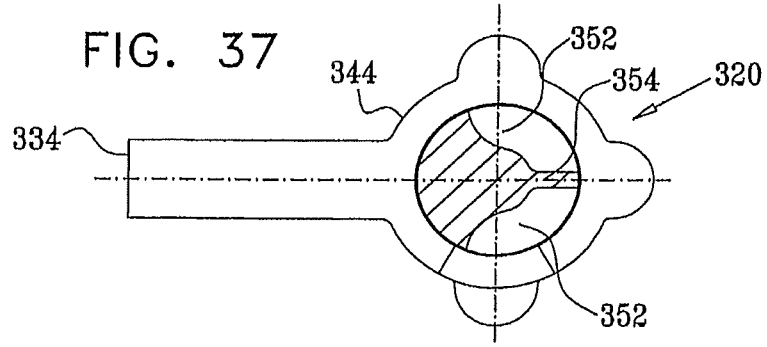
FIGS. 37, 38A and 38B are sectional illustrations taken along section lines XXXVII-XXXVII, XXXVIIIA-XXXVIIIA and XXXVIIIB-XXXVIIIB in FIG. 35B.
Figure 38A:
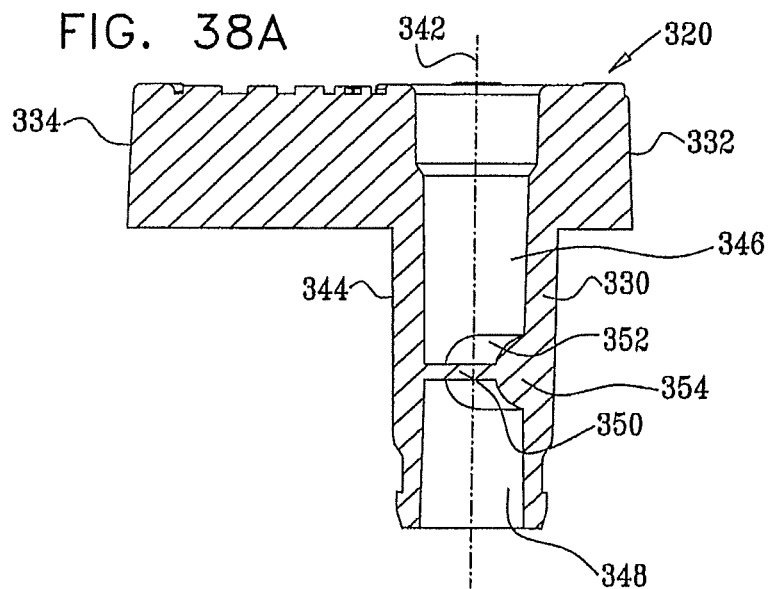
Figure 38B:
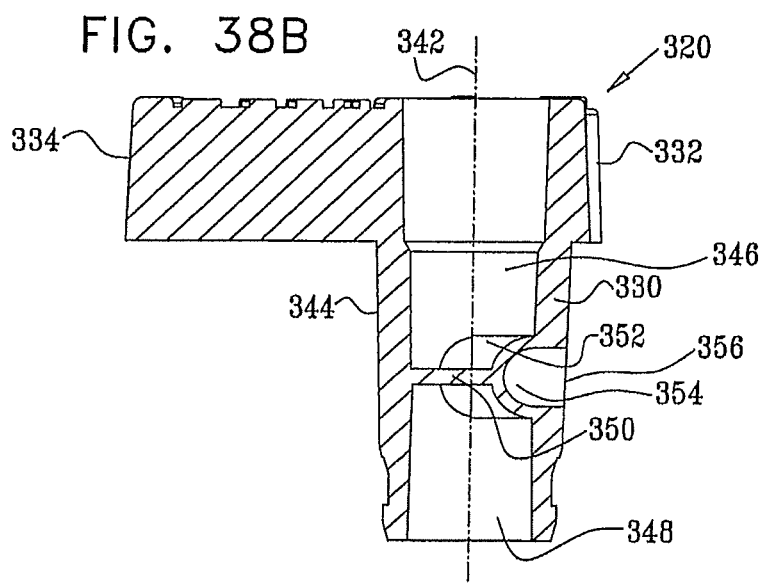

Reference is now made additionally to FIGS. 32 and 33 which are pictorial illustrations of housing element 310 and to FIGS. 34A and 34B which are sectional illustrations thereof. As seen in FIGS. 31-34B, tubular portion 312 of housing element 310 is generally cylindrical, arranged about an axis 322, and has side ports 314, 316 and 318 extending in different directions therefrom, typically separated by 90 degrees about axis 322. Port 314 is preferably a male port which preferably meets luer standard ISO 594-1, while port 316 incorporates a normally closed swabbable valve which is configured to receive a male luer and port 318 is preferably a female port, which preferably meets luer standard ISO 594-1. Conventional plugs, nuts and covers may be used in association with ports 314 and 318.

Port 316 of housing element 310 includes a valve employing an elastomeric element 323 held in place by a cap 324, which is welded or otherwise fixed to housing element 310. Elastomeric element 323 and cap 324 are commercially available from Halkey-Roberts Corporation of St. Petersburg, Fla., USA and described in one or more of U.S. Pat. Nos. 6,651,956; 6,089,541 and 6,036,171, the disclosures of which are hereby incorporated by reference. Alternatively valves and valve elements commercially available from other sources such as Becton-Dickinson, Cardinal, Medegen and Filtertek may be employed.

Tubular portion 312 includes a central bore 325 having a slightly conical configuration, which is formed with a circumferential undercut 326. In this embodiment, a side recess 327 is formed in a wall of bore 325 opposite port 316. Port 316 defines an internal volume 328.

Reference is now made to FIGS. 35A-38B, which illustrate handle element 320. As seen in FIGS. 35A-38B, the handle element includes a shaft portion 330, which is integrally formed with a top portion 332 from which extends a finger-engageable protrusion 334. It is appreciated that any other suitable general configuration of the top portion of the handle element may alternatively be employed.

Shaft portion 330 is generally symmetrical about a shaft axis 342 and has a slightly conical outer surface 344, typically having an angle α (as seen particularly in FIG. 36A) of 3-4 degrees, which corresponds to the slightly conical configuration of central bore 325 for rotatable sealing engagement therewith. As seen particularly in FIGS. 38A and 38B, shaft portion 330 is typically formed with mutually sealed top and bottom cylindrical recesses 346 and 348, which are sealingly separated by a divider 350.

Disposed generally between recesses 346 and 348 and sealed therefrom is a partially peripherally-extending recess 352. Preferably extending radially and partially bifurcating the recess 352 is a fluid flow guide 354, which directs the flow of liquid between ports 314 and 318 through the passageway defined by recess 352 into the internal volume 328 of port 316 for flushing thereof, when the handle element 320 is suitably positioned. The thickness of fluid flow guide 354 is substantially less than the circumferential extent of side recess 327. The radially outward facing edge 356 of fluid flow guide 354 is formed with a suitably tapered configuration in order to prevent liquid flow therepast when fluid flow guide 354 is not located opposite a port.

Reference is now made to FIGS. 39A, 39B, 39C and 39D, which are simplified pictorial illustrations of the stopcock of FIG. 31 in four operative orientations and to FIGS. 40A, 40B, 40C and 40D, which are sectional illustrations of the stopcock of FIGS. 39A, 39B, 39C and 39D, respectively.

Figure 39A:
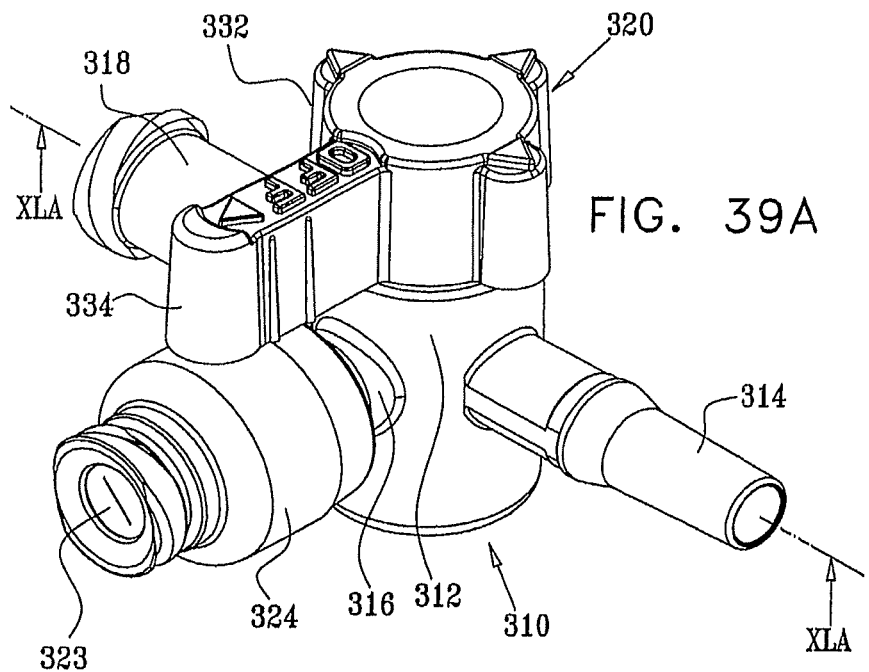
FIGS. 39A, 39B, 39C and 39D are simplified pictorial illustrations of the stopcock of FIG. 31 in four operative orientations.
Figure 40A:
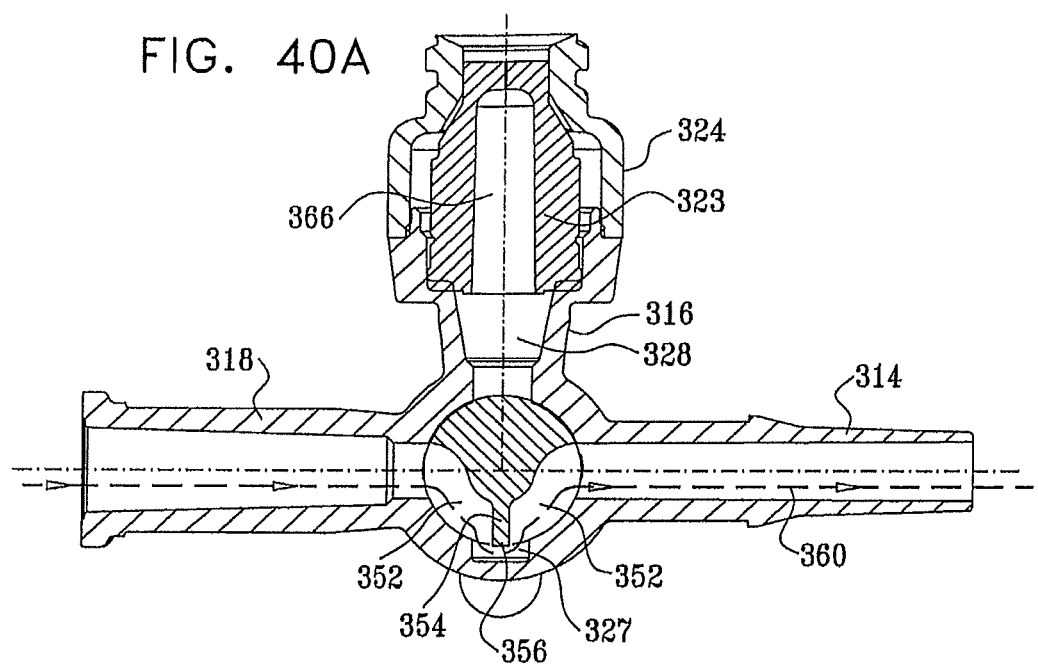
FIGS. 40A, 40B, 40C and 40D are sectional illustrations taken along section lines XLA-XLA, XLB-XLB, XLC-XLC and XLD-XLD in FIGS. 39A, 39B, 39C and 39D respectively.

FIGS. 39A and 40A illustrate a first operating position of the stopcock of FIG. 31. The user typically connects a source of pressurized fluid, such as an IV set, to port 318 and the liquid flows from port 318, around fluid flow guide 354, through side recess 327 to port 314, as indicated by arrow 360.

Figure 39B:
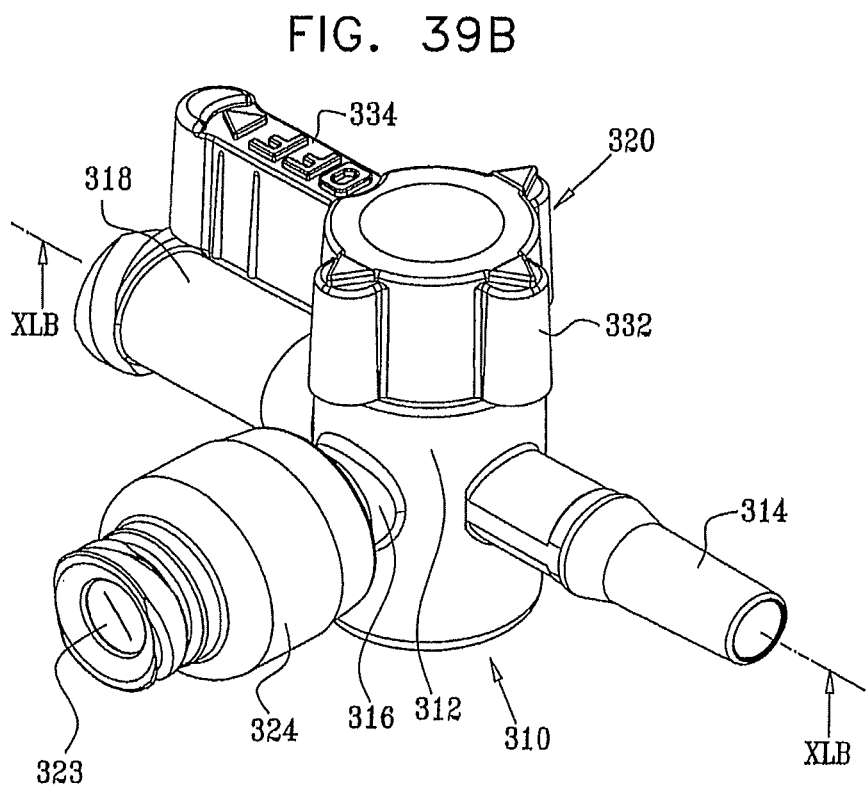
Figure 40B:
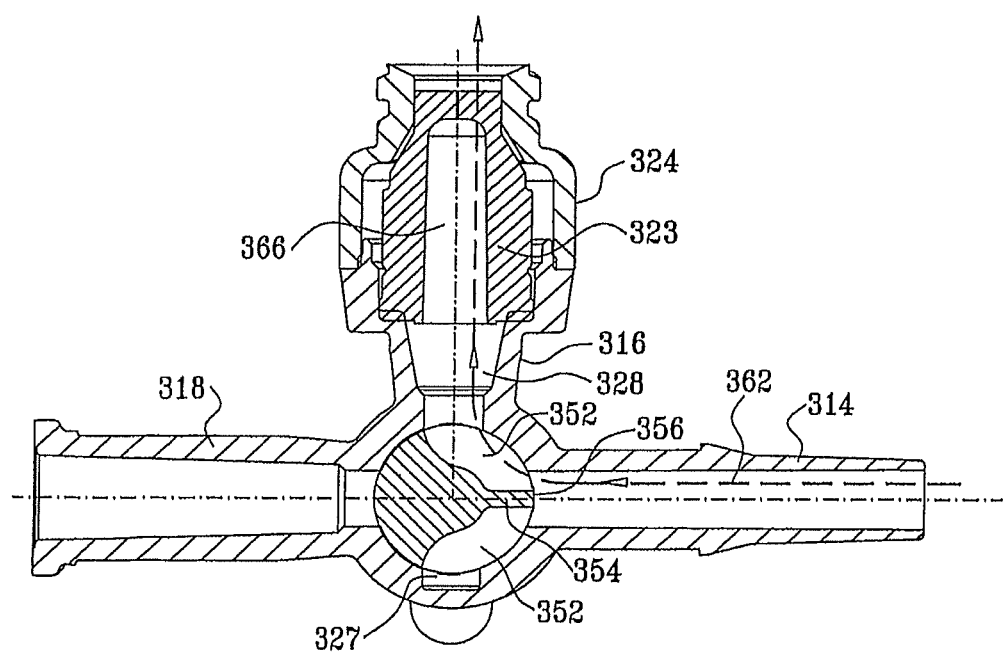

FIGS. 39B and 40B illustrate a second operating position of the stopcock of FIG. 31, which is typically employed for drawing blood or other fluids from the patient. The user typically connects a syringe to port 316 and draws blood from the patient through port 314 and partially peripherally-extending recess 352 through port 316 to the syringe, as indicated by an arrow 362. It is appreciated that this operating position may also be used for supplying a medicament to the patient when port 318 is closed, in a flow direction opposite to that indicated by arrow 362.

Figure 39C:
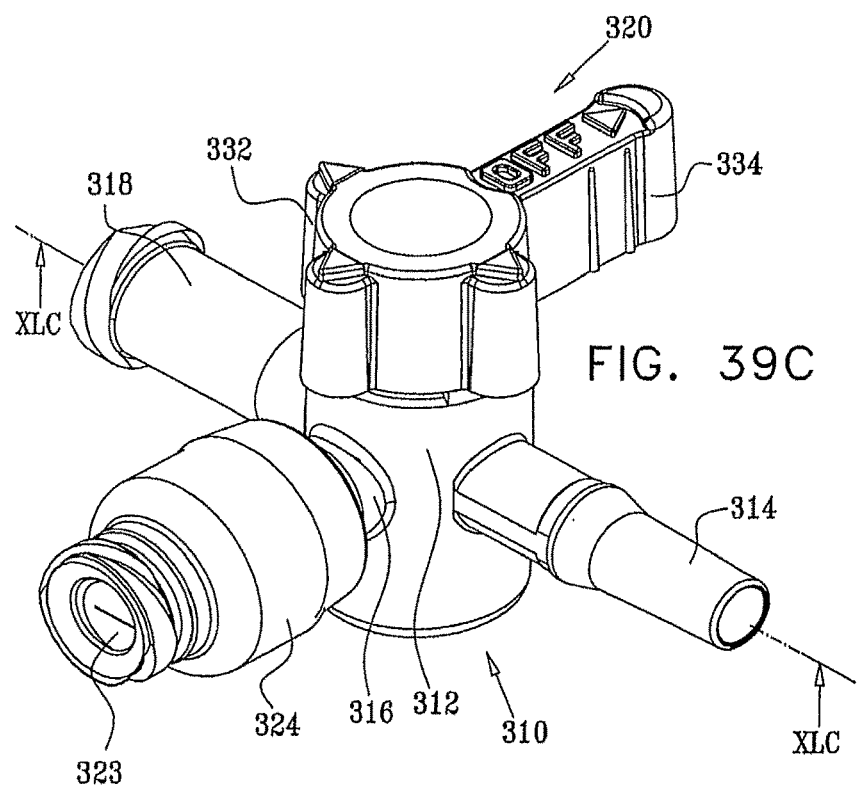
Figure 40C:
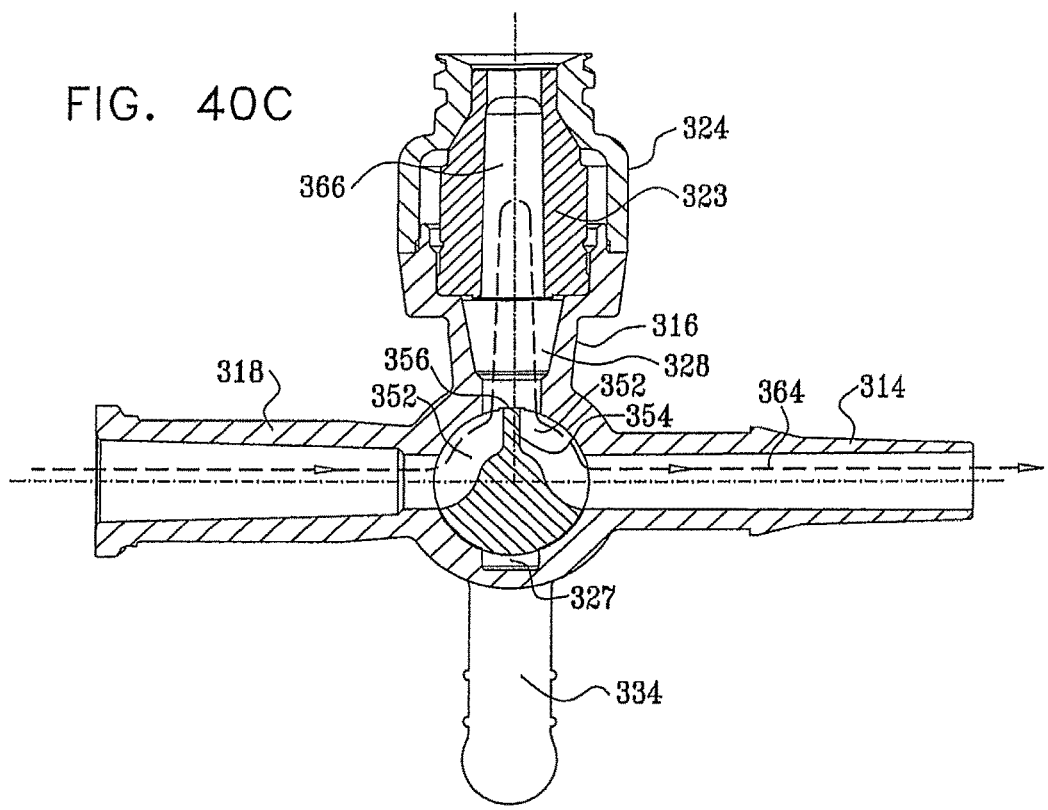

FIGS. 39C and 40C illustrate a third operating position of the stopcock of FIG. 31, which is typically employed for supplying a liquid to the patient from port 318 to port 314. Liquid flows via port 318 and partially peripherally-extending recess 352, around fluid flow guide 354, and into the internal volume 328 of port 316 as well as an internal volume 366 of the elastomeric element 323, flushing residual liquid therefrom, via port 314 to the patient, as indicated by an arrow 364.

It is a particular feature of the present invention that the provision of fluid flow guide 354 generally overcomes problems of the presence of residual liquids remaining in the internal volume 328 of port 316 as well as in internal volume 366 of the elastomeric element 323. This is important in various therapeutic situations. For example when blood is drawn from the patient through port 316, there remains residual blood in the internal volume 328 of port 316 and the internal volume 366 of the elastomeric element 323. This blood, if left in internal volumes 328 and 366 for a period of time, can clot and thus become dangerous if delivered to the patient. In addition, the coagulated blood could occlude the liquid passageway extending through port 316. Various infections could possibly arise as a result of the retained blood.

This feature is also useful when a medicament is supplied to a patient through port 316. If a portion of the medicament remains in the internal volumes 328 of port 316 and 366 of the elastomeric element 323, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament, from the internal volumes 328 and 366 and typically returning it to the patient without requiring the use of extra syringes and the opening of the medical set to the atmosphere, thereby increasing the chance of contamination.

Figure 39D:
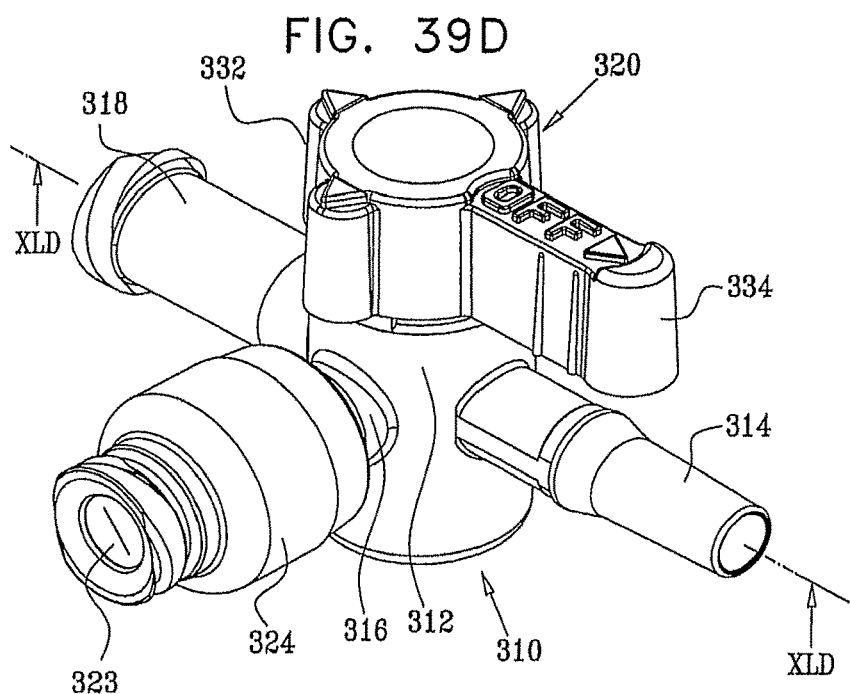
Figure 40D:
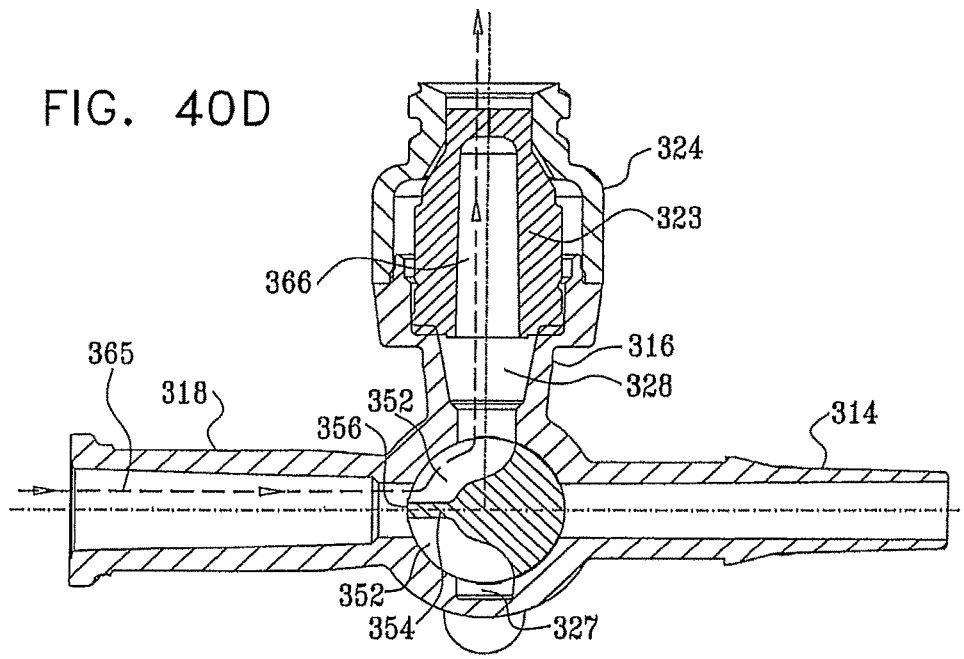

FIGS. 39D and 40D illustrate a fourth operating position of the stopcock of FIG. 31, which may be used for flushing the IV set upstream of the stopcock, when port 316 is open to the atmosphere as by insertion of a male luer connector, such as a syringe tip (not shown), into the elastomeric element 323 of the valve thereof. The insertion of the male luer connector activates the flow of liquid from port 318, around fluid flow guide 354 and through partially peripherally-extending recess 352, to the male luer connector via the elastomeric element 323 of port 316, as indicated by an arrow 365. Alternatively, this operating position may be employed for pushing liquid via the side port 316, through port 318, in a direction opposite arrow 365, for uses such as mixing liquid in the pressure bag.

Figure 41:
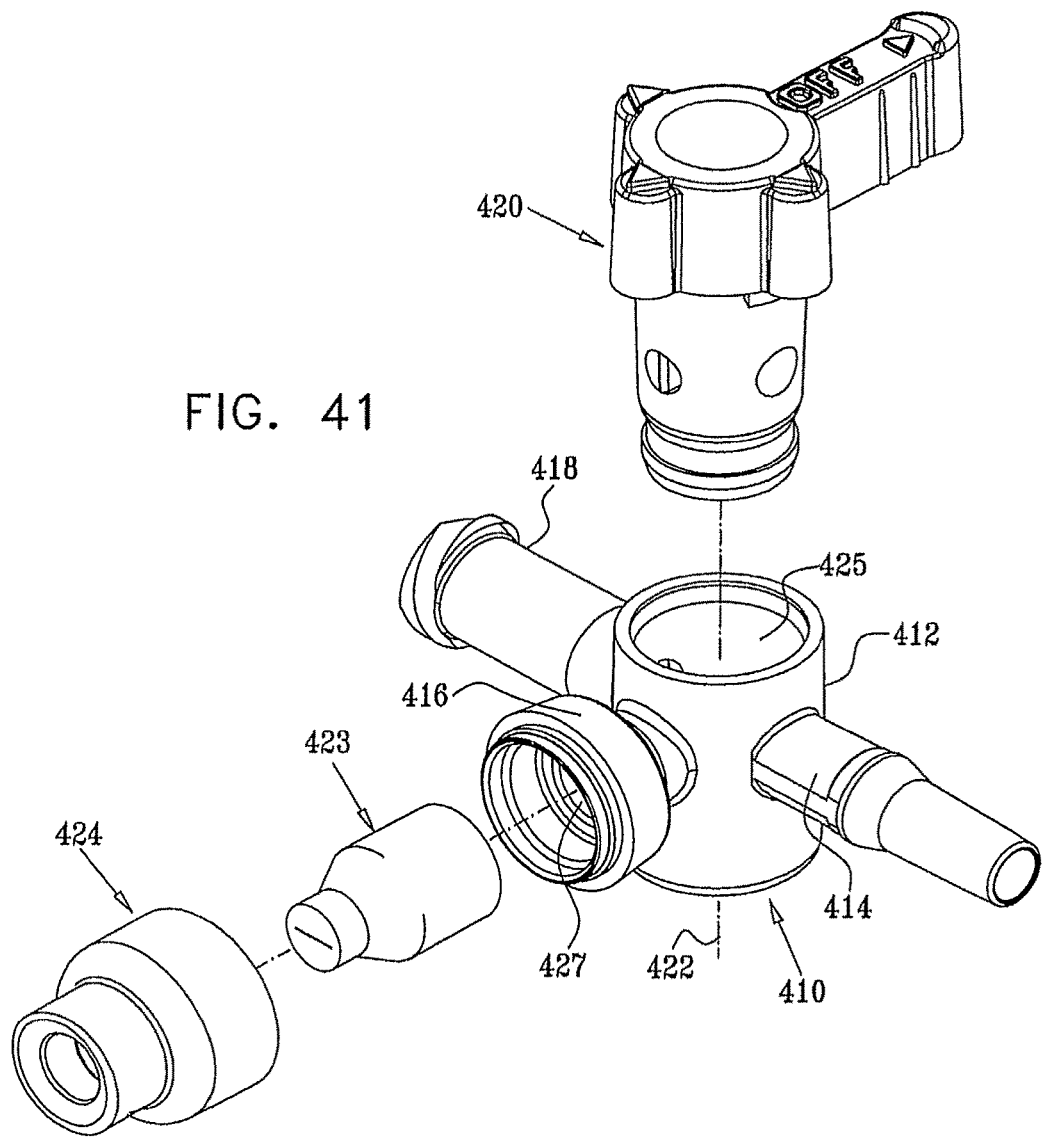
FIG. 41 is a simplified exploded view illustration of a stopcock constructed and operative in accordance with yet another preferred embodiment of the present invention.

Reference is now made to FIG. 41, which is an exploded view illustration of a stopcock constructed and operative in accordance with a preferred embodiment of the present invention. As seen in FIG. 41, the stopcock comprises a housing element 410 including a main tubular portion 412 and three side ports, designated by reference numerals 414, 416 and 418 respectively. A handle element 420 is arranged to be seated within main tubular portion 412 of housing element 410.

Figure 42:
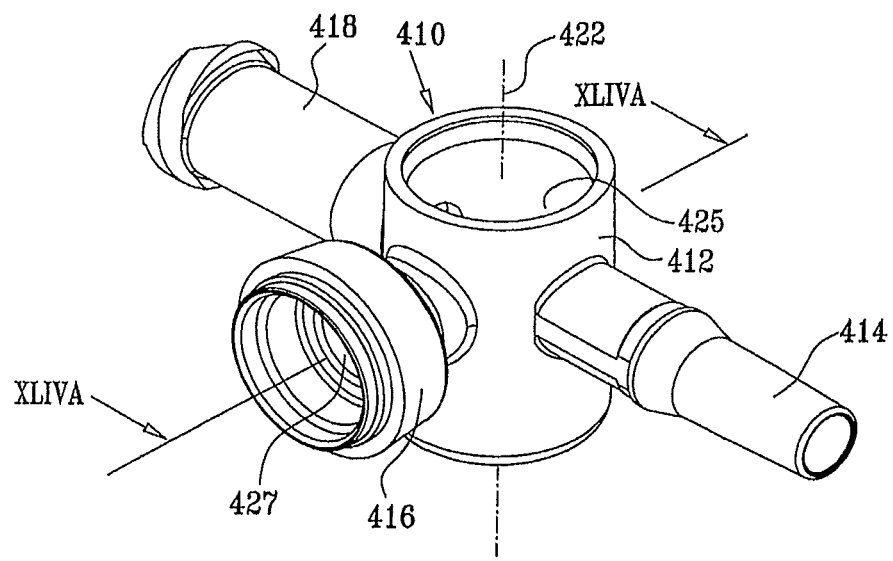
FIGS. 42 and 43 are simplified pictorial illustrations of a housing element, which forms part of the stopcock of FIG. 41 taken in two different directions.
Figure 43:
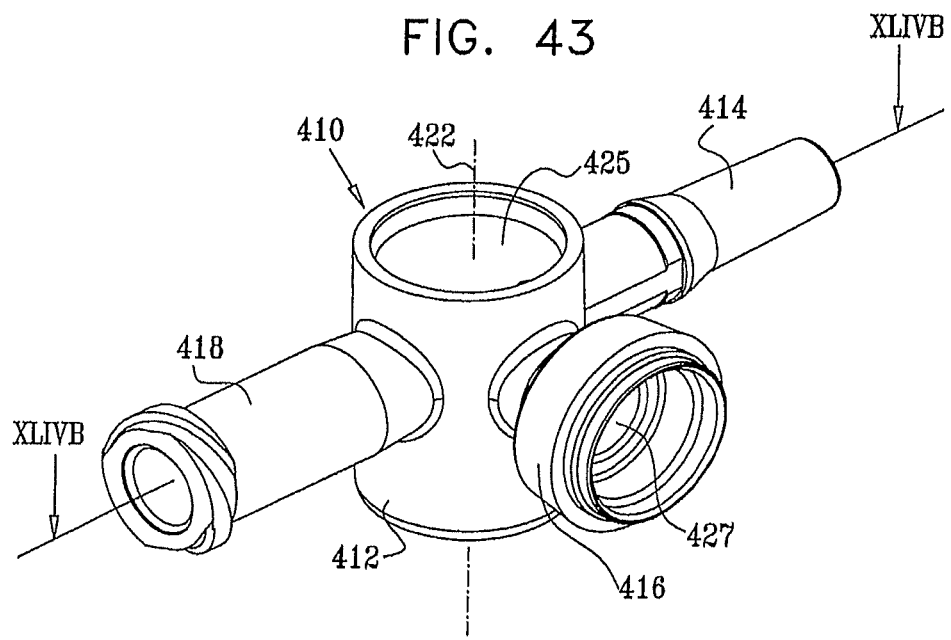
Figure 44A:
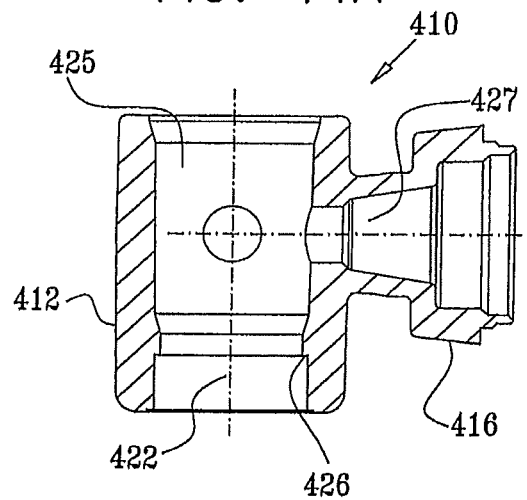
FIGS. 44A and 44B are sectional illustrations taken along section lines XLIVA-XLIVA and XLIVB-XLIVB in FIGS. 42 and 43, respectively.
Figure 44B:
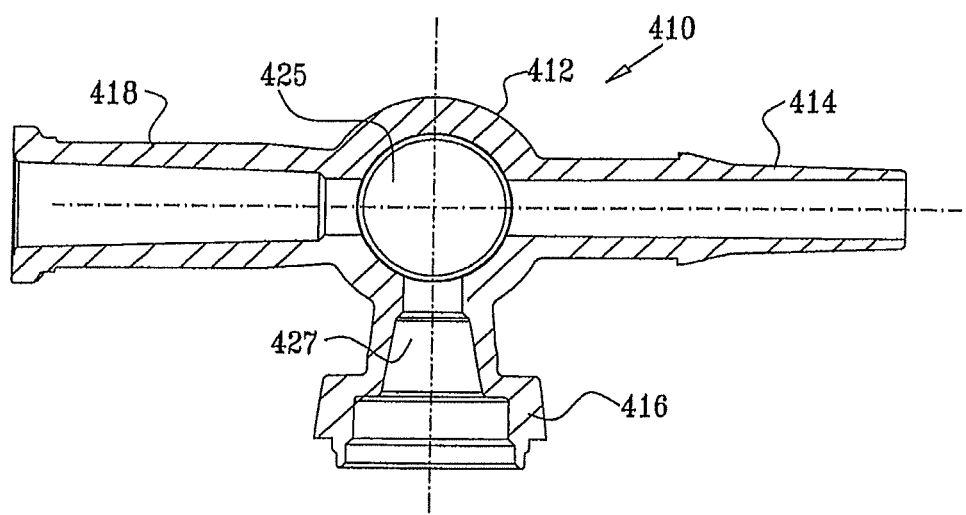

Reference is now made additionally to FIGS. 42 and 43 which are pictorial illustrations of housing element 410 and to FIGS. 44A and 44B which are sectional illustrations thereof. As seen in FIGS. 41-44B, tubular portion 412 of housing element 410 is generally cylindrical, arranged about an axis 422, and has side ports 414, 416 and 418 extending in different directions therefrom, typically separated by 90 degrees about axis 422. Port 414 is preferably a male port which preferably meets luer standard ISO 594-1, while port 416 incorporates a normally closed swabbable valve which is configured to receive a male luer and port 418 is preferably a female port, which preferably meets luer standard ISO 594-1. Conventional plugs, nuts and covers may be used in association with ports 414 and 418.

Port 416 of housing element 410 includes a valve employing an elastomeric element 423, held in place by a cap 424, which is welded or otherwise fixed to housing element 410.

Elastomeric element 423 and cap 424 are commercially available from Halkey-Roberts Corporation of St. Petersburg, Fla., USA and described in one or more of U.S. Pat. Nos. 6,651,956; 6,089,541 and 6,036,171, the disclosures of which are hereby incorporated by reference. Alternatively, valves and valve elements commercially available from other sources such as Becton-Dickinson, Cardinal, Medegen and Filtertek may be employed.

Tubular portion 412 includes a central bore 425 having a slightly conical configuration, which is formed with a circumferential undercut 426. Port 416 defines an internal volume 427.

Reference is now made to FIGS. 45A-48B, which illustrate handle element 420. As seen in FIGS. 45A-48B, the handle element includes a shaft portion 430, which is integrally formed with a top portion 432 from which extends a finger-engageable protrusion 434. It is appreciated that any other suitable general configuration of the top portion of the handle element may alternatively be employed.

Shaft portion 430 is generally symmetrical about a shaft axis 442 and has a slightly conical outer surface 444, typically having an angle α (as seen particularly in FIG. 46A) of 3-4 degrees, which corresponds to the slightly conical configuration of central bore 425 for rotatable sealing engagement therewith. As seen particularly in FIGS. 48A and 48B, shaft portion 430 is typically formed with mutually sealed top and bottom cylindrical recesses 446 and 448, which are sealingly separated by a divider 450.

Figure 45A:
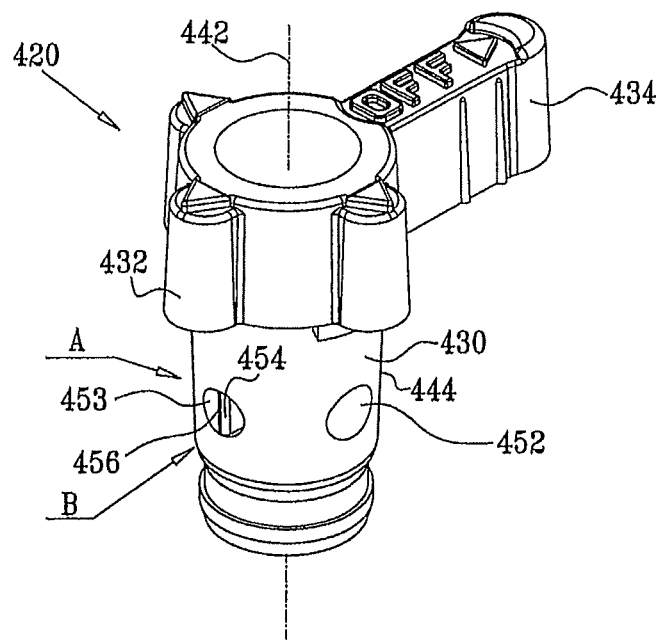
FIGS. 45A and 45B are simplified pictorial illustrations of a handle element which forms part of the stopcock of FIG. 41 in two operative orientations.
Figure 45B:
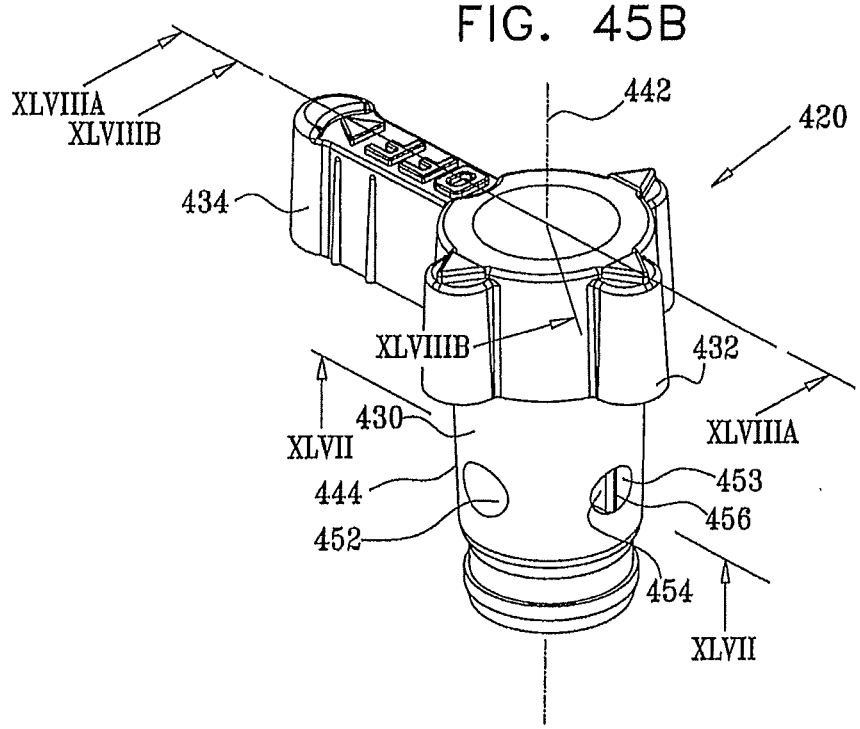
Figure 46A:
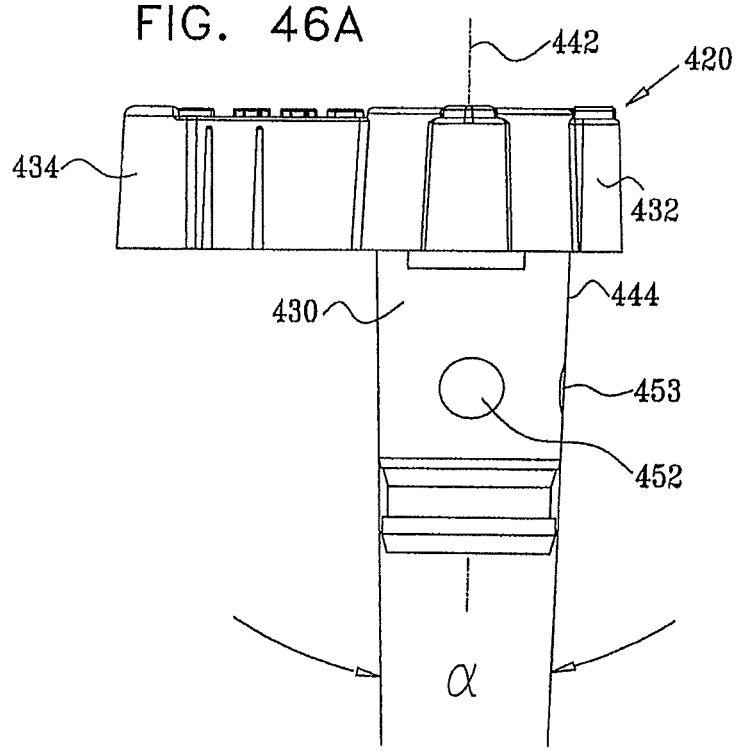
FIGS. 46A and 46B are simplified plan view illustrations of the handle element of FIGS. 45A and 45B taken along respective directions A and B in FIG. 45A.
Figure 46B:
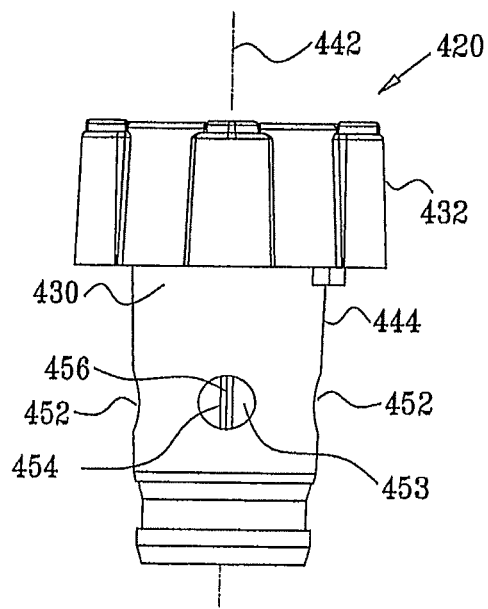
Figure 47:
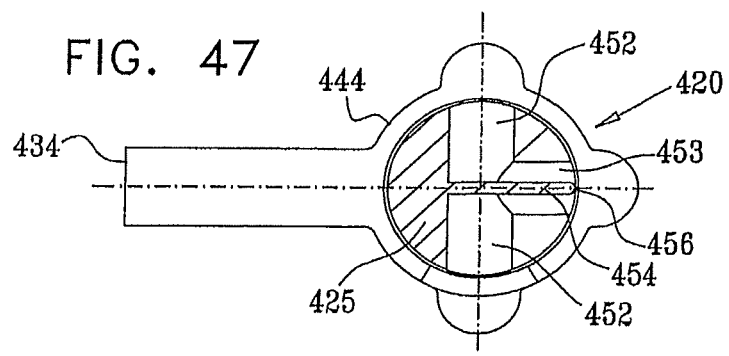
FIGS. 47, 48A and 48B are sectional illustrations taken along section lines XLVII-XLVII, XLVIIIA-XLVIIIA and XLVIIIB-XLVIIIB in FIG. 45B.
Figure 48A:
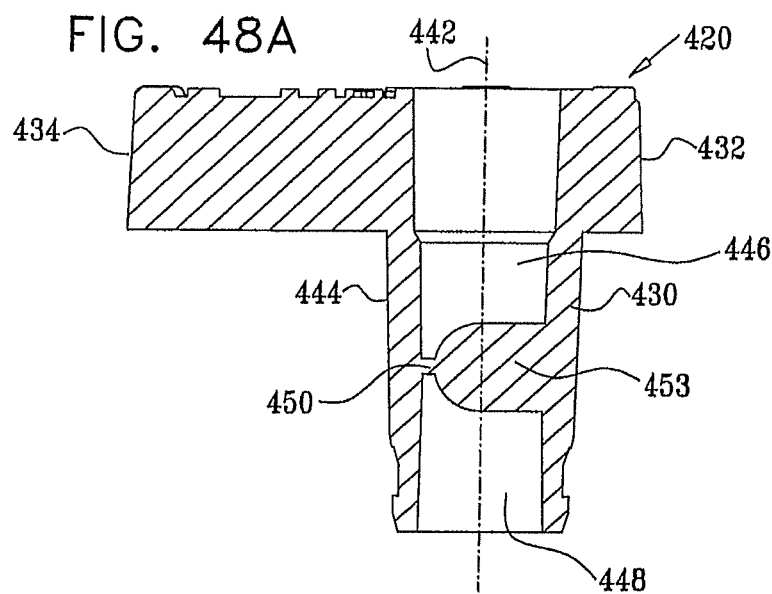
Figure 48B:
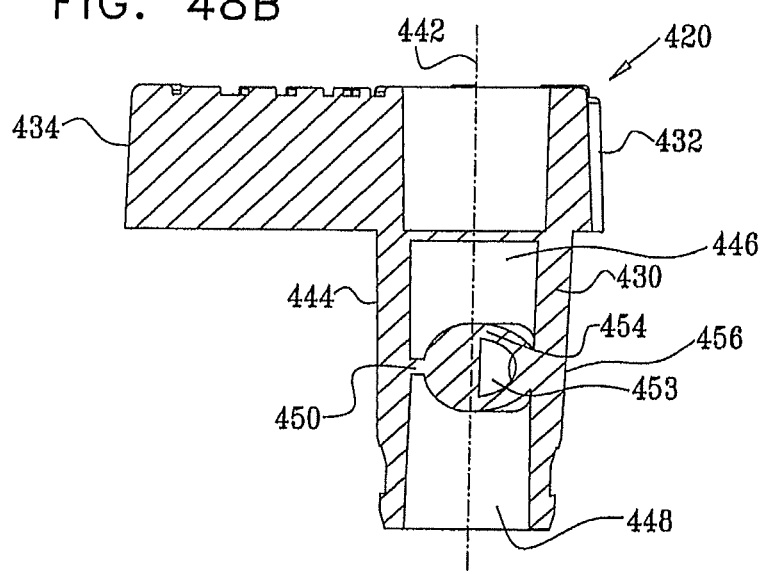

Disposed generally between recesses 446 and 448 and sealed therefrom is a side-to-side extending bore 452 and a side bore 453 extending perpendicularly with respect thereto and communicating therewith. Bore 452 and side bore 453 are bifurcated by a fluid flow guide 454 in such a manner that fluid communication between opposite ends of bore 452 takes place via side bore 453. Bores 452 and 453 and fluid flow guide 454 define a fluid flow passageway between selectable ones of side ports 414, 416 and 418 depending on the rotational orientation of the handle element 420 relative to the housing element 410. Fluid flow guide 454 directs the flow of liquid between ports 414 and 418 through bores 452 and 453 into the internal volume 427 of port 416 for flushing thereof, when the handle element 420 is suitably positioned. The radially outward facing edge 456 of fluid flow guide 454 is formed with a suitably tapered configuration in order to prevent liquid flow therepast when fluid flow guide 454 is not located opposite a port as shown in FIG. 45A, alternatively it may have many other shapes.

Reference is now made to FIGS. 49A, 49B, 49C and 49D, which are simplified pictorial illustrations of the stopcock of FIG. 41 in four operative orientations and to FIGS. 50A, 50B, 50C and 50D, which are sectional illustrations of the stopcock of FIGS. 49A, 49B, 49C and 49D, respectively.

Figure 49A:
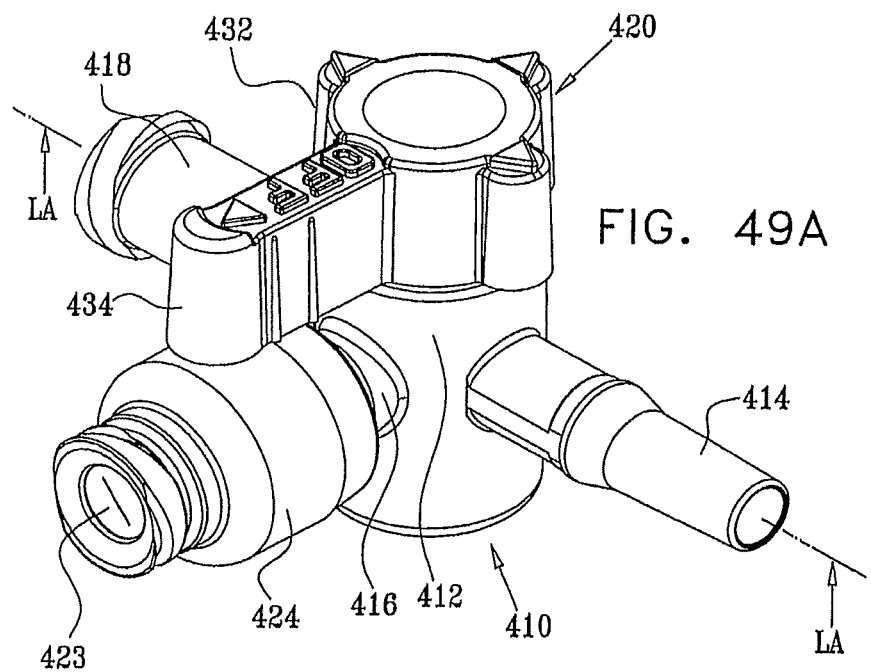
FIGS. 49A, 49B, 49C and 49D are simplified pictorial illustrations of the stopcock of FIG. 41 in four operative orientations.
Figure 50A:
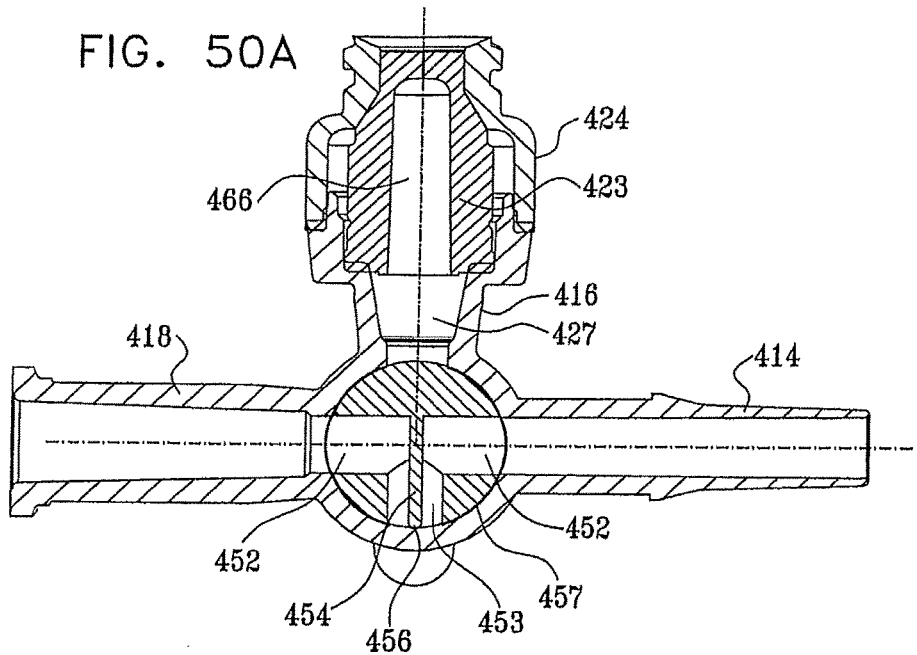

FIGS. 49A and 50A illustrate a first operating position of the stopcock of FIG. 41. As seen, there is no fluid communication between any of the ports. Liquid does not flow from port 418 to port 414, because it is blocked by fluid flow guide 454, whose edge 456 sealingly engages an inner facing wall 457 of central bore 425 of housing element 410. This orientation may be utilized to close all three ports.

The operative orientation shown in FIGS. 49A and 50A may be advantageously employed when it is desired to prevent all flow of liquid through the stopcock. The procedure currently used requires careful placement of the handle to an angle 45 degrees from one of the ports. Such a procedure is unreliable and requires careful attention of the operator, which may be a doctor or a nurse in the middle of a surgery.

Figure 49B:
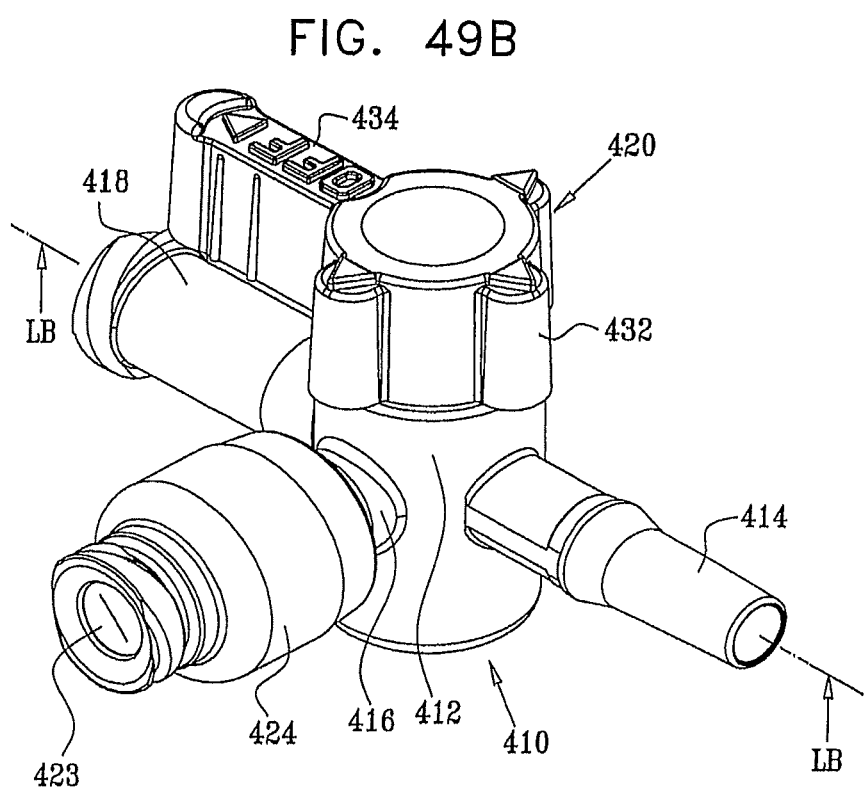
Figure 50B:
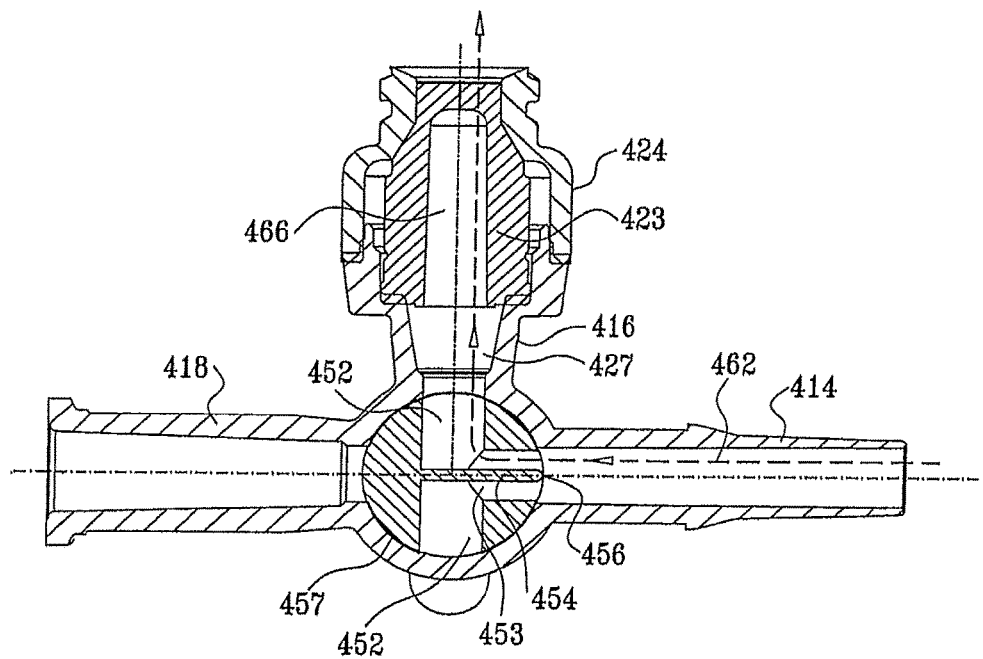

FIGS. 49B and 50B illustrate a second operating position of the stopcock of FIG. 41, which is typically employed for drawing blood or other fluids from the patient. The user typically connects a syringe to port 416 and draws blood from the patient through port 414 and bores 453 and 452 through port 416 to the syringe, as indicated by an arrow 462. It is appreciated that this operating position may also be used for supplying a medicament to the patient when port 418 is closed, in a flow direction opposite to that indicated by arrow 462.

Figure 49C:
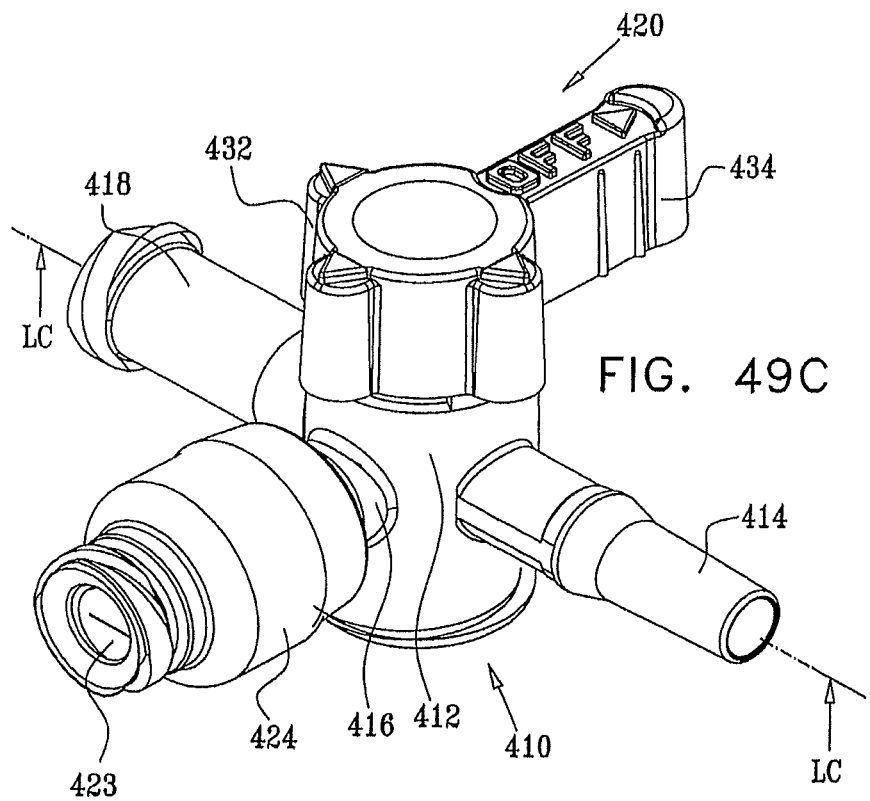

FIGS. 49C and 50C illustrate a third operating position of the stopcock of FIG. 41, which is typically employed for supplying a liquid to the patient from port 418 to port 414. Liquid flows via port 418 and bores 452 and 453, around fluid flow guide 454, and into the internal volume 427 of port 416 as well as an internal volume 466 of the elastomeric element 423, flushing residual liquid therefrom, via port 414 to the patient, as indicated by an arrow 464.

It is a particular feature of the present invention that the provision of fluid flow guide 454 generally overcomes problems of the presence of residual liquids remaining in the internal volume 427 of port 416 as well as in internal volume 466 of the elastomeric element 423. This is important in various therapeutic situations. For example when blood is drawn from the patient through port 416, there remains residual blood in the internal volume 427 of port 416 and the internal volume 466 of the elastomeric element 423. This blood, if left in internal volumes 427 and 466 for a period of time, can clot and thus become dangerous if delivered to the patient. In addition, the coagulated blood could occlude the liquid passageway extending through port 416. Various infections could possibly arise as a result of the retained blood.

This feature is also useful when a medicament is supplied to a patient through port 416. If a portion of the medicament remains in the internal volumes 427 of port 416 and 466 of the elastomeric element 423, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 427 and 466 and typically returning it to the patient without requiring the use of extra syringes and the opening of the medical set to the atmosphere, thereby increasing the chance of contamination.

Figure 49D:
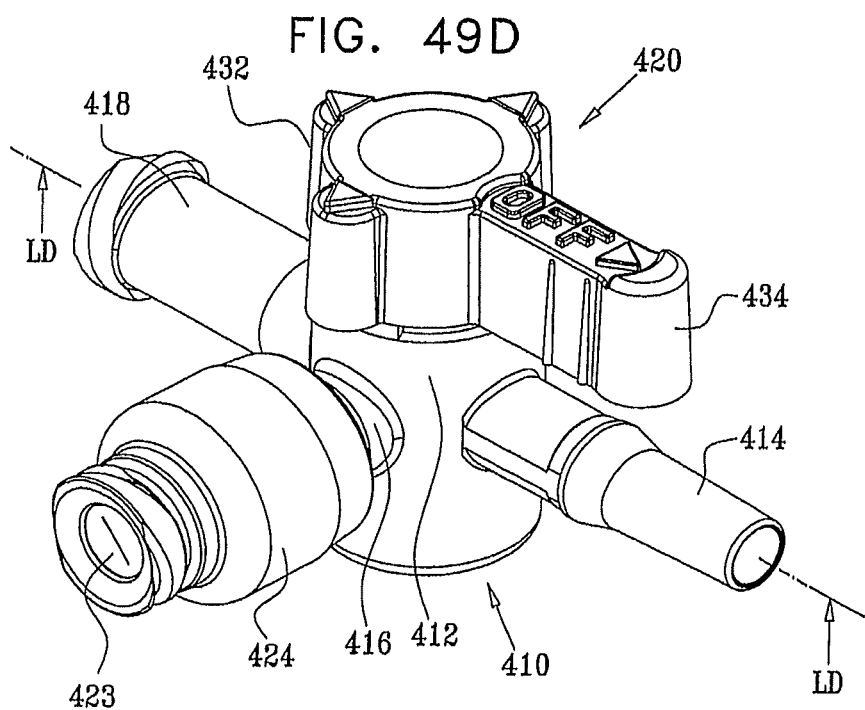

FIGS. 49D and 50D illustrate a fourth operating position of the stopcock of FIG. 41, which may be used for flushing the IV set upstream of the stopcock, when port 416 is open to the atmosphere as by insertion of a male luer connector, such as a syringe tip (not shown), into the elastomeric element 423 of the valve thereof. The insertion of the male luer connector activates the flow of liquid from port 418, around fluid flow guide 454 and through bores 453 and 452, to the male luer connector via the elastomeric element 423 of port 416, as indicated by an arrow 465. Alternatively, this operating position may be employed for pushing liquid via the side port 416, through port 418, in a direction opposite arrow 465, for uses such as mixing liquid in the pressure bag.

Figure 51:
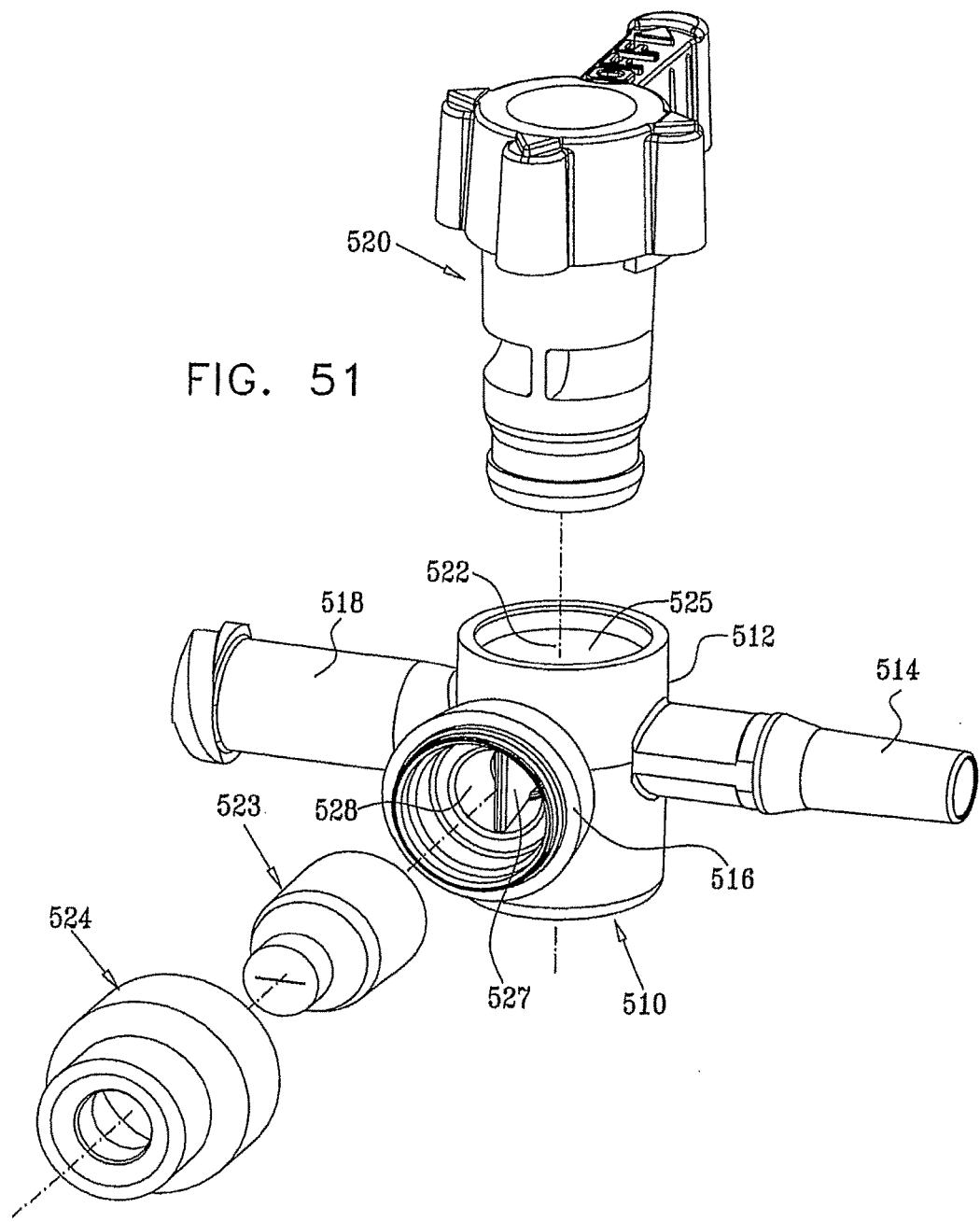
FIG. 51 is a simplified exploded view illustration of a stopcock constructed and operative in accordance with a further preferred embodiment of the present invention.

Reference is now made to FIG. 51, which is an exploded view illustration of a stopcock constructed and operative in accordance with a preferred embodiment of the present invention. As seen in FIG. 51, the stopcock comprises a housing element 510 including a main tubular portion 512 and three side ports, designated by reference numerals 514, 516 and 518 respectively. A handle element 520 is arranged to be seated within main tubular portion 512 of housing element 510.

Figure 52:
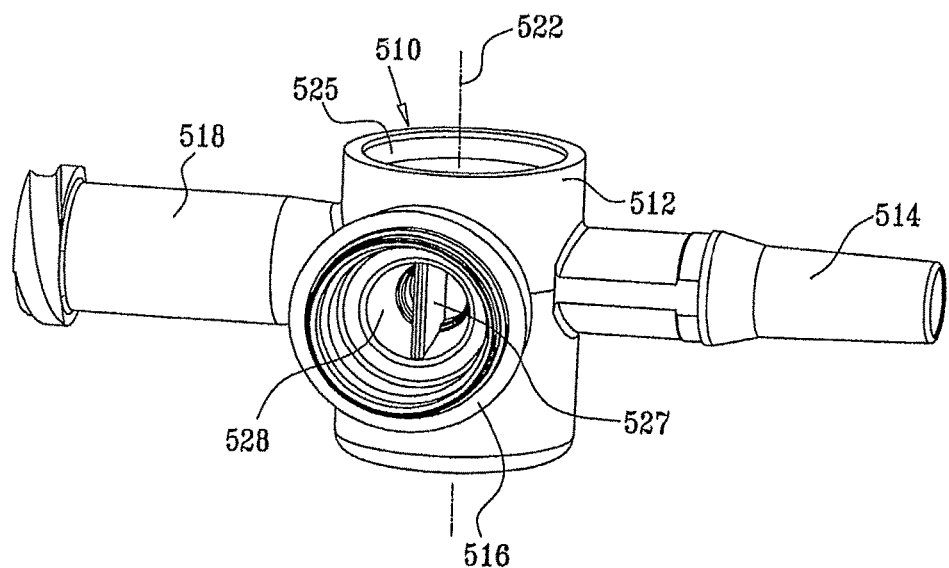
FIGS. 52 and 53 are simplified pictorial illustrations of a housing element, which forms part of the stopcock of FIG. 51 taken in two different directions.
Figure 53:
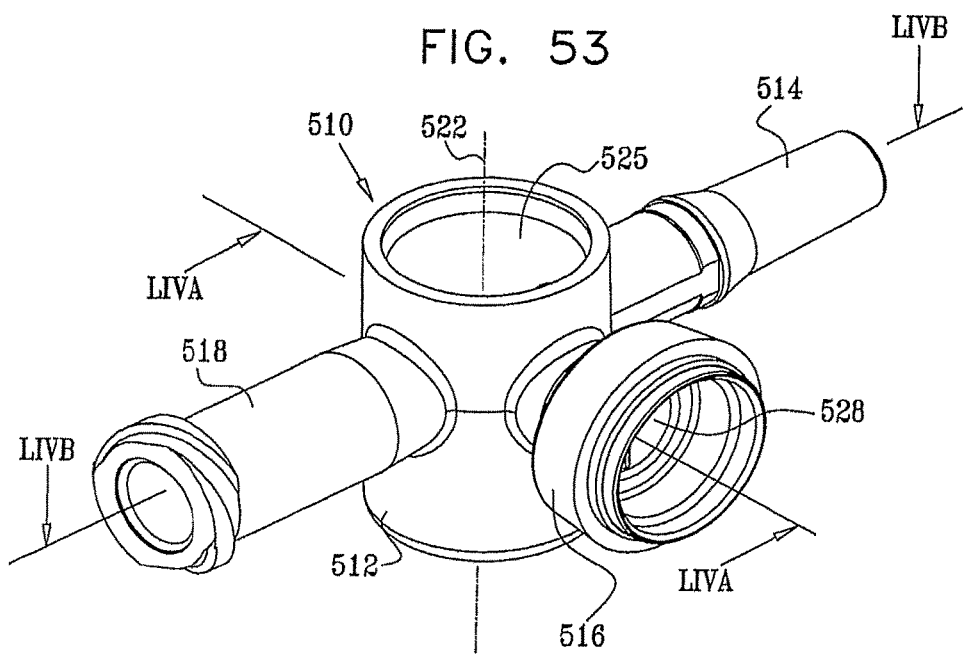
Figure 54A:
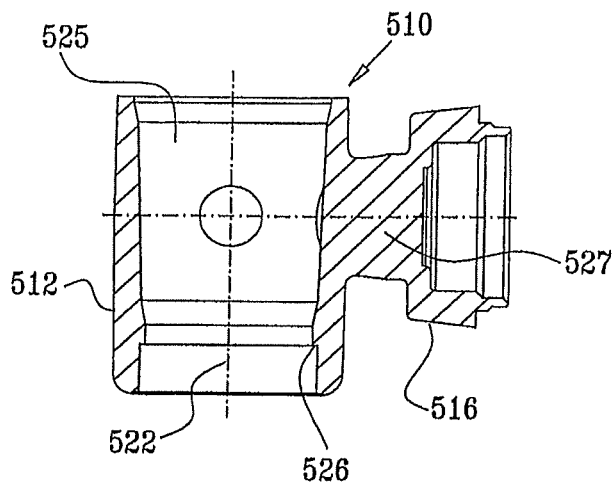
FIGS. 54A and 54B are sectional illustrations taken along section lines LIVA-LIVA and LIVB-LIVB in FIG. 53.
Figure 54B:
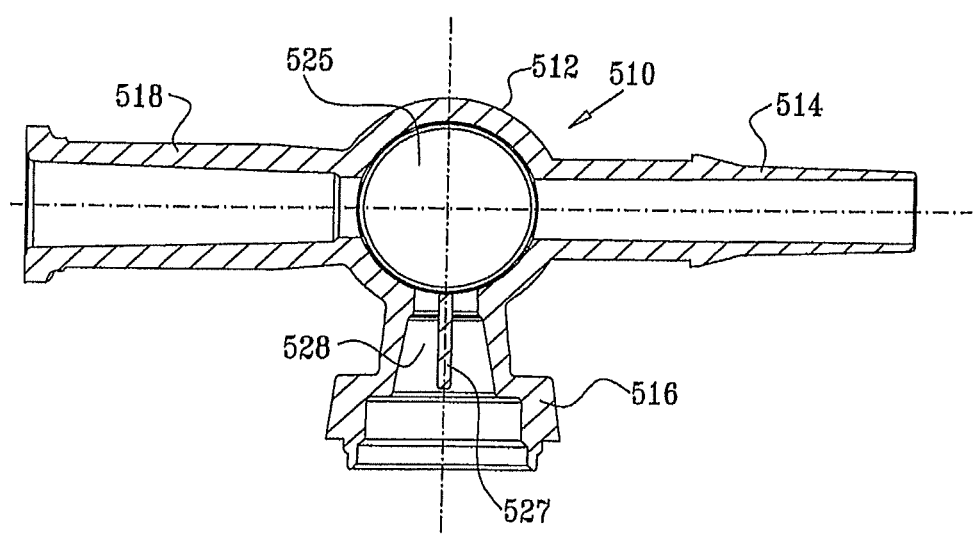

Reference is now made additionally to FIGS. 52 and 53 which are pictorial illustrations of housing element 510 and to FIGS. 54A and 54B which are sectional illustrations thereof. As seen in FIGS. 51-54B, tubular portion 512 of housing element 510 is generally cylindrical, arranged about an axis 522, and has side ports 514, 516 and 518 extending in different directions therefrom, typically separated by 90 degrees about axis 522. Port 514 is preferably a male port which preferably meets luer standard ISO 594-1, while port 516 incorporates a normally closed swabbable valve which is configured to receive a male luer and port 518 is preferably a female port, which preferably meets luer standard ISO 594-1. Conventional plugs, nuts and covers may be used in association with ports 514 and 518.

Port 516 of housing element 510 includes a valve employing an elastomeric element 523, held in place by a cap 524, which is welded or otherwise fixed to housing element 510. Elastomeric element 523 and cap 524 are commercially available from Halkey-Roberts Corporation of St. Petersburg, Fla., USA and described in one or more of U.S. Pat. Nos. 6,651,956; 6,089,541 and 6,036,171, the disclosures of which are hereby incorporated by reference. Alternatively, valves and valve elements commercially available from other sources such as Becton-Dickinson, Cardinal, Medegen and Filtertek may be employed.

Tubular portion 512 includes a central bore 525 having a slightly conical configuration, which is formed with a circumferential undercut 526. Between bore 525 and elastomeric element 523, port 516 is bifurcated by a fluid flow guide 527. Port 516 defines an internal volume 528.

Reference is now made to FIGS. 55A-58B, which illustrate handle element 520. As seen in FIGS. 55A-58B, the handle element includes a shaft portion 530, which is integrally formed with a top portion 532 from which extends a finger-engageable protrusion 534. It is appreciated that any other suitable general configuration of the top portion of the handle element may alternatively be employed.

Shaft portion 530 is generally symmetrical about a shaft axis 542 and has a slightly conical outer surface 544, typically having an angle α (as seen particularly in FIG. 56A) of 3-4 degrees, which corresponds to the slightly conical configuration of central bore 525 for rotatable sealing engagement therewith. As seen particularly in FIGS. 58A and 58B, shaft portion 530 is typically formed with mutually sealed top and bottom cylindrical recesses 546 and 548, which are sealingly separated by a divider 550.

Figure 55A:
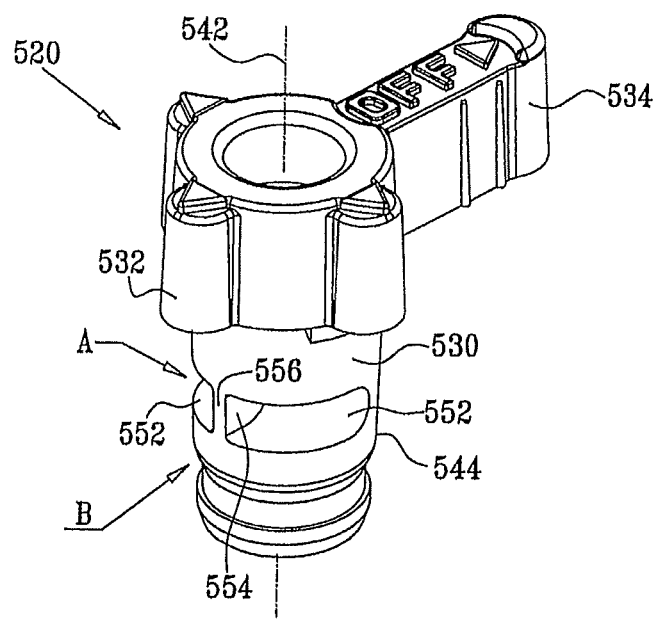
FIGS. 55A and 55B are simplified pictorial illustrations of a handle element which forms part of the stopcock of FIG. 51 in two operative orientations.
Figure 55B:
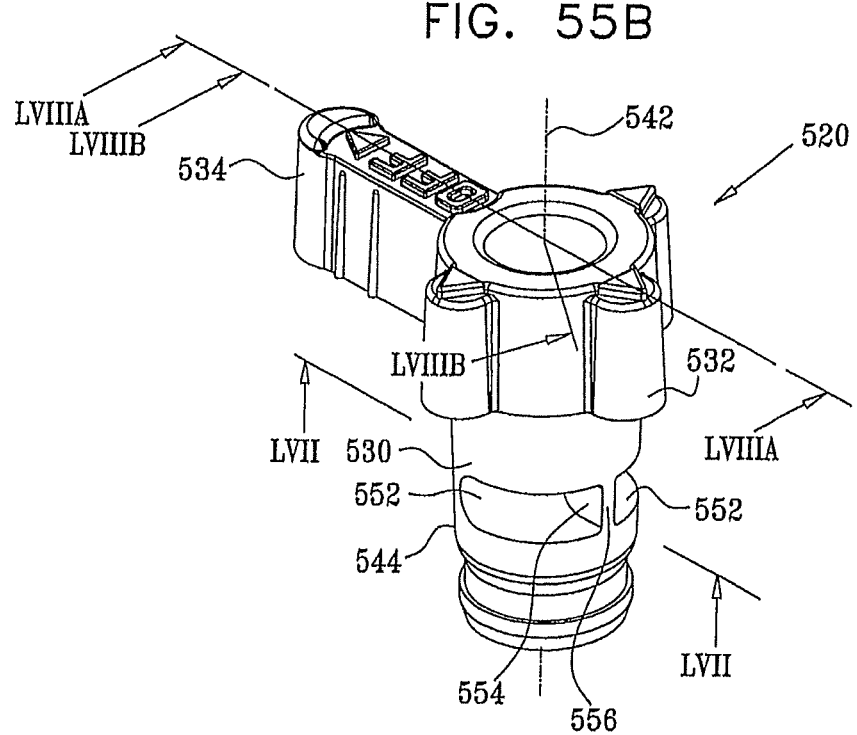
Figure 56A:
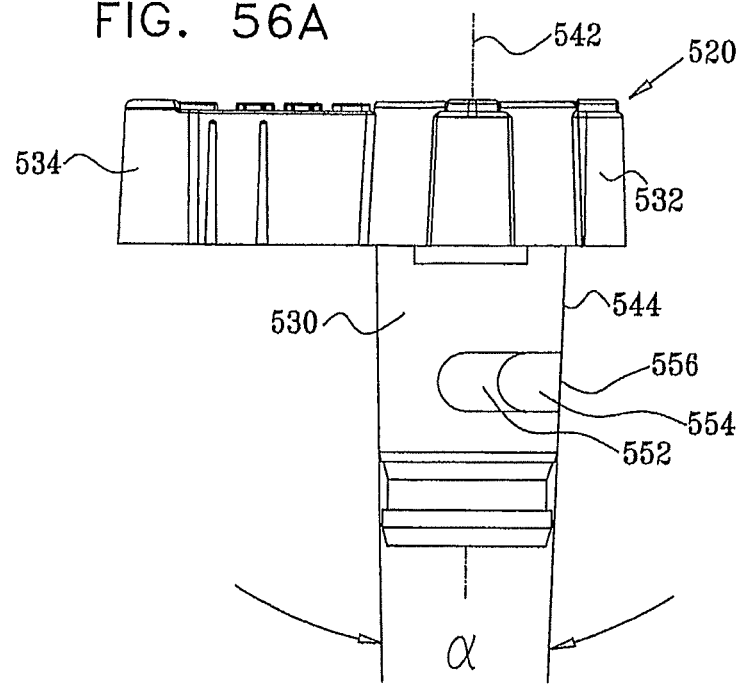
FIGS. 56A and 56B are simplified plan view illustrations of the handle element of FIGS. 55A and 55B taken along respective directions A and B in FIG. 55A.
Figure 56B:
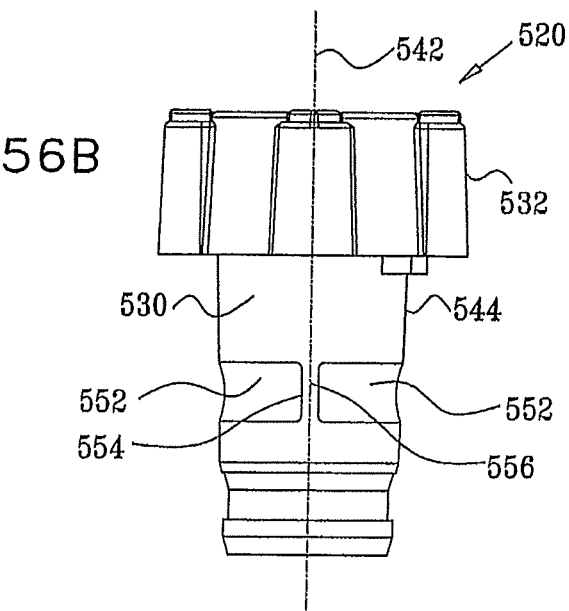
Figure 57:
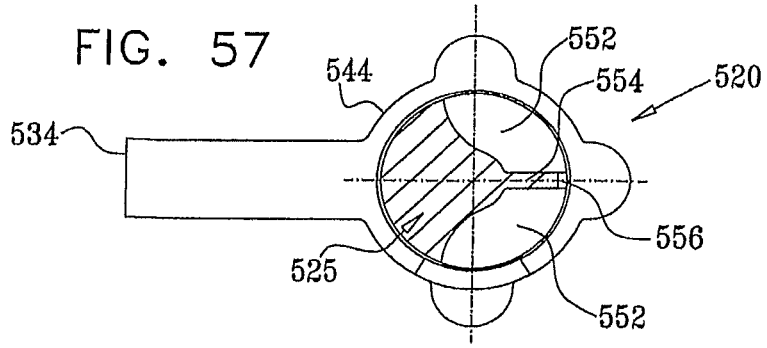
FIGS. 57, 58A and 58B are sectional illustrations taken along section lines LVII-LVII, LVIIIA-LVIIIA and LVIIIB-LVIIIB in FIG. 55B.
Figure 58A:
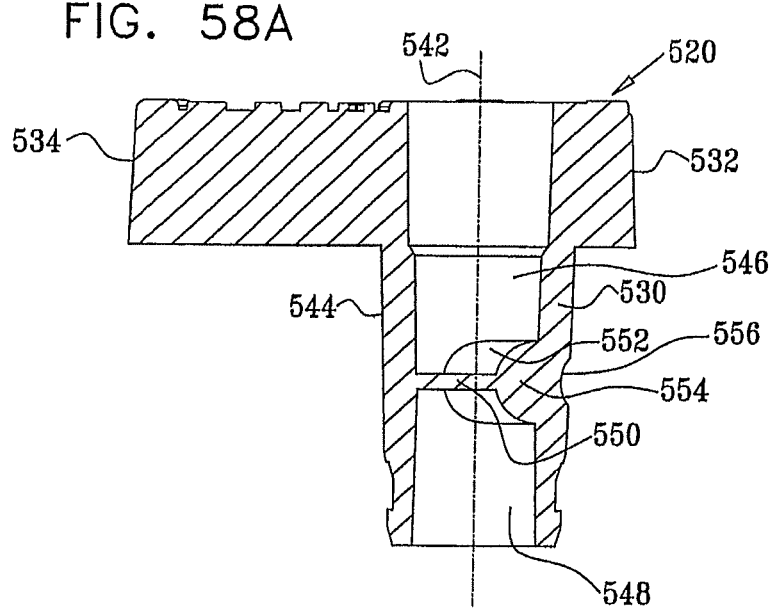
Figure 58B:
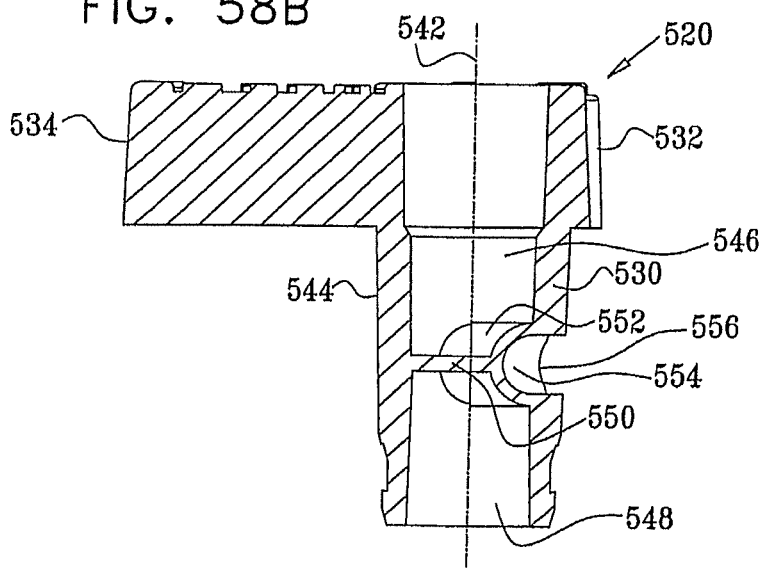

Disposed generally between recesses 546 and 548 and sealed therefrom is a partially peripherally-extending recess 552, selectably defining a fluid flow passageway between selectable ones of side ports 514, 516 and 518 depending on the rotational orientation of the handle element 520 relative to the housing element 510. Preferably extending radially and partially bifurcating the recess 552 is a fluid flow guide 554, which directs the flow of liquid between ports 514 and 518 through the passageway defined by recess 552 into the internal volume 528 of port 516 for flushing thereof, when the handle element 520 is suitably positioned. The radially outward facing edge 556 of fluid flow guide 554 is formed with a suitably tapered configuration in order to prevent liquid flow therepast when fluid flow guide 554 is not located opposite a port as shown in FIG. 55A, alternatively it may have many other shapes.

Reference is now made to FIGS. 59A, 59B, 59C and 59D, which are simplified pictorial illustrations of the stopcock of FIG. 51 in four operative orientations and to FIGS. 60A, 60B, 60C and 60D, which are sectional illustrations of the stopcock of FIGS. 59A, 59B, 59C and 59D, respectively.

Figure 59A:
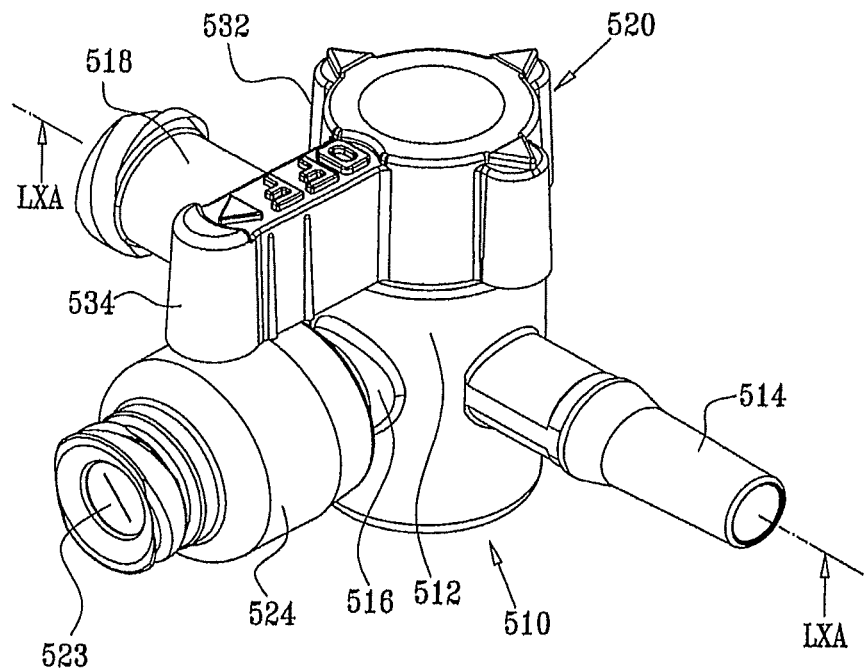
FIGS. 59A, 59B, 59C and 59D are simplified pictorial illustrations of the stopcock of FIG. 51 in four operative orientations.
Figure 60A:
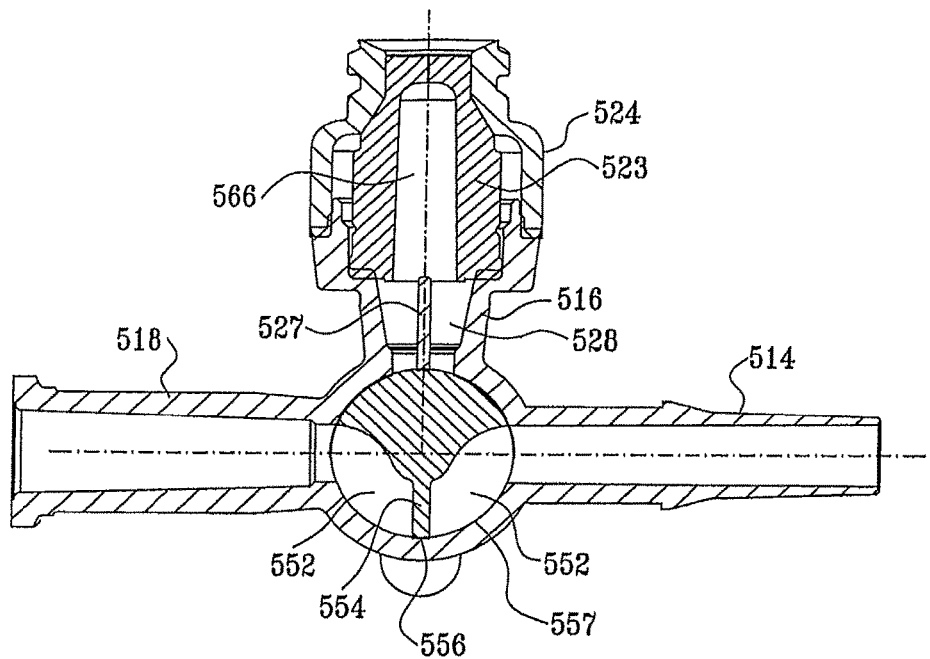
FIGS. 60A, 60B, 60C and 60D are sectional illustrations taken along section lines LXA-LXA, LXB-LXB, LXC-LXC and LXD-LXD in FIGS. 59A, 59B, 59C and 59D respectively.

FIGS. 59A and 60A illustrate a first operating position of the stopcock of FIG. 51. As seen, there is no fluid communication between any of the ports. Liquid does not flow from port 518 to port 514, because it is blocked by fluid flow guide 554, whose edge 556 sealingly engages an inner facing wall 557 of bore 525 of housing element 510. This orientation may be utilized to close all three ports.

The operative orientation shown in FIGS. 59A and 60A may be advantageously employed when it is desired to prevent all flow of liquid through the stopcock. The procedure currently used requires careful placement of the handle to an angle 45 degrees from one of the ports. Such a procedure is unreliable and requires careful attention of the operator, which may be a doctor or a nurse in the middle of a surgery.

Figure 59B:
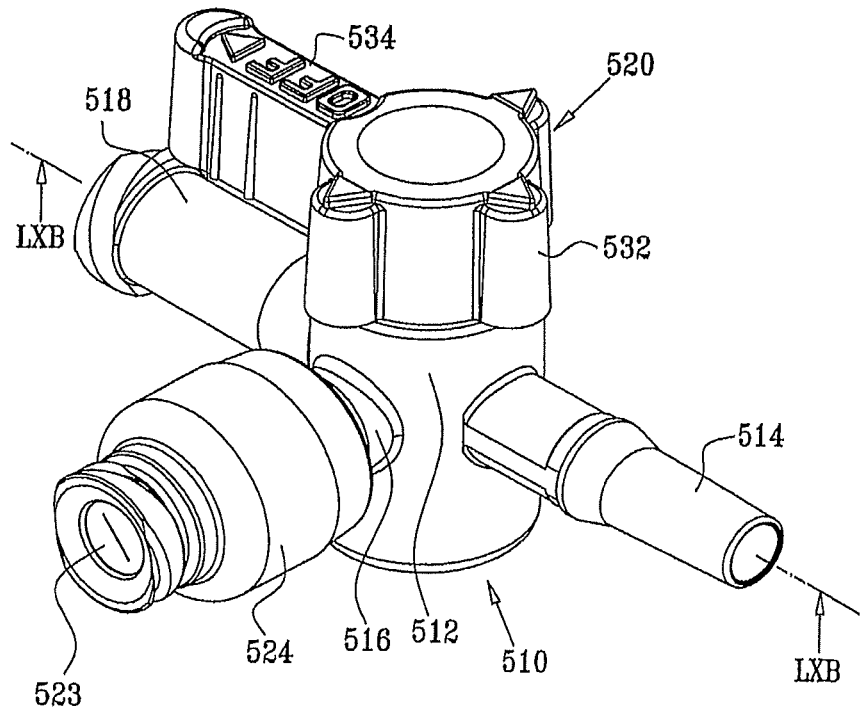
Figure 60B:
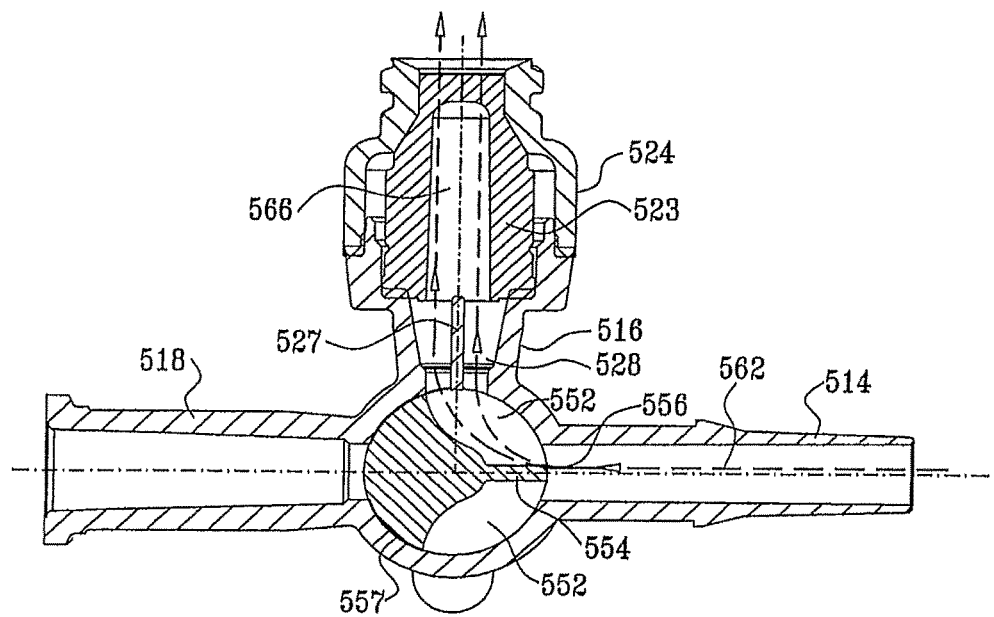

FIGS. 59B and 60B illustrate a second operating position of the stopcock of FIG. 51, which is typically employed for drawing blood or other fluids from the patient. The user typically connects a syringe to port 516 and draws blood from the patient through port 514 and partially peripherally-extending recess 552 through port 516 to the syringe, as indicated by an arrow 562. It is appreciated that this operating position may also be used for supplying a medicament to the patient when port 518 is closed, in a flow direction opposite to that indicated by arrow 562.

Figure 59C:
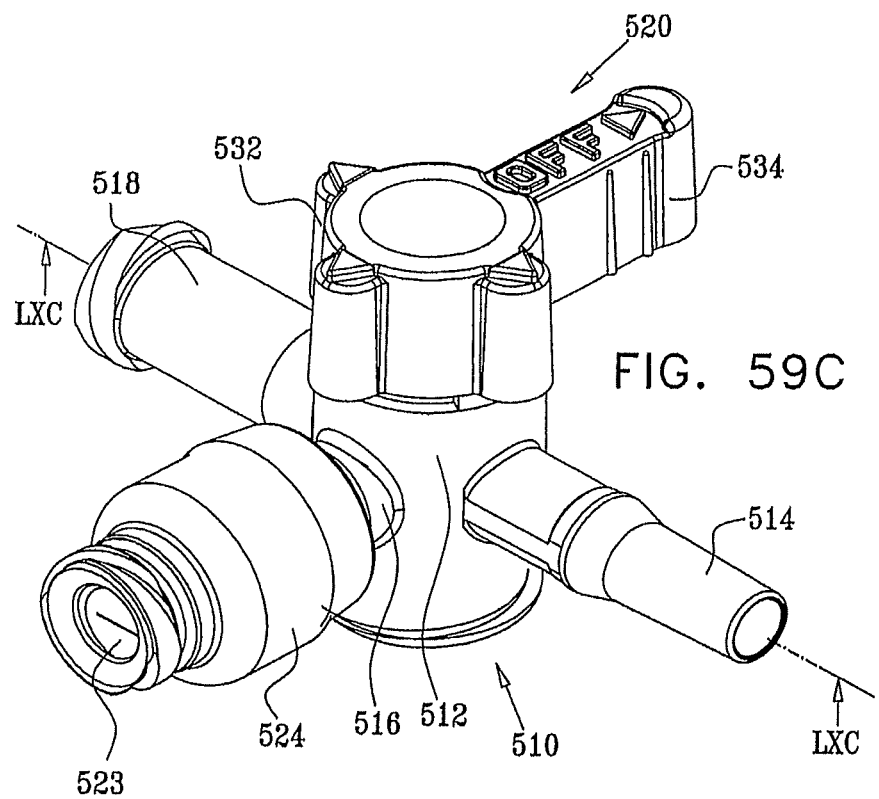
Figure 60C:
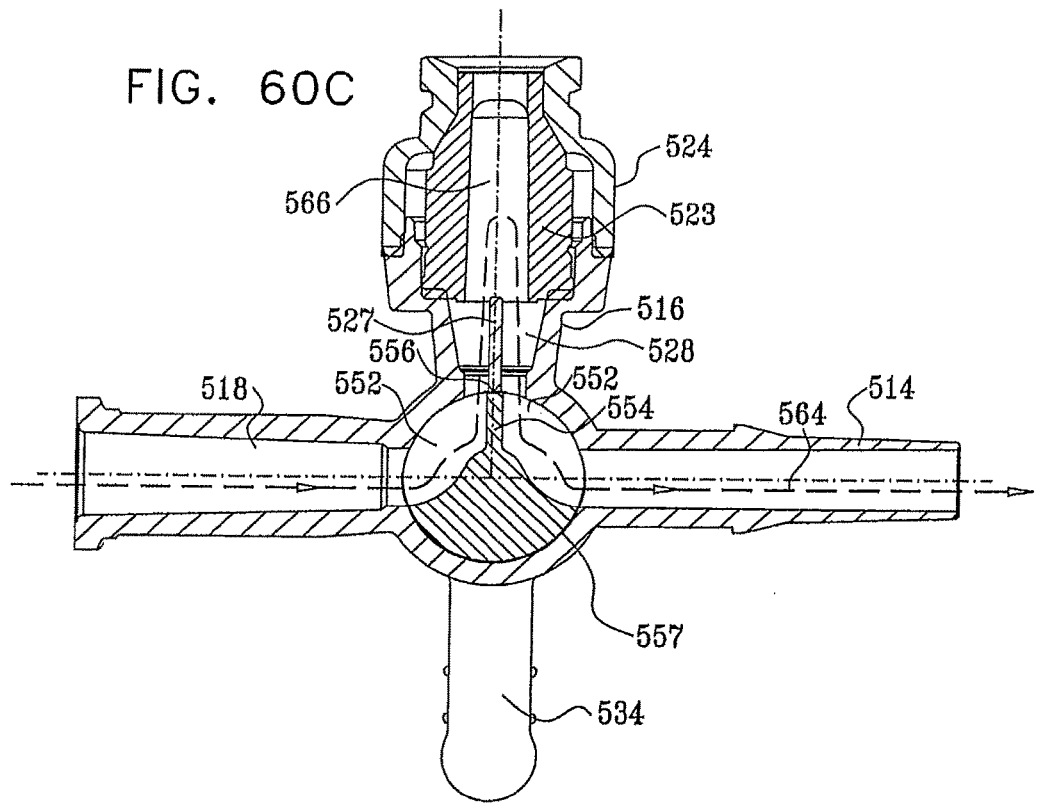

FIGS. 59C and 60C illustrate a third operating position of the stopcock of FIG. 51, which is typically employed for supplying a liquid to the patient from port 518 to port 514. Liquid flows via port 518 and partially peripherally-extending recess 552, along fluid flow guides 554 and 527, and into the internal volume 528 of port 516 as well as an internal volume 566 of the elastomeric element 523, flushing residual liquid therefrom, via port 514 to the patient, as indicated by an arrow 564.

It is a particular feature of the present invention that the provision of fluid flow guides 554 and 527 generally overcomes problems of the presence of residual liquids remaining in the internal volume 528 of port 516 as well as in internal volume 566 of the elastomeric element 523. This is important in various therapeutic situations. For example when blood is drawn from the patient through port 516, there remains residual blood in the internal volume 528 of port 516 and the internal volume 566 of the elastomeric element 523. This blood, if left in internal volumes 528 and 566 for a period of time, can clot and thus become dangerous if delivered to the patient. In addition, the coagulated blood could occlude the liquid passageway extending through port 516. Various infections could possibly arise as a result of the retained blood.

This feature is also useful when a medicament is supplied to a patient through port 516. If a portion of the medicament remains in the internal volumes 528 of port 516 and 566 of the elastomeric element 523, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 528 and 566 and typically returning it to the patient without requiring the use of extra syringes and the opening of the medical set to the atmosphere, thereby increasing the chance of contamination.

Figure 59D:
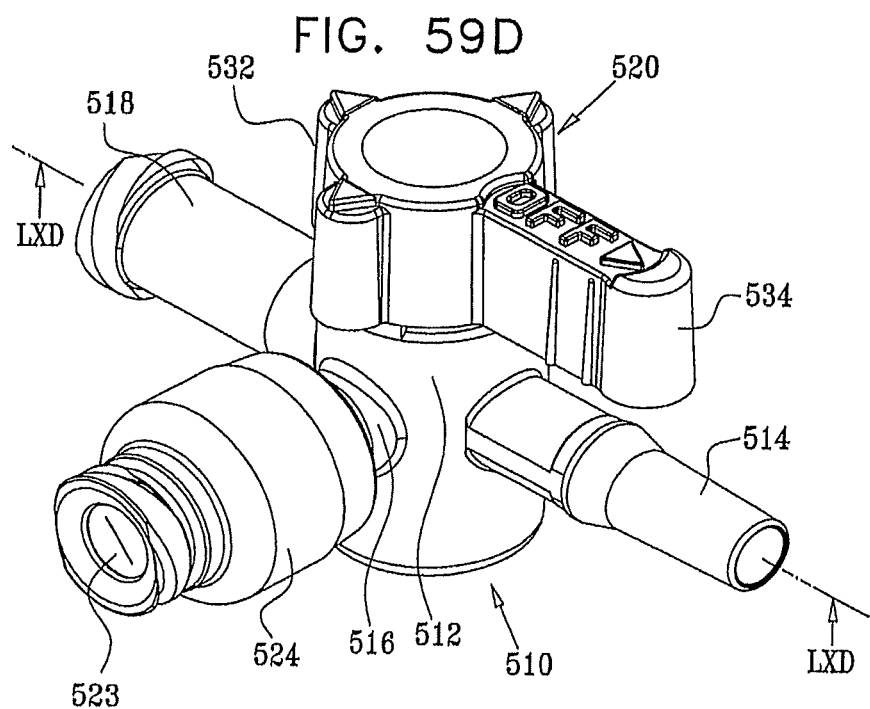
Figure 60D:
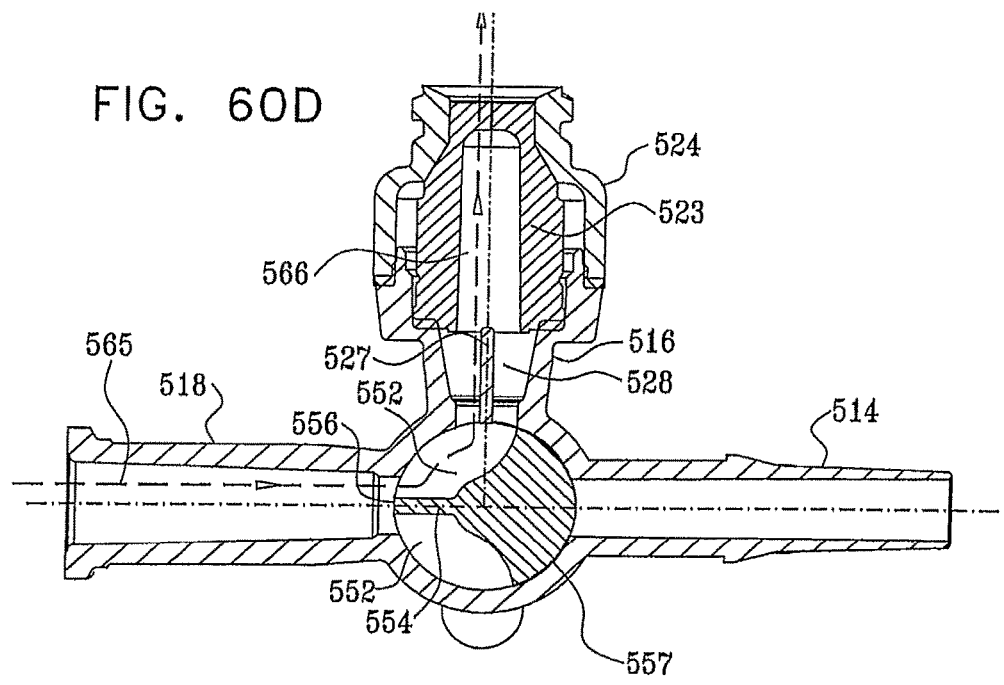

FIGS. 59D and 60D illustrate a fourth operating position of the stopcock of FIG. 51, which may be used for flushing the IV set upstream of the stopcock, when port 516 is open to the atmosphere as by insertion of a male luer connector, such as a syringe tip (not shown), into the elastomeric element 523 of the valve thereof. The insertion of the male luer connector activates the flow of liquid from port 518, around fluid flow guide 554 and through partially peripherally-extending recess 552, to the male luer connector via the elastomeric element 523 of port 516, as indicated by an arrow 565. Alternatively, this operating position may be employed for pushing liquid via the side port 516, through port 518, in a direction opposite arrow 565, for uses such as mixing liquid in the pressure bag.

Reference is now made to FIGS. 61A, 61B and 61C, which are simplified pictorial illustrations of an arterial monitoring set constructed and operative in accordance with a preferred embodiment of the present invention in various operative orientations. The arterial monitoring set includes a fluid-filled bag 612 and a tube portion 614 leading to a patient's artery. An arterial pressure sensor 616, which is schematically depicted in drawings 61A-61C, is coupled in a series along tube portion 614 and provides a visible output on a conventional monitor 618. Downstream of arterial pressure sensor 616 there is provided a stopcock 620 of the type described hereinabove with reference to any of FIGS. 11-60D, including a swabbable valve 622 having an elastomeric element 623.

FIG. 61A shows the stopcock in an operative orientation such as that shown in FIGS. 19A and 20A, FIGS. 29A and 30A, FIGS. 39A and 40A, FIGS. 49A and 50A and FIGS. 59A and 60A. As shown in FIGS. 19A, 20A, 39A and 40A, a liquid passes through the arterial set, including stopcock 620; from the bag 612 to the artery of the patient. Alternatively, as shown in the stopcocks illustrated in FIGS. 29A, 30A, 49A, 50A, 59A and 60A, this operative orientation may be utilized when a medical procedure requires a cessation of the flow of liquid in the arterial set.

FIG. 61B shows the stopcock in an operative orientation such as that shown in FIGS. 19B and 20B, FIGS. 29B and 30B, FIGS. 39B and 40B, FIGS. 49B and 50B and FIGS. 59B and 60B, which is typically employed for drawing blood or other fluids from the patient, by employing a syringe 624 coupled to the swabbable valve 622. It is appreciated that this operating position may also be used for supplying medicament to the patient via syringe 624.

FIG. 61C shows the stopcock in an operative orientation such as that shown, for example in FIGS. 19C and 20C, FIGS. 29C and 30C, FIGS. 39C and 40C, FIGS. 49C and 50C and FIGS. 59C and 60C, which is typically employed for supplying a liquid to the patient from the arterial set. Liquid flows through the stopcock and flushes the internal volume of the swabbable valve and of the port in which it is located, flushing residual liquid therefrom to the patient.

Because it enables an operator to easily draw blood without exposing the arterial line to the atmosphere, use of a stopcock shown in any of FIGS. 11-60D in a monitoring set reduces both the risk of contamination and the need for extra covers or plugs.

For routine use in arterial lines, the stopcock is employed in a position such as that shown in FIGS. 19A, 20A, 39A, 40A and 61A, where the fluid flows from the arterial line to the patient without making contact with the elastomeric element 623 of the valve 622.

To draw blood from the patient, the operator places the handle of the stopcock in the operative orientation shown in FIGS. 19B, 20B, 29B, 30B, 39B, 40B, 49B, 50B, 59B, 60B and 61B, introduces a syringe to the valve, thereby opening it, and draws blood.

After blood is drawn, residual blood remains in the internal volumes of the valve and the side port of the stopcock. This residual blood, if not removed from the stopcock, may cause damage to the patient as discussed hereinabove with reference to drawings 9C, 19C, 20C, 29C, 30C, 39C, 40C, 49C, 50C, 59C and 60C.

In order to clear the residual blood from the internal volumes, the operator places the handle of the stopcock in the operative orientation shown in FIGS. 19C, 20C, 29C, 30C, 39C, 40C, 49C, 50C, 59C, 60C and 61C. In this orientation, the flow of liquid in the arterial line flushes the internal volumes of both the valve and the side port of the stopcock and clears the residual blood therefrom.

For use of the stopcock in monitoring the arterial blood pressure of the patient, the flow of liquid must not come in contact with the elastomeric component of the valve. Therefore, when the operator has removed the residual blood from the internal volumes of the valve and the side port of the stopcock, he would again place the handle of the stopcock in the operative orientation seen in FIG. 61A.

It is appreciated that the stopcock structure shown and described hereinabove may have many advantageous uses in addition to those described specifically hereinabove.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

The invention claimed is:

1. A stopcock comprising:
   a housing defining a central bore and at least first, second and third ports, and
   a handle having a shaft portion in rotatable sealing engagement with said bore, which shaft portion is selectably positionable relative to said housing,
   said housing and said handle together defining at least one fluid passageway communicating between at least two of said at least first, second and third ports, said at least one fluid passageway being selectably defined by rotational positioning of said handle relative to said housing;
   said shaft portion of said handle defining a slightly conical circumferential outer surface and having first, second and third elongate bores, said first and second elongate bores being coaxial and said third bore being orthogonal to said first and second bores, said first second and third bores defining first, second and third bore openings, arranged for selectable communication with said first, second and third ports,
   said shaft portion also defining a flow guide disposed at a junction of said first, second and third bores.

2. A stopcock according to claim 1 and wherein said first, second and third elongate bores are generally coplanar.

3. A stopcock according to claim 1 and wherein said flow guide bifurcates at least one of said first, second and third elongate bores.

4. A stopcock according to claim 1 and wherein said flow guide directs a flow of liquid between said at least first, second and third ports and through said first, second and third elongate bores into an internal volume of at least one of said first, second and third ports for flushing thereof, when said handle is suitably positioned.

5. A stopcock according to claim 1 and wherein said flow guide comprises an outward facing edge adapted to prevent a flow of liquid when said fluid flow guide is not located opposite any of said first, second and third ports.

6. A stopcock according to claim 1 and also comprising a valve located within at least one of said first, second and third ports.

7. A stopcock according to claim 6 and wherein said valve has an open first end and a normally closed second end.

8. A stopcock according to claim 6 and wherein said at least one fluid passageway is configured for enabling flushing of an internal volume of said valve.

9. A stopcock according to claim 1 and wherein said handle and said housing are arrangeable in multiple mutual positions.

10. A stopcock according to claim 9 and wherein said flow guide and said at least one fluid passageway are configured for enabling flushing of an internal volume of at least one of said first, second and third ports by a fluid flow which does not flow entirely through said port whose internal volume is being flushed, when said housing and said handle are in at least one of said multiple mutual positions.

11. A stopcock according to claim 1 and wherein said at least one fluid passageway is configured for enabling flushing an internal volume of at least one of said first, second and third ports by a fluid flow which does not flow entirely through said port whose internal volume is being flushed.

12. A stopcock according to claim 1 and wherein said flow guide bifurcates at least one of said first, second and third elongate bores.

13. A stopcock comprising:
a housing defining a central bore and at least first, second and third ports, and
a handle having a shaft portion in rotatable sealing engagement with said bore, which shaft portion is selectably positionable relative to said housing,
said housing and said handle together defining at least one fluid passageway communicating between at least two of said at least first, second and third ports, said at least one fluid passageway being selectably defined by rotational positioning of said handle relative to said housing;
said shaft portion of said handle defining a slightly conical circumferential outer surface and having first, second and third elongate bores, said first and second elongate bores being coaxial and said third bore being orthogonal to said first and second bores, said first second and third bores defining first, second and third bore openings, arranged for selectable communication with said first, second and third ports,
said shaft portion also defining a flow guide disposed at a junction of said first, second and third bores,
and wherein said flow guide extends radially towards an inner facing wall of said central bore and an edge of said flow guide sealingly engages said inner facing wall of said central bore to prevent fluid communication between any of said first, second and third ports when said flow guide is not located opposite at least one of said at least first, second and third ports; and also comprising a valve located within at least one of said first, second and third ports.

14. A stopcock according to claim 13 and wherein said valve has an open first end and a normally closed second end.

15. A stopcock according to claim 13 and wherein said at least one fluid passageway is configured for enabling flushing of an internal volume of said valve.

16. A stopcock according to claim 13 and wherein said first, second and third elongate bores are generally coplanar.

17. A stopcock comprising:
a housing defining a central bore and at least first, second and third ports, and
a handle having a shaft portion in rotatable sealing engagement with said bore, which shaft portion is selectably positionable relative to said housing,
said housing and said handle together defining at least one fluid passageway communicating between at least two of said at least first, second and third ports, said at least one fluid passageway being selectably defined by rotational positioning of said handle relative to said housing;
said shaft portion of said handle defining a slightly conical circumferential outer surface and having first, second and third elongate bores, said first and second elongate bores being coaxial and said third bore being orthogonal to said first and second bores, said first second and third bores defining first, second and third bore openings, arranged for selectable communication with said first, second and third ports,
said shaft portion also defining a flow guide disposed at a junction of said first, second and third bores,
said flow guide being disposed in said first, second and third elongate bores in a manner such that fluid communication between opposite ends of said first and second elongate bores connecting at least two of said at least first, second and third ports takes place via said third elongate bore and wherein said flow guide directs an entire flow of liquid between said at least first, second and third ports and through said first and second elongate bores and said third elongate bore at least into the vicinity of an internal volume of at least one of said first, second and third ports for flushing thereof, when said handle is suitably positioned.

18. A stopcock according to claim 17 and wherein said valve has an open first end and a normally closed second end.

19. A stopcock according to claim 17 and wherein said at least one fluid passageway is configured for enabling flushing of an internal volume of said valve.

20. A stopcock according to claim 17 and wherein said flow guide bifurcates at least one of said first, second and third elongate bores.

21. A stopcock according to claim 17 and wherein said first, second and third elongate bores are generally coplanar.

22. A stopcock according to claim 17 and wherein said flow guide comprises an outward facing edge adapted to prevent a flow of liquid when said fluid flow guide is not located opposite any of said first, second and third ports.

* * * * *